US009388097B2

(12) United States Patent
Wampler et al.

(10) Patent No.: US 9,388,097 B2
(45) Date of Patent: Jul. 12, 2016

(54) METHODS FOR TREATING SUBSTRATES PRIOR TO METATHESIS REACTIONS, AND METHODS FOR METATHESIZING SUBSTRATES

(71) Applicant: Elevance Renewable Sciences, Inc., Woodridge, IL (US)

(72) Inventors: Keith M. Wampler, Brookfield, IL (US); Steven A. Cohen, Naperville, IL (US); Georg E. Frater, Ebnat-Kappel (CH); Levente Ondi, Veresegyhaz (HU); Jeno Varga, Budapest (HU)

(73) Assignee: Elevance Renewable Sciences, Inc., Woodridge, IL (US)

( * ) Notice: Subject to any disclaimer, the term of this patent is extended or adjusted under 35 U.S.C. 154(b) by 134 days.

(21) Appl. No.: 14/209,686

(22) Filed: Mar. 13, 2014

(65) Prior Publication Data

US 2014/0275595 A1    Sep. 18, 2014

Related U.S. Application Data

(60) Provisional application No. 61/784,321, filed on Mar. 14, 2013.

(51) Int. Cl.
| | |
|---|---|
| *C07C 6/04* | (2006.01) |
| *C07C 67/58* | (2006.01) |
| *C10G 3/00* | (2006.01) |

(Continued)

(52) U.S. Cl.
CPC ... *C07C 6/04* (2013.01); *C07C 7/12* (2013.01); *C07C 7/13* (2013.01); *C07C 67/58* (2013.01); *C10G 3/46* (2013.01); *C11B 3/02* (2013.01);*C11B 3/10* (2013.01); *C11B 3/12* (2013.01); *C07C 2531/22* (2013.01)

(58) Field of Classification Search
CPC ........................................................ C07C 6/04
USPC ........................................................ 554/194
See application file for complete search history.

(56) References Cited

U.S. PATENT DOCUMENTS

| | | | | |
|---|---|---|---|---|
| 5,378,783 A | * | 1/1995 | Okumura | C07C 7/14833 203/6 |
| 2005/0154221 A1 | * | 7/2005 | Lysenko | C07C 67/333 554/174 |

(Continued)

FOREIGN PATENT DOCUMENTS

| | | | | |
|---|---|---|---|---|
| EP | 0116408 A2 | * | 8/1984 | ............... C11B 3/06 |
| WO | WO 2009/020667 A1 | | 2/2009 | |
| WO | WO 2014/139676 A1 | | 9/2014 | |

OTHER PUBLICATIONS

International Search Report and Written Opinion of the International Searching Authority issued in PCT Patent Application No. PCT/US2014/026535, mailed Aug. 20, 2014, 12 pages.

(Continued)

*Primary Examiner* — Deborah D Carr
(74) *Attorney, Agent, or Firm* — Robert S. Dailey

(57) ABSTRACT

A method for treating a substrate prior to a metathesis reaction includes treating the substrate with a first agent configured to mitigate potentially adverse effects of one or more contaminants in the substrate on a catalyst used to catalyze the metathesis reaction. The treating reduces a level of the one or more contaminants by an amount sufficient to enable the metathesis reaction to proceed at a substrate-to-catalyst molar ratio of at least about 7,500 to 1. Methods for metathesizing substrates are described.

25 Claims, 10 Drawing Sheets

(51) Int. Cl.
| | |
|---|---|
| *C07C 7/12* | (2006.01) |
| *C07C 7/13* | (2006.01) |
| *C11B 3/02* | (2006.01) |
| *C11B 3/10* | (2006.01) |
| *C11B 3/12* | (2006.01) |

(56) References Cited

U.S. PATENT DOCUMENTS

| | | | | |
|---|---|---|---|---|
| 2011/0113679 | A1* | 5/2011 | Cohen | C10G 45/00 44/388 |
| 2011/0160472 | A1* | 6/2011 | Lemke | C10G 3/47 554/154 |
| 2011/0313180 | A1* | 12/2011 | Uptain | C10G 3/47 554/124 |
| 2013/0006012 | A1* | 1/2013 | Firth | C10G 45/00 560/218 |
| 2013/0035502 | A1* | 2/2013 | Cohen | C10G 29/205 560/129 |

OTHER PUBLICATIONS

Schrock, "Recent Advances in High Oxidation State Mo and W Imido Alkylidene Chemistry" Chem. Rev., 109, 2009, pp. 3211-3226.

Schrock et al., "Molybdenum and Tungsten Imido Alkylidene Complexes as Efficient Olefin-Metathesis Catalysts" Angew, Chem. Int. Ed., 42, 2003, pp. 4592-4633.

Schrock, "High Oxidation State Multiple Metal-Carbon Bonds" Chem. Rev., 102, 2002, pp. 145-179.

Wang, Chenbo, Fredrik Haeffner, Richard R. Schrock, and Amir H. Hoveyda. "Molybdenum-Based Complexes with Two Aryloxides and a Pentafluoroimido Ligand: Catalysts for Efficient Z—Selective Synthesis of a Macrocyclic Trisubstituted Alkene by Ring-Closing Metathesis." Angewandte Chemie International Edition 52, No. 7 (Feb. 11, 2013): 1939-1943.

Nelson, T. D. and Crouch, R. D., "Cu, Ni, and Pd Mediated Homocoupling Reactions in Biaryl Syntheses: The Ullmann Reaction" Organic Reactions, 2004, 63:3:pp.265-555, Oct. 19, 2015.

* cited by examiner

METHODS FOR TREATING SUBSTRATES PRIOR TO METATHESIS REACTIONS, AND METHODS FOR METATHESIZING SUBSTRATES

CROSS-REFERENCE TO RELATED APPLICATIONS

The present application claims the benefit of priority to U.S. Provisional Patent Application No. 61/784,321, filed Mar. 14, 2013, which is hereby incorporated by reference as though fully set forth herein.

BACKGROUND

The olefin metathesis reaction has established itself as one of the most powerful chemical reactions available for the synthetic preparation of alkenes. In recent years, a great deal of research has been directed to the development of new catalyst systems for use in olefin metathesis, with catalysts that incorporate transition metals such as ruthenium, molybdenum, or tungsten receiving the lion's share of attention within the chemical community. Two perennially popular catalysts systems are the ruthenium catalysts developed by Nobel laureate Robert H. Grubbs and the molybdenum and tungsten catalysts developed by Nobel laureate Richard R. Schrock.

One criterion by which to judge the efficacy of a metathesis catalyst is the turnover number ("TON") that can be achieved prior to deactivation of the catalyst. Often, catalyst systems that show efficacies in catalyzing an olefin metathesis reaction are susceptible to a variety of contaminants that may significantly reduce the TON that otherwise can be attained.

Natural feedstocks including but not limited to natural oils (e.g., vegetable oils, algal oils, animal fats, tall oils, and the like) and derivatives of natural oils (e.g., fatty acids and fatty acid esters) can be converted into industrially useful chemicals through olefin metathesis. However, catalyst efficiency and product conversion can vary dramatically depending on the purity of the feedstock that is being metathesized. One challenge in using natural feedstocks is that they may include impurities—sometimes in trace amounts—that do not exist in petroleum feedstocks. Often, these impurities react (and/or otherwise interact) with the metathesis catalyst and may drastically affect the efficiency of the catalyst and metathesis reaction. Moreover, the presence and level of various impurities in natural oils may vary from batch-to-batch, depending, for example, on the geographic location of the harvest, and even on the specific time of harvest as well as other growing conditions.

A systematic approach to mitigating the undesirable impact of contaminants present in metathesis feedstocks—particularly though not exclusively natural feedstocks—on the general efficiency and TON of the catalysts used to catalyze the olefin metathesis reaction is desirable.

SUMMARY

The scope of the present invention is defined solely by the appended claims, and is not affected to any degree by the statements within this summary.

By way of introduction, a method for treating a substrate prior to a metathesis reaction that embodies features of the present invention includes treating the substrate with a first agent configured to mitigate potentially adverse effects of one or more contaminants in the substrate on a catalyst used to catalyze the metathesis reaction. The treating reduces a level of the one or more contaminants by an amount sufficient to enable the metathesis reaction to proceed at a substrate-to-catalyst molar ratio of at least about 7,500 to 1.

A method for metathesizing a substrate embodying features of the present invention includes treating the substrate with a first agent, and reacting the substrate, following its treatment with the first agent, in a metathesis reaction in the presence of a metathesis catalyst. The substrate comprises a natural oil and/or a derivative thereof, and the first agent is configured to mitigate potentially adverse effects of one or more contaminants in the substrate on the metathesis catalyst. The treating reduces a level of the one or more contaminants by an amount sufficient to enable the metathesis reaction to proceed at a substrate-to-catalyst molar ratio of at least about 7,500 to 1.

DETAILED DESCRIPTION

Figure 1:
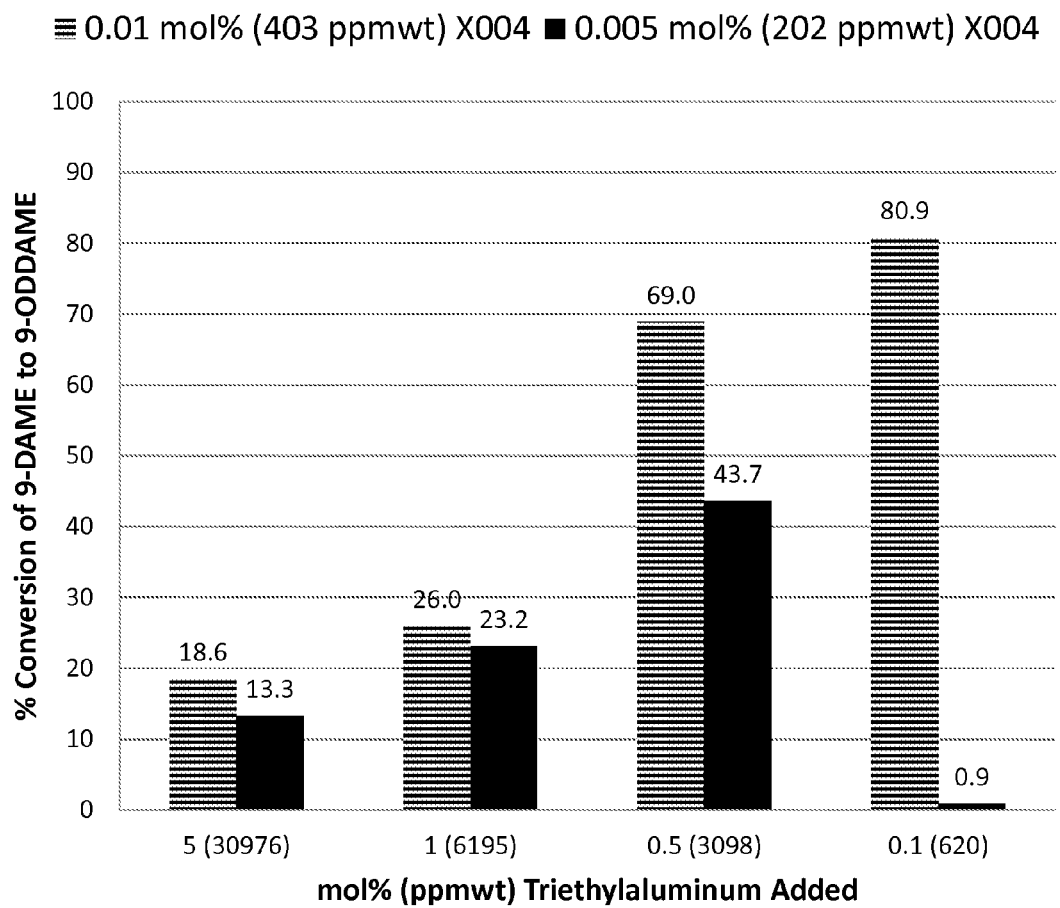
FIG. 1 is a chart showing the effect of a triethyl aluminum (herein "TEAL") treatment in the purification of 9-DAME.

Methods for the pretreatment of substrates to be used in metathesis reactions have been discovered and are described herein below. These pretreatment methods mitigate potentially adverse effects that one or more contaminants in the substrate can have on metathesis catalysts used for catalyzing the metathesis reaction, such that the efficiency of the catalyst (e.g., as quantified by its TON) can be increased. Since different feedstocks typically contain different types of impurities, methods in accordance with the present teachings, as further explained below, utilize different methodologies—and, in some embodiments, combinations of methodologies—in order to counteract the adverse effects of specific contaminants.

Throughout this description and in the appended claims, the following definitions are to be understood:

The term "olefin" refers to a hydrocarbon compound containing at least one carbon-carbon double bond. As used herein, the term "olefin" encompasses hydrocarbons having more than one carbon-carbon double bond (e.g., di-olefins, tri-olefins, etc.). In some embodiments, the term "olefin" refers to a group of carbon-carbon double bond-containing compounds with different chain lengths. In some embodiments, the term "olefin" refers to poly-olefins, straight, branched, and/or cyclic olefins.

The term "functionalized" and the phrase "functional group" refer to the presence in a molecule of one or more heteroatoms at a terminal and/or an internal position, wherein the one or more heteroatoms is an atom other than carbon and hydrogen. In some embodiments, the heteroatom constitutes one atom of a polyatomic functional group. Representative functional groups including but are not limited to halides, alcohols, amines, carboxylic acids, carboxylic esters, ketones, aldehydes, anhydrides, ether groups, cyano groups, nitro groups, sulfur-containing groups, phosphorous-containing groups, amides, imides, N-containing heterocycles, aromatic N-containing heterocycles, salts thereof, and the like, and combinations thereof.

The phrase "metathesis reaction" refers to a chemical reaction involving a single type of olefin or a plurality of different types of olefin, which is conducted in the presence of a metathesis catalyst, and which results in the formation of at least one new olefin product. The phrase "metathesis reaction" encompasses self-metathesis, cross-metathesis (aka co-metathesis; CM), ring-opening metathesis (ROM), ring-opening metathesis polymerizations (ROMP), ring-closing metathesis (RCM), acyclic diene metathesis (ADMET), and the like, and combinations thereof. In some embodiments, the phrase "metathesis reaction" refers to a chemical reaction involving a natural oil feedstock.

The term "mitigate" as used in reference to the adverse effects of a particular contaminant on a metathesis catalyst refers to a lessening in the severity of such effects. It is to be understood that the term "mitigate" encompasses but does not necessarily imply a 100% elimination of the adverse effects associated with a particular contaminant.

The term "contaminant" refers broadly and without limitation to any impurity—regardless of the amount in which it is present—admixed with a substrate to be used in olefin metathesis.

The phrase "protic material" refers to a material that contains a dissociable proton.

The phrase "polar material" refers to a material that has an uneven distribution of electrons and thus a permanent dipole moment.

The phrase "Lewis basic catalyst poison" refers generally to a heteroatom-containing material that can function as an electron pair donor.

The phrases "natural oils," "natural feedstocks," or "natural oil feedstocks" may refer to oils derived from plants or animal sources. The phrase "natural oil" includes natural oil derivatives, unless otherwise indicated. The phrases also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, camelina oil, and castor oil. Representative non-limiting examples of animal fats include lard, tallow, poultry fat, yellow grease, and fish oil. Tall oils are by-products of wood pulp manufacture.

The phrase "natural oil derivatives" may refer to the compounds or mixture of compounds derived from the natural oil using any one or combination of methods known in the art. Such methods include but are not limited to saponification, fat splitting, transesterification, esterification, hydrogenation (partial or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12-octadecadienoic acid), and linolenic acid (9,12,15-octadecatrienoic acid).

The phrase "low-molecular-weight olefin" refers to any straight, branched or cyclic olefin in the $C_2$ to $C_{30}$ range and/or any combination of such olefins. The phrase "low-molecular-weight olefin" encompasses mono-olefins, including but not limited to internal olefins, terminal olefins, and combinations thereof, as well as polyolefins, including but not limited to dienes, trienes, and the like, and combinations thereof. In some embodiments, the low-molecular-weight olefin is functionalized.

The term "ester" refers to compounds having a general formula R—COO—R', wherein R and R' denote any substituted or unsubstituted alkyl, alkenyl, alkynyl, or aryl group. In some embodiments, the term "ester" refers to a group of compounds having a general formula as described above, wherein the compounds have different chain lengths.

The term "alkyl" refers to straight, branched, cyclic, and/or polycyclic aliphatic hydrocarbon groups, which optionally may incorporate one or more heteroatoms within their carbon-carbon backbones (e.g., so as to form ethers, heterocycles, and the like), and which optionally may be functionalized.

The phrase "an amount sufficient to enable [a] metathesis reaction to proceed at a [specified] substrate-to-catalyst molar ratio" refers to a degree of reduction in concentration of a given contaminant. Determination of the amount of reduction necessary to attain a desired substrate-to-catalyst molar ratio lies well within the skill of the ordinary artisan in view of the guiding principles outlined herein, and will vary according to the nature of the particular contaminant and/or its starting concentration. Conditions that can affect the level of reduction include but are not limited to experimental parameters such as the reactivity and/or concentrations of reagents, the type of mixing and/or stirring provided (e.g., high-shear, low-intensity, etc.), reaction temperature, residence time, reaction pressure, reaction atmosphere (e.g., exposure to atmosphere vs. an inert gas, etc.), and the like, and combinations thereof.

The term "attached" as used in reference to a solid support and an agent used for treating a substrate prior to a metathesis reaction is to be understood broadly and without limitation to encompass a range of associative-type forces, including but not limited to covalent bonds, ionic bonds, physical and/or electrostatic attractive forces (e.g., hydrogen bonds, Van der Waals forces, etc.), and the like, and combinations thereof.

The phrases "slow addition" or "slowly added" may refer to fractional additions of the full catalyst loading over an extended period of time, in contrast to a single, full batch loading at one time. In some embodiments, the slow addition of catalyst may refer to catalyst that is fractionally added to a substrate or feedstock at a rate of approximately 10 ppmwt catalyst per hour (ppmwt/hr), 5 ppmwt/hr, 1 ppmwt/hr, 0.5 ppmwt/hr, 0.1 ppmwt/hr, 0.05 ppmwt/hr, or 0.01 ppmwt/hr. In other embodiments, the catalyst is slowly added at a rate of between about 0.01-10 ppmwt/hr, 0.05-5 ppmwt/hr, or 0.1-1 ppmwt/hr.

The phrase "continuous addition" or "continuously added" may also refer to the addition of a percentage of a catalyst loading over an extended period of time, in contrast to a batch loading of the entire catalyst loading at one time. In a continuous addition, the catalyst is being added to a substrate or feedstock at a continuous or near-continuous frequency (i.e., at least once per minute) as opposed to one batch loading, or several fractional batch loadings at more extended intervals, such as once per hour.

It is to be understood that elements and features of the various representative embodiments described below may be combined in different ways to produce new embodiments that likewise fall within the scope of the present teachings.

By way of general introduction, a method in accordance with the present teachings for treating a substrate prior to a metathesis reaction includes treating the substrate with a first agent configured to mitigate potentially adverse effects of one or more contaminants in the substrate on a catalyst used to catalyze the metathesis reaction. In some embodiments, the treating reduces a level of the one or more contaminants by an amount sufficient to enable the metathesis reaction to proceed at a substrate-to-catalyst molar ratio of at least about 7,500 to 1.

In some embodiments, the substrate comprises one or a plurality of functional groups. In some embodiments, the substrate comprises a heteroatom which, in some embodiments, comprises oxygen. In some embodiments, the substrate comprises a natural oil and/or a derivative thereof, or both of which, in some embodiments, is optionally functionalized. Representative examples of natural oils for use in accordance with the present teachings include but are not limited to vegetable oils, algal oils, animal fats, tall oils (e.g., by-products of wood pulp manufacture), derivatives of these oils, and the like, and combinations thereof. Representative examples of vegetable oils for use in accordance with the present teachings include but are not limited to canola oil, rapeseed oil, coconut oil, corn oil, cottonseed oil, olive oil, palm oil, peanut oil, safflower oil, sesame oil, soybean oil, sunflower oil, high oleic sunflower oil, linseed oil, palm kernel oil, tung oil, jatropha oil, mustard oil, pennycress oil, camelina oil, hemp oil, castor oil, and the like, and combinations thereof. Representative examples of animal fats for use in accordance with the present teachings include but are not limited to lard, tallow, poultry fat, yellow grease, brown grease, fish oil, and the like, and combinations thereof. In some embodiments, the natural oil may be refined, bleached, and/or deodorized. In some embodiments, the natural oil is selected from the group consisting of canola oil, rapeseed oil, corn oil, cottonseed oil, peanut oil, sesame oil, soybean oil, sunflower oil, linseed oil, palm oil, tung oil, and combinations thereof.

Representative examples of natural oil derivatives for use in accordance with the present teachings include but are not limited to gums, phospholipids, soapstock, acidulated soapstock, distillate or distillate sludge, fatty acids, fatty acid esters (e.g., non-limiting examples such as 2-ethylhexyl ester, etc.), hydroxy-substituted variations thereof, and the like, and combinations thereof. In some embodiments, the natural oil derivative comprises an ester. In some embodiments, the derivative is selected from the group consisting of a monoacylglyceride (MAG), a diacylglyceride (DAG), a triacylglyceride (TAG), and combinations thereof. In some embodiments, the natural oil derivative comprises a fatty acid methyl ester (FAME) derived from the glyceride of the natural oil.

In some embodiments, the metathesis reaction comprises self-metathesis of a natural oil and/or a derivative thereof. In some embodiments, the metathesis reaction comprises cross-metathesis between a natural oil and/or a derivative thereof, and a low and/or a high molecular weight olefin. In some embodiments, the metathesis reaction comprises cross-metathesis between a natural oil and/or a derivative thereof, and a low molecular weight olefin. In some embodiments, the metathesis reaction comprises cross-metathesis between a natural oil and/or a derivative thereof, and a high molecular weight olefin.

All manner of metathesis reactions are contemplated for use in accordance with the present teachings. Representative types of metathesis reactions include but are not limited to self-metathesis, CM, ROM, ROMP, RCM, ADMET, and the like, and combinations thereof. In some embodiments, the metathesis reaction is catalyzed by a ruthenium alkylidene complex. In some embodiments, the metathesis reaction is catalyzed by a molybdenum alkylidene complex. In some embodiments, the metathesis reaction is catalyzed by a tungsten alkylidene complex. In some embodiments, the metathesis reaction comprises ring-closing metathesis. In some embodiments, the metathesis reaction comprises self-metathesis of an optionally functionalized olefin reactant. In some embodiments, the optionally functionalized olefin reactant comprises a natural oil. In some embodiments, the metathesis reaction comprises cross-metathesis between an optionally functionalized olefin reactant and an optionally functionalized olefin co-reactant. In some embodiments, the optionally functionalized olefin reactant comprises a natural oil, and the optionally functionalized olefin co-reactant comprises a low-molecular weight olefin. In some embodiments, the optionally functionalized olefin reactant comprises a natural oil, and the optionally functionalized olefin co-reactant comprises a fatty acid methyl ester with representative FAMEs including but not limited to decenoic acid methyl esters (e.g., 9-DAME), undecenoic acid methyl esters (e.g., 9-UDAME), dodecenoic acid methyl esters (e.g., 9-DDAME), octadecene dicarboxylic acid dimethyl esters (e.g., 9-ODDAME), and the like, and combinations thereof.

In some embodiments, the low-molecular-weight olefin is an "α-olefin" (aka "terminal olefin") in which the unsaturated carbon-carbon bond is present at one end of the compound. In some embodiments, the low-molecular-weight olefin is an internal olefin. In some embodiments, the low-molecular-weight olefin is functionalized. In some embodiments, the low-molecular-weight olefin is a polyolefin. In some embodiments, the low-molecular-weight olefin comprises one or a plurality of substructures having a formula —CH=CH—CH$_2$—CH=CH—. In some embodiments, the low-molecular weight olefin is a $C_2$-$C_{30}$ olefin. In some embodiments, the low-molecular weight olefin is a $C_2$-$C_{30}$ α-olefin. In some embodiments, the low-molecular weight olefin is a $C_2$-$C_{25}$ olefin. In some embodiments, the low-molecular weight olefin is a $C_2$-$C_{25}$ α-olefin. In some embodiments, the low-molecular weight olefin is a $C_2$-$C_{20}$ olefin. In some embodiments, the low-molecular weight olefin is a $C_2$-$C_{20}$ α-olefin. In some embodiments, the low-molecular weight olefin is a $C_2$-$C_{15}$ olefin. In some embodiments, the low-molecular weight olefin is a $C_2$-$C_{15}$ α-olefin. In some embodiments, the low-molecular weight olefin is a $C_2$-$C_{14}$ olefin. In some embodiments, the low-molecular weight olefin is a $C_2$-$C_{14}$ α-olefin. In some embodiments, the low-molecular weight olefin is a $C_2$-$C_{10}$ olefin. In some embodiments, the low-molecular weight olefin is a $C_2$-$C_{10}$ α-olefin. In some embodiments, the low-molecular weight olefin is a $C_2$-$C_8$ olefin. In some embodiments, the low-molecular weight olefin is a $C_2$-$C_8$ α-olefin. In some embodiments, the low-molecular weight olefin is a $C_2$-$C_6$ olefin. In some embodiments, the low-molecular weight olefin is a $C_2$-$C_6$ α-olefin. Representative low-molecular-weight olefins include but are not limited to ethylene, propylene, 1-butene, 2-butene, isobutene, 1-pentene, 2-pentene, 3-pentene, 2-methyl-1-butene, 2-methyl-2-butene, 3-methyl-1-butene, cyclobutene, cyclopentene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, 1-hexene, 2-hexene, 3-hexene, cyclohexene, 1,4-pentadiene, 1,4-hexadiene, 1,4-heptadiene, 1,4-octadiene, 1,4-nonadiene, 1,4-decadiene, 2,5-heptadiene, 2,5-octadiene, 2,5-nonadiene, 2,5-decadiene, 3,6-nonadiene, 3,6-decadiene, 1,4,6-octatriene, 1,4,7-octatriene, 1,4,6-nonatriene, 1,4,7-nonatriene, 1,4,6-decatriene, 1,4,7-decatriene, 2,5,8-decatriene, and the like, and combinations thereof. In some embodiments, the low-molecular-weight olefin is an α-olefin selected from the group consisting of styrene, vinyl cyclohexane, and a combination thereof. In some embodiments, the low-molecular weight olefin is a mixture of linear and/or branched olefins in the $C_4$-$C_{10}$ range. In some embodiments, the low-molecular weight olefin is a mixture of linear and/or branched $C_4$ olefins (e.g., combinations of 1-butene, 2-butene, and/or iso-butene). In some embodiments, the low-molecular weight olefin is a mixture of linear and/or branched olefins in the higher $C_{11}$-$C_{14}$ range.

In some embodiments, the metathesis reaction comprises the reaction of two triglycerides present in a natural feedstock in the presence of a metathesis catalyst (self-metathesis), wherein each triglyceride comprises at least one carbon-carbon double bond, thereby forming a new mixture of olefins and esters that in some embodiments comprises a triglyceride dimer. In some embodiments, the triglyceride dimer comprises more than one carbon-carbon double bond, such that higher oligomers also can form. In some embodiments, the metathesis reaction comprises the reaction of an olefin (e.g., a low-molecular weight olefin) and a triglyceride in a natural feedstock that comprises at least one carbon-carbon double bond, thereby forming new olefinic molecules as well as new ester molecules (cross-metathesis).

In some embodiments, the metathesis catalyst comprises a transition metal. In some embodiments, the metathesis catalyst comprises ruthenium. In some embodiments, the metathesis catalyst comprises rhenium. In some embodiments, the metathesis catalyst comprises tantalum. In some embodiments, the metathesis catalyst comprises tungsten. In some embodiments, the metathesis catalyst comprises molybdenum.

In some embodiments, the metathesis catalyst comprises a ruthenium carbene complex and/or an entity derived from such a complex. In some embodiments, the metathesis catalyst comprises a material selected from the group consisting of a ruthenium vinylidene complex, a ruthenium alkylidene complex, a ruthenium methylidene complex, a ruthenium benzylidene complex, and combinations thereof, and/or an entity derived from any such complex or combination of such complexes. In some embodiments, the metathesis catalyst comprises a ruthenium carbene complex comprising at least one phosphine ligand and/or an entity derived from such a complex. In some embodiments, the metathesis catalyst comprises a ruthenium carbene complex comprising at least one tricyclohexylphosphine ligand and/or an entity derived from such a complex. In some embodiments, the metathesis catalyst comprises a ruthenium carbene complex comprising at least two tricyclohexylphosphine ligands [e.g., $(PCy_3)_2Cl_2Ru=CH—CH=C(CH_3)_2$, etc.] and/or an entity derived from such a complex. In some embodiments, the metathesis catalyst comprises a ruthenium carbene complex comprising at least one imidazolidine ligand and/or an entity derived from such a complex. In some embodiments, the metathesis catalyst comprises a ruthenium carbene complex comprising an isopropyloxy group attached to a benzene ring and/or an entity derived from such a complex.

Non-limiting exemplary metathesis catalysts and process conditions are described in PCT/US2008/009635, incorporated by reference herein in its entirety. In some embodiments, the metathesis catalyst comprises a Grubbs-type olefin metathesis catalyst and/or an entity derived therefrom. In some embodiments, the metathesis catalyst comprises a first-generation Grubbs-type olefin metathesis catalyst and/or an entity derived therefrom. In some embodiments, the metathesis catalyst comprises a second-generation Grubbs-type olefin metathesis catalyst and/or an entity derived therefrom. In some embodiments, the metathesis catalyst comprises a first-generation Hoveda-Grubbs-type olefin metathesis catalyst and/or an entity derived therefrom. In some embodiments, the metathesis catalyst comprises a second-generation Hoveda-Grubbs-type olefin metathesis catalyst and/or an entity derived therefrom. In some embodiments, the metathesis catalyst comprises one or a plurality of the ruthenium carbene metathesis catalysts sold by Materia, Inc. of Pasadena, Calif. and/or one or more entities derived from such catalysts. Representative metathesis catalysts from Materia, Inc. for use in accordance with the present teachings include but are not limited to those sold under the following product numbers as well as combinations thereof: product no. C823 (CAS no. 172222-30-9), product no. C848 (CAS no. 246047-72-3), product no. C601 (CAS no. 203714-71-0), product no. C627 (CAS no. 301224-40-8), product no. C571 (CAS no. 927429-61-6), product no. C598 (CAS no. 802912-44-3), product no. C793 (CAS no. 927429-60-5), product no. C801 (CAS no. 194659-03-9), product no. C827 (CAS no. 253688-91-4), product no. C884 (CAS no. 900169-53-1), product no. C833 (CAS no. 1020085-61-3), product no. C859 (CAS no. 832146-68-6), product no. C711 (CAS no. 635679-24-2), product no. C933 (CAS no. 373640-75-6).

In some embodiments, the metathesis catalyst comprises a molybdenum and/or tungsten carbene complex and/or an entity derived from such a complex. In some embodiments, the metathesis catalyst comprises a Schrock-type olefin metathesis catalyst and/or an entity derived therefrom. In some embodiments, the metathesis catalyst comprises a high-oxidation-state alkylidene complex of molybdenum and/or an entity derived therefrom. In some embodiments, the metathesis catalyst comprises a high-oxidation-state alkylidene complex of tungsten and/or an entity derived therefrom. In some embodiments, the metathesis catalyst comprises molybdenum (VI). In some embodiments, the metathesis catalyst comprises tungsten (VI). In some embodiments, the metathesis catalyst comprises a molybdenum- and/or a tungsten-containing alkylidene complex of a type described in one or more of (a) *Angew. Chem. Int. Ed. Engl.* 2003, 42, 4592-4633; (b) *Chem. Rev.* 2002, 102, 145-179; (c) *Chem. Rev.* 2009, 109, 3211-3226, (d) *Nature* 2011, 479, 88-93, and/or *Angew. Chem. Int. Ed. Engl.* 2013, 52, 1939-1943, each of which is incorporated by reference herein in its entirety, except that in the event of any inconsistent disclosure or definition from the present specification, the disclosure or definition herein shall be deemed to prevail. In some embodiments, the metathesis catalyst is selected from the group consisting of:

Mo(N-2,6-$^i$Pr$_2$-C$_6$H$_3$)(CHCMe$_2$Ph)(2,5-dimethylpyrrolide)(O-2,6-Ph$_2$C$_6$H$_3$) (herein "X004");

Mo(N-2,6-$^i$Pr$_2$-C$_6$H$_3$)(CHCMe$_2$Ph)(2,5-dimethylpyrrolide)[(R)-3,3'-dibromo-2'-(tert-butyldimethylsilyloxy)-5,5',6,6',7,7',8,8'-octahydro-1,1'-binaphth-2-oate)] (herein "X007");

Mo(N-2,6-$^i$Pr$_2$-C$_6$H$_3$)(CHCMe$_2$Ph)(2,5-dimethylpyrrolide)[(R)-3,3'-dibromo-2'-methoxy-5,5',6,6',7,7',8,8'-octahydro-1,1'-binaphth-2-oate)] (herein "X008"); and W(N-2,6-Cl$_2$-C$_6$H$_3$)(CHCMe$_3$)(2,5-dimethylpyrrolide)[(R)-3,3'-dibromo-2'-(tert-butyldimethylsilyloxy)-5,5',6,6',7,7',8,8'-octahydro-1,1'-binaphth-2-oate)] (herein "X022");

Mo(N-2,6-$^i$Pr$_e$-C$_6$H$_3$)(CHCMe$_2$Ph)(pyrrolide)(O-2,6-$^t$Bu$_2$C$_6$H$_3$) (herein "X027");

Mo(N-2,6-Me$_2$-C$_6$H$_3$)(CHCMe$_2$Ph)(2,5-dimethylpyrrolide)[(S)-3,3'-dibromo-2'-(tert-butyldimethylsilyloxy)-5,5',6,6',7,7',8,8'-octahydro-1,1'-binaphth-2-oate)] (herein "X030");

W(N-2,6-Cl$_2$-C$_6$H$_3$)(CHCMe$_3$)(pyrrolide)[2,6-bis(2',4',6'-triisopropyl-phenyl)-phenoxide] (herein "X038");

Mo(N-1-adamantyl)(CHCMe$_2$Ph)(2,5-dimethylpyrrolide)[(R)-3,3'-dibromo-2'-(tert-butyldimethylsilyloxy)-5,5',6,6',7,7',8,8'-octahydro-1,1'-binaphth-2-oate)] (herein "X048");

Mo(N-2,6-$^i$Pr$_2$-C$_6$H$_3$)(CHCMe$_2$Ph)(2,5-dimethylpyrrolide)(O-2,3,5,6-Ph$_4$C$_6$H$_1$) (herein "X051");

Mo(N-2,6-$^i$Pr$_2$-C$_6$H$_3$)(CHCMe$_2$Ph)(2,5-dimethylpyrrolide)(O-2,3,5,6-Ph$_4$-4-Br—C$_6$) (herein "X052");

W(N-2,6-Cl$_2$-C$_6$H$_3$)(CHCMe$_3$)(2,5-dimethyl-pyrrolide)(O-2,3,5,6-Ph$_4$-4-Br—C$_6$) (herein "X123") and W(N-2,6-Cl$_2$-C$_6$H$_3$)(CHCMe$_3$)(2,5-dimethyl-pyrrolide)(O-2,3,5,6-Ph$_4$-C$_6$H$_1$) (herein "X154").

In some embodiments, the metathesis catalyst is selected from the group consisting of the following molybdenum-based complexes available from XiMo AG (Lucerne, Switzerland):

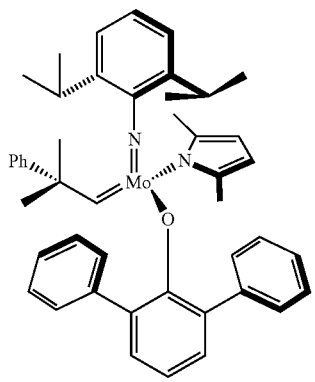
X004

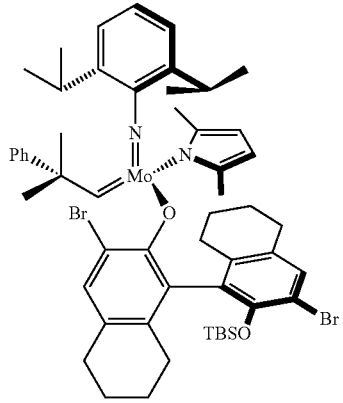
X007

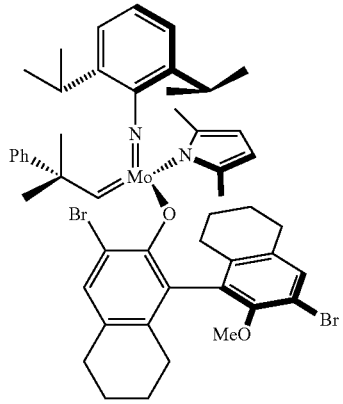
X008

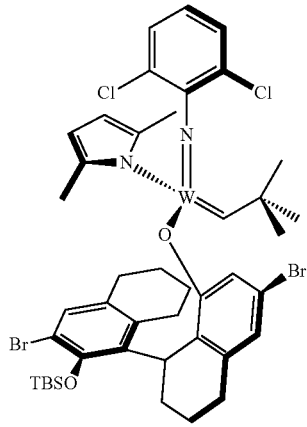
X022

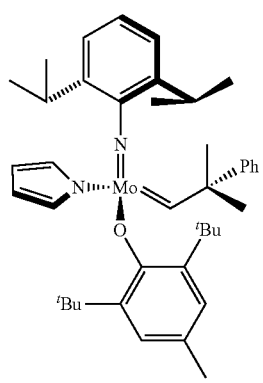
X027

-continued

X038
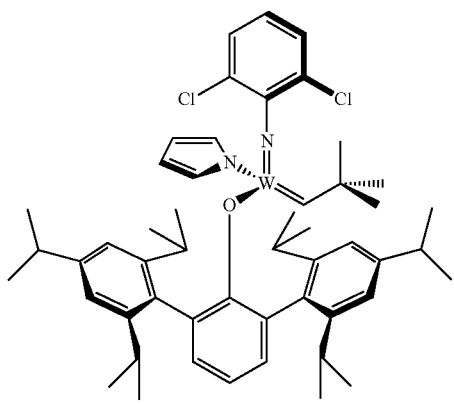

X048
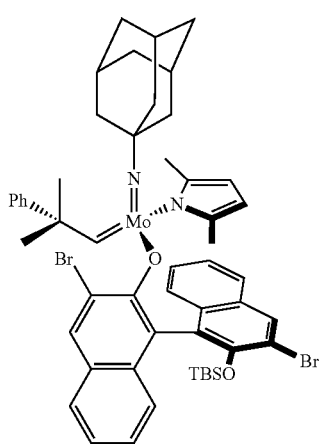

X051
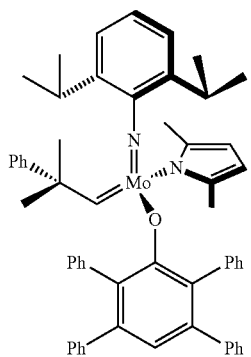

X030
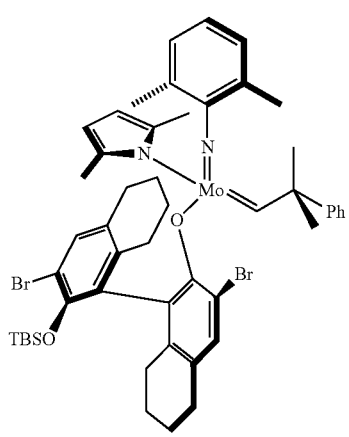

-continued

X052
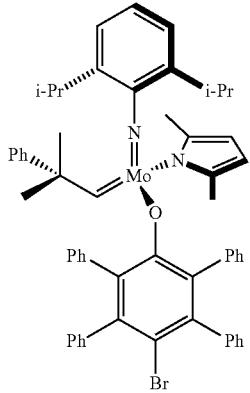

X123
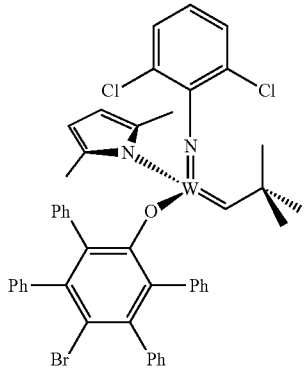

X154
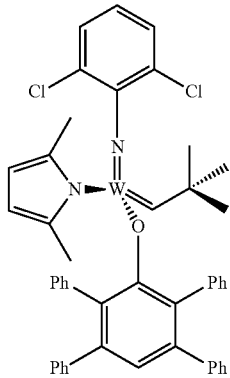

As presently contemplated, all manner of contaminants with the potential to adversely affect the performance of a metathesis catalyst can be addressed in accordance with the present teachings. By way of example, representative contaminants include but are not limited to water, peroxides, peroxide decomposition products, hydroperoxides, protic materials, polar materials, Lewis basic catalyst poisons, and the like, and combinations thereof. It is to be understood that some contaminants may properly be classified in multiple categories (e.g., an alcohol can be considered both a protic material and a polar material). It is to be further understood that different catalysts may have different susceptibilities to a particular contaminant, and that a contaminant that adversely affects the performance of one catalyst (e.g., a ruthenium-based catalyst) may or may not affect (to a similar extent or to any extent whatsoever) a different catalyst (e.g., a molybdenum-based catalyst). By way of illustration, while neither desiring to be bound by any particular theory nor intending to limit in any measure the scope of the appended claims or their equivalents, it is presently believed that ruthenium catalysts are typically more sensitive to peroxides than are molybdenum catalysts. Moreover, while neither desiring to be bound by any particular theory nor intending to limit in any measure the scope of the appended claims or their equivalents, it is presently believed that moisture (and/or protic materials in general) represents a bigger problem for high-valent olefin metathesis catalysts (e.g., molybdenum catalysts) than the peroxides that are so detrimental to ruthenium catalysts. Thus, it is presently believed that the removal of peroxides from feedstocks used with molybdenum catalysts—while improving the performance of the molybdenum catalysts—is necessary but may not be sufficient to make a feedstock suitable for molybdenum-catalyzed metathesis. Additionally, it is presently believed that the slow addition of catalyst to a substrate, with or without removal of the substrate contaminants, may improve the performance of the metathesis catalyst.

Representative protic materials that may be found as contaminants in a substrate that is to be reacted in a metathesis reaction include but are not limited to materials having a hydrogen atom bonded to oxygen (e.g., carboxylic acids, alcohols, and the like) and/or a hydrogen atom bonded to nitrogen (e.g., primary amines, secondary amines, and the like). In some embodiments, particularly though not exclusively in natural oil substrates, a protic material contaminant may comprise a carboxylic acid functional group, a hydroxyl functional group, or a combination thereof. In some embodiments, the protic material is selected from the group consisting of free fatty acids, hydroxyl-containing materials, MAGs, DAGs, and the like, and combinations thereof.

Representative polar materials that may be found as contaminants in a substrate that is to be reacted in a metathesis reaction include but are not limited to heteroatom-containing materials such as oxygenates. In some embodiments, the polar material is selected from the group consisting of alcohols, aldehydes, ethers, and the like, and combinations thereof. In some embodiments, the polar material comprises an aldehyde.

Representative Lewis basic catalyst poisons that may be found as contaminants in a substrate that is to be reacted in a metathesis reaction include but are not limited to heteroatom-containing materials. In some embodiments, the Lewis basic catalyst poisons are selected from the group consisting of N-containing materials, P-containing materials, S-containing materials, and the like, and combinations thereof.

In some embodiments, a substrate to be reacted in a metathesis reaction comprises one contaminant with the potential to adversely affect the performance of a metathesis catalyst. In other embodiments, a substrate to be reacted in a metathesis reaction comprises a plurality of contaminants with the potential to adversely affect the performance of a metathesis catalyst. In some embodiments, the substrate comprises a plurality of contaminants and the method comprises reducing levels of two or more of the contaminants. In some embodiments, the substrate comprises a plurality of contaminants and the method comprises reducing levels of three or more of the contaminants. In some embodiments, the substrate comprises a plurality of contaminants and the method comprises reducing levels of four or more of the contaminants. In some embodiments, the substrate comprises a plurality of contaminants and the method comprises reducing levels of five or more of the contaminants.

In certain embodiments, the efficacy of the metathesis catalyst may be improved (e.g., the TON may be increased or the overall catalyst loading may be decreased) through slow addition of the catalyst to a substrate. In some embodiments, the overall catalyst loading may be decreased by at least 10%, at least 20%, or at least 30% in comparison to achieve the same TON as a single, full batch loading. The slow addition of overall catalyst loading may comprise adding fractional catalyst loadings to the substrate at an average rate of approximately 10 ppmwt catalyst per hour (ppmwt/hr), 5 ppmwt/hr, 1 ppmwt/hr, 0.5 ppmwt/hr, 0.1 ppmwt/hr, 0.05 ppmwt/hr, or 0.01 ppmwt/hr. In other embodiments, the catalyst is slowly added at a rate of between about 0.01-10 ppmwt/hr, 0.05-5 ppmwt/hr, or 0.1-1 ppmwt/hr. The slow addition of the catalyst may be conducted in batch loadings at frequencies of every 5 minutes, 15 minutes, 30 minutes, 1 hour, 2 hours, 4 hours, 12 hours, or 1 day. In other embodiments, the slow addition is conducted in a continuous addition process.

In some embodiments, the substrate is treated with at least one agent (as described in detail below) prior to the slow addition of the catalyst. In other embodiments, the slow addition of the catalyst improves the efficacy of the catalyst independent of any treatment of the substrate.

In some embodiments, the first agent used to treat the substrate prior to the metathesis reaction is configured to mitigate the potentially adverse effects of two or more of the contaminants. In some embodiments, the first agent is configured to mitigate the potentially adverse effects of three or more of the contaminants. In some embodiments, the first agent is configured to mitigate the potentially adverse effects of four or more of the contaminants. In some embodiments, the first agent is configured to mitigate the potentially adverse effects of five or more of the contaminants. In some embodiments, the first agent is configured to mitigate the potentially adverse effects of water on the catalyst. In some embodiments, the first agent is configured to mitigate the potentially adverse effects of peroxides, hydroperoxides, and/or peroxide decomposition products on the catalyst. In some embodiments, the first agent is configured to mitigate the potentially adverse effects of protic materials on the catalyst. In some embodiments, the first agent is configured to mitigate the potentially adverse effects of polar materials on the catalyst. In some embodiments, the first agent is configured to mitigate the potentially adverse effects of water, peroxides, hydroperoxides, and/or peroxide decomposition products, protic materials, and/or polar materials on the catalyst.

In some embodiments, methods in accordance with the present teachings further comprise treating the substrate—simultaneously and/or successively—with a second agent that is configured to mitigate potentially adverse effects of one or more of the contaminants. In some embodiments, methods in accordance with the present teachings further comprise treating the substrate—simultaneously and/or successively—with a second agent and—simultaneously and/or successively—with a third agent, each of which is individually configured to mitigate potentially adverse effects of one or more of the contaminants. In some embodiments, methods in accordance with the present teachings further comprise treating the substrate—simultaneously and/or successively—with a plurality of additional agents, each of which is individually configured to mitigate potentially adverse effects of one or more of the contaminants.

The nature of the first agent, second agent, third agent, and any additional agents used to treat a substrate in accordance with the present teachings is determined in view of the nature of the particular substrate or substrates, in view of the nature of the particular contaminant (or contaminants), and/or in view of the known sensitivities of a particular metathesis catalyst. Some agents are incompatible with (e.g., reactive towards) certain functional groups and, in such embodiments, it may be less desirable to use these agents to treat substrates containing the incompatible functional groups (e.g., using $LiAlH_4$ in large amounts to treat an ester-containing natural oil) or one skilled in the art might choose to employ such agents but limit the amount or the conditions for the treatment. Similarly, some agents are extremely reactive (e.g., dangerously exothermically so) towards some contaminants, such that it may be advisable for safety reasons (a) not to use the highly reactive agents in the known presence of the contaminant, (b) first ensure that the contaminant is present in only trace amounts below some safe threshold level before attempting the treatment (e.g., using an organometallic reagent to reduce moisture level in a substrate), and/or (c) perform a bulk removal of the contaminant starting with a less reactive agent prior to removing trace amounts of residual contaminant using the more highly reactive agent.

In some embodiments, the first agent, second agent, third agent, and any additional agents may be a Group I, II, or III metal alkyl. Useful Group I, II, and IIIA metal alkyls are compounds of the formula MRm wherein M is a Group II or IIIA metal, each R is independently an alkyl radical of 1 to about 20 carbon atoms, and m corresponds to the valence of M. Examples of useful metals, M, include lithium, sodium, potassium, magnesium, calcium, zinc, cadmium, aluminum, and gallium. Examples of suitable alkyl radicals, R, include methyl, ethyl, butyl, hexyl, decyl, tetradecyl, and eicosyl. Specific examples of such compounds include $Mg(CH_3)_2$, $Mg(C_2H_5)_2$, $Mg(C_2H_5)(C_4H_9)$, $Mg(C_4H_9)_2$, $M_9(C_6H_{13})_2$, $M_9(C_{12}H_{25})_2$, $Zn(CH_3)_2$, $Zn(C_2H_5)_2$, $Zn(C_4H_9)_2$, $Zn(C_4H_9)(C_8H_{17})$, $Zn(C_6H_{13})_2$, $Zn(C_6H_{13})_2$, $Al(C_2H_5)_3$, $Al(CH_3)_3$, $Al(n-C_4H_9)_3$, $Al(C_8H_{17})_3$, $Al(iso-C_4H_9)_3$, $Al(C_{12}H_{25})_3$, and combinations thereof. If desired, metal alkyls having one or more halogen or hydride groups can be employed, such as ethylaluminum dichloride, diethylaluminum chloride, diethylaluminum hydride, Grignard reagents, diisobutylaluminum hydride, and the like.

In some embodiments, the first agent, second agent, third agent, and/or any additional agents used in accordance with the present teachings are each individually selected from the group consisting of heat, molecular sieves, alumina (aluminum oxide), silica gel, montmorillonite clay, fuller's earth, bleaching clay, diatomaceous earth, zeolites, kaolin, activated metals (e.g., Cu, Mg, and the like), acid anhydrides (e.g., acetic anhydride "$Ac_2O$" and the like) activated carbon (a.k.a., activated charcoal), soda ash, metal hydrides (e.g., alkaline earth metal hydrides such as $CaH_2$ and the like), metal sulfates (e.g., alkaline earth metal sulfates such as calcium sulfate, magnesium sulfate, and the like; alkali metal sulfates such as potassium sulfate, sodium sulfate, and the like; and other metal sulfates such as aluminum sulfate, potassium magnesium sulfate, and the like), metal halides (e.g., alkali earth metal halides such as potassium chloride and the like), metal carbonates (e.g., calcium carbonate, sodium carbonate, and the like), metal silicates (e.g., magnesium silicate and the like), phosphorous pentoxide, metal aluminum hydrides (e.g., alkali metal aluminum hydrides such as $LiAlH_4$, $NaAlH_4$ and the like), alkyl aluminum hydrides (e.g., $iBu_2AlH$ a.k.a. DIBALH), metal borohydrides (e.g., alkali metal borohydrides such as $LiBH_4$, $NaBH_4$, and the like), organometallic reagents (e.g., Grignard reagents; organolithium reagents such as n-butyl lithium, t-butyl lithium, sec-butyl lithium; trialkyl aluminums such as triethyl aluminum ("$Et_3Al$"), tributyl aluminum, triisobutyl aluminum, triisopropyl aluminum, trioctyl aluminum ("$Oc_3Al$"), and the like, metal amides (e.g., lithium diisopropyl amide a.k.a. LDA, metal bis(trimethylsilyl)amides such as KHMDS, and the like), palladium on carbon (Pd/C) catalysts, and combinations thereof.

Further description regarding the use of heat as an agent to treat a substrate prior to a metathesis reaction is provided in United States Patent Application Publication No. US 2011/0313180 A1, which is assigned to the assignee of the present invention. Further description regarding the use of reducing agents and cation-inorganic base compositions as agents for treating a substrate prior to a metathesis reaction is provided in United States Patent Application Publication No. US 2011/0160472 A1, which is assigned to the assignee of the present invention. The entire contents of each of the three above-identified documents are incorporated herein in their entirety, except that in the event of any inconsistent disclosure or definition from the present specification, the disclosure or definition herein shall be deemed to prevail.

In some embodiments, the first agent, second agent, third agent, and/or any additional agents used in accordance with the present teachings are each individually selected from the group consisting of heat, optionally heat-treated molecular sieves, optionally heat-treated alumina (e.g., activated, acidic, basic, and neutral), optionally heat-treated silica gel, montmorillonite clay, fuller's earth, bleaching clay, diatomaceous earth (e.g., as sold under the trade name CELITE), zeolites, kaolin, activated metals, acid anhydrides, activated carbon, soda ash, metal hydrides, metal sulfates, metal halides, metal carbonates, metal silicates, phosphorous pentoxide, metal aluminum hydrides, alkyl aluminum hydrides, metal borohydrides, organometallic reagents, metal amides, and the like, and combinations thereof.

In some embodiments, the first agent, second agent, third agent, and/or any additional agents used in accordance with the present teachings are each individually selected from the group consisting of optionally heat-treated activated molecular sieves, optionally heat-treated activated alumina, optionally heat-treated activated acidic alumina, optionally heat-treated activated neutral alumina, optionally heat-treated activated basic alumina, alkaline earth metal hydrides, alkaline earth metal sulfates, alkali metal sulfates, alkali earth metal halides, alkali metal aluminum hydrides, alkali metal borohydrides, Grignard reagents; organolithium reagents, trialkyl aluminums, metal bis(trimethylsilyl)amides, and the like, and combinations thereof.

In some embodiments, the first agent, second agent, third agent, and/or any additional agents used in accordance with the present teachings are each individually selected from the group consisting of $CaH_2$, activated Cu, activated Mg, acetic anhydride, calcium sulfate, magnesium sulfate, potassium sulfate, aluminum sulfate, potassium magnesium sulfate, sodium sulfate, calcium carbonate, sodium carbonate, magnesium silicate, potassium chloride, $LiAlH_4$, $NaAlH_4$, $iBu_2AlH$, metal methoxide, metal ethoxide, metal n-propoxide, metal isopropoxide, metal butoxide, metal 2-methylpropoxide, metal tert-butoxide, titanium isopropoxide, aluminum ethoxide, aluminum isopropoxide, zirconium ethoxide, and combinations thereof, n-butyl lithium, t-butyl lithium, sec-butyl lithium, triethyl aluminum, tributyl aluminum triisobutyl aluminum, triisopropyl aluminum, trioctyl aluminum, lithium diisopropyl amide, KHMDS, and the like, and combinations thereof.

In some embodiments, the first agent, second agent, third agent, and/or any additional agents used in accordance with the present teachings are each individually and optionally attached to a solid support. Representative solid supports for use in accordance with the present teachings include but are not limited to carbon, silica, silica-alumina, alumina, clay, magnesium silicates (e.g., Magnesols), the synthetic silica adsorbent sold under the trade name TRISYL by W. R. Grace & Co., diatomaceous earth, polystyrene, macroporous (MP) resins, and the like, and combinations thereof.

Typically, there are several choices of different and oftentimes complementary agents from which to choose when preparing to treat a contaminated substrate (e.g., natural oil feedstocks and the like) prior to a metathesis reaction. While neither desiring to be bound by any particular theory nor intending to limit in any measure the scope of the appended claims or their equivalents, it is presently believed that the following non-exhaustive and non-limiting list of representative treatment methodologies can be useful in treating substrates that contain the specified contaminants (provided the agents are compatible with any functional groups on the substrate and/or with the contaminants themselves, etc.):

(a) a thermal treatment—for example, heating (and/or distilling) a substrate (e.g., between about 100° C. and about 250° C., or around 200° C. in some embodiments—depending on the substrate's boiling point, optionally with a purge of an inert gas such as $N_2$ and/or the like) and/or treatment with an adsorbent (e.g., alumina and the like) can be useful in decomposing peroxide contaminants and/or decomposition products thereof;

(b) treatment with an acid anhydride (e.g., acetic anhydride, $Ac_2O$) can be useful in removing moisture, active hydroxyl-containing materials (e.g., alcohols), and hydroperoxides (via acetylation);

(c) treatment with a desiccant (e.g., silica gel, alumina, molecular sieves, magnesium sulfate, calcium sulfate, and the like, and combinations thereof) and/or an organometallic reagent (e.g., t-butyl lithium, triethyl aluminum, tributyl aluminum, triisobutyl aluminum, triisopropyl aluminum, trioctyl aluminum, and the like, and combinations thereof) and/or metal hydrides (e.g., $CaH_2$ and the like) and/or acid anhydrides (e.g., acetic anhydride and the like) can be useful in removing moisture;

(d) treatment with an adsorbent (e.g., alumina, silica gel, activated charcoal, and the like, and combinations thereof) and/or an organometallic reagent (e.g., t-butyl lithium, triethyl aluminum, tributyl aluminum, triisobutyl aluminum, triisopropyl aluminum, trioctyl aluminum, and the like, and combinations thereof) and/or a metal amide (e.g., LDA, KHMDA, and the like) can be useful in removing protic materials;

(e) treatment with an adsorbent (e.g., alumina, silica gel, activated charcoal, and the like, and combinations thereof) can be useful in removing polar materials; and/or (f) treatment with an organometallic reagent (e.g., t-butyl lithium, triethyl aluminum, tributyl aluminum, triisobutyl aluminum, triisopropyl aluminum, trioctyl aluminum, and the like, and combinations thereof) can be useful in removing Lewis basic catalyst poisons; etc.

In some embodiments, the first agent used to treat a substrate prior to a metathesis reaction comprises an adsorbent which, in some embodiments, is selected from the group consisting of silica gel, alumina, bleaching clay, activated carbon, molecular sieves, zeolites, fuller's earth, diatomaceous earth, and the like, and combinations thereof. In some embodiments, the first agent is selected from the group consisting of optionally heat-treated molecular sieves, optionally heat-treated alumina, and a combination thereof. In some embodiments, the adsorbent comprises optionally heat-treated activated alumina which, in some embodiments, is selected from the group consisting of optionally heat-treated activated acidic alumina, optionally heat-treated activated neutral alumina, optionally heat-treated activated basic alumina, and combinations thereof. In some embodiments, the absorbent comprises optionally heat-treated activated neutral alumina, which can be useful in treating substrates (e.g., olefins) that are susceptible to acid-catalyzed isomerization and/or rearrangement.

For embodiments in which the first agent, second agent, third agent, and/or any additional agents used in accordance with the present teachings comprises an adsorbent (e.g., molecular sieves, alumina, etc.), it is presently believed that the treating of the substrate with the adsorbent is more effectively performed by flowing the substrate through the first agent using a percolation- or flow-type system (e.g., chromatography column) as opposed to simply adding the adsorbent to the substrate in a container. In some embodiments, about 20 wt % of alumina is used in a column. While neither desiring to be bound by any particular theory nor intending to limit in any measure the scope of the appended claims or their equivalents, it is presently believed that treating a feedstock with alumina on about a 5-to-1 weight-to-weight basis is effective for some embodiments. However, it is to be understood that the amount of alumina used is not restricted and will be both feedstock- and impurity dependent in addition to being impacted by the form of the alumina, its activation process, and the precise treatment method (e.g., flow through a column vs. direct addition to container).

In some embodiments, the first agent, second agent, third agent, and/or any additional agents used to treat a substrate prior to a metathesis reaction comprises a trialkyl aluminum which, in some embodiments, is selected from the group consisting of triethyl aluminum, tributyl aluminum, triisobutyl aluminum, triisopropyl aluminum, trioctyl aluminum, and the like, and combinations thereof. While neither desiring to be bound by any particular theory nor intending to limit in any measure the scope of the appended claims or their equivalents, it is presently believed that the treatment of a substrate with a trialkyl aluminum greatly improves feedstock conversions at low concentrations of metathesis catalyst but that in the presence of excess trialkyl aluminum, catalyst performance is adversely affected. Thus, in some embodiments (e.g., when a trialkyl aluminum is used as a first agent and/or an excess of trialkyl aluminum is used), a successive agent used to treat the substrate can comprise an adsorbent which can remove excess trialkyl aluminum. In other embodiments, the amount of trialkyl aluminum used for treatment of the substrate can be reduced by first treating the substrate with a different agent of a type described herein (e.g., an adsorbent including but not limited to molecular sieves, alumina, and/or the like), and then introducing the trialkyl aluminum as a second (or subsequent) agent to remove residual contaminants. In any event, while neither desiring to be bound by any particular theory nor intending to limit in any measure the scope of the appended claims or their equivalents, it is presently believed that removal of excess trialkyl aluminum from organic products should be performed with great caution since use of the wrong adsorbent might be unsafe. In some embodiments, the trialkyl aluminum is attached to a solid support to simplify its removal.

In some embodiments, molecular sieves can be used as a first agent for bulk drying a substrate, "high heat-treated" alumina can then be used as a second agent to remove additional moisture, and finally molecular sieves can be used at the end as a third agent for removing still further residual moisture. In other embodiments, molecular sieves can be used as a first agent for bulk drying a substrate, "high heat-treated" alumina can then be used as a second agent to remove additional moisture, and finally a trialkyl aluminum (e.g., triethyl aluminum, tributyl aluminum, triisobutyl aluminum, triisopropyl aluminum, trioctyl aluminum, and the like, and combinations thereof) can be used as a third agent for removing any further residual moisture.

In one particular embodiment, activated copper powder is used alone or in combination with another treatment. For example, in some embodiments, activated copper powder is used in combination with heat (e.g., 200° C. for at least 2 hours under nitrogen gas), molecular sieves, and/or a trialkyl aluminum treatment. In another embodiment, activated magnesium turnings are used alone or in combination with another treatment. For example, in some embodiments, activated magnesium turnings are used in combination with heat (e.g., 200° C. for at least 2 hours under nitrogen gas), molecular sieves, and/or a trialkyl aluminum treatment.

In another particular embodiment, acetic anhydride is used alone or in combination with another treatment/agent. For example, in some embodiments, acetic anhydride is used in combination with alumina (aluminum oxide) and/or a trialkyl aluminum treatment. In other embodiments, acetic anhydride is used in combination with alumina, distillation, molecular sieves, and/or a trialkyl aluminum treatment. Further, percolation on activated alumina or molecular sieves can be applied before or instead of the trialkyl aluminum treatment.

In another embodiment, alumina is used alone or in combination with another treatment/agent. In one embodiment, alumina is used in combination with a palladium on carbon (Pd/C) catalyst and/or a trialkyl aluminum treatment.

In some embodiments, the treating of a substrate with a first agent reduces the level of the one or more contaminants by an amount sufficient to enable the metathesis reaction to proceed at a substrate-to-catalyst molar ratio of at least about 1,000 to 1, in some embodiments of at least about 2,500 to 1, in some embodiments of at least about 5,000 to 1, in some embodiments of at least about 7,500 to 1, in some embodiments at least about 10,000 to 1, in some embodiments at least about 15,000 to 1, in some embodiments at least about 20,000 to 1, in some embodiments at least about 25,000 to 1, in some embodiments at least about 30,000 to 1, in some embodiments at least about 35,000 to 1, in some embodiments at least about 40,000 to 1, in some embodiments at least about 45,000 to 1, and in some embodiments at least about 50,000 to 1.

In other embodiments, the treating of a substrate with a first agent reduces the level of the one or more contaminants by an amount sufficient to enable the metathesis reaction to proceed at a substrate-to-catalyst molar ratio as high as about 100,000 to 1, in some embodiments as high as about 500,000 to 1, in some embodiments as high as about 1,000,000 to 1, in some embodiments as high as about 2,000,000 to 1, in some embodiments as high as about 3,000,000 to 1, and in some embodiments as high as about 4,000,000 to 1.

In some embodiments, the metathesis reaction proceeds at a substrate-to-catalyst molar ratio between about 4,000,000:1 and 1,000:1, or between about 3,000,000:1 and 5,000:1, or between about 2,000,000:1 and 7,500:1, or between about 1,000,000:1 and 10,000:1, or between about 500,000:1 and 20,000:1, or between about 100,000:1 and 50,000:1.

In one embodiment, the treatment of the substrate reduces the level of the at least one contaminant by an amount sufficient to enable the metathesis reaction to proceed at substrate-to-catalyst molar ratio of at least 1,000:1, 2,500:1, 5,000:1, 7,500:1, 10,000:1, 15,000:1, 20,000:1, 25,000:1, 30,000:1, 35,000:1, 40,000:1, 45,000:1, 50,000:1, 100,000:1, 500,000:1, 1,000,000:1, or 2,000,000:1, and the corresponding conversion is at least 30%, or at least 40%, or at least 50%, or at least 60%, or at least 70%, or at least 80%, or at least 90%.

In other embodiments, the treatment of the substrate reduces the level of the at least one contaminant by an amount sufficient to enable the metathesis reaction to proceed at a substrate-to-catalyst molar ratio between 50,000:1 and 1,000:1, or between 40,000:1 and 2,500:1, or between 30,000:1 and 5,000:1, or between 25,000:1 and 7,500:1, or between 30,000:1 and 10,000:1, or between 30,000:1 and 15,000:1, and the corresponding conversion is between 30% and 100%, or between 50% and 100%, or between 60% to 100%.

In some embodiments, treating a substrate prior to a metathesis reaction with a first agent, second agent, third agent, and/or any additional agents in accordance with the present teachings reduces moisture contamination in the substrate to a level that is less than about 10 ppm, in some embodiments less than about 7 ppm, in some embodiments less than about 5 ppm, in some embodiments less than about 3 ppm, in some embodiments less than about 2 ppm, and in some embodiments less than about 1 ppm. In addition or alternatively, in some embodiments, treating a substrate prior to a metathesis reaction with a first agent, second agent, third agent, and/or any additional agents in accordance with the present teachings reduces peroxides to a level that is less than about 10 milliequivalents per kilogram, in some embodiments less than about 7 milliequivalents per kilogram, in some embodiments less than about 5 milliequivalents per kilogram, in some embodiments less than about 3 milliequivalents per kilogram, in some embodiments less than about 2 milliequivalents per kilogram, and in some embodiments less than about 1 milliequivalents per kilogram.

A method for metathesizing a substrate embodying features of the present invention includes treating the substrate with a first agent; and reacting the substrate, following its treatment with the first agent, in a metathesis reaction in the presence of a metathesis catalyst. The first agent is configured to mitigate potentially adverse effects of one or more contaminants in the substrate on the metathesis catalyst. In some embodiments, the substrate comprises a natural oil and/or a derivative thereof. In some embodiments, the treating reduces a level of the one or more contaminants by an amount sufficient to enable the metathesis reaction to proceed at a substrate-to-catalyst molar ratio of at least about 7,500 to 1, and, in some embodiments, as high as about 2,000,000 to 1.

The following examples and representative procedures illustrate features in accordance with the present teachings, and are provided solely by way of illustration. They are not intended to limit the scope of the appended claims or their equivalents.

EXAMPLES

Examples 1-15

Study of Various Substrate Treatments Prior to Ethenolysis of Natural Triglycerides Materials and Methods Edible grade soybean oil (Master Chef, designated 'SBO-1') and rapeseed oil (Canola oil, Cargill Solo, designated 'CO-1') were purchased in grocery store. Unless otherwise noted, the natural triglyceride used in the examples below was Canola oil.

Compounds X007, X008, and X022 refer to molybdenum and tungsten catalysts having the structures described in the detailed description part above.

Ethylene gas (5.0, impurities: methane, ethane) was obtained in cylinders from Messer Hungarogas Ltd. and was used without any further purification. Triethylaluminum (25% in toluene; Cat. #192708), trioctylaluminum (25% in n-hexane; Cat. #386553), acetic anhydride (ACS reagent, Cat. #242845), Cu powder (Cat. #12806) and Mg turnings (Cat. #403148) were purchased from Sigma-Aldrich. The surface of copper powder was activated by following the procedure described in Organic Reactions Vol. 63: Cu, Ni and Pd Mediated Homocoupling reactions in biaryl syntheses: The Ullmann Reaction (Viley, DOI: 10.1002/0471264180). For the activation of the surface of magnesium turnings Grignard reaction in diethyl ether with 1,2-dibromoethane was started then the activated magnesium turnings were isolated by filtration, washing with dry diethyl ether and drying under dry nitrogen atmosphere. Moleculer sieves (3 Å, beads, ~2 mm; Cat. #1.05704.1000), molecular sieves (3 Å, powder; Cat. #1.05706.0250), aluminum oxide (basic, 0.063-0.200 mm; Cat. #1.01076.2000) were purchased from Merck. For activation molecular sieves & alumina were heated at 300° C. under 1 mbar for 24 hours and let cool and stored under dry nitrogen atmosphere. Pd/C (10%, Selkat-Q-6) was purchased from Szilor Kft., Hungary. Peroxide value [milliequivalents peroxide/kg of sample (meq/kg)] was determined through titration utilizing an autotitrator (Metrohm 888 Titrando). Moisture content was determined by Metrohm 899 Coulometer Karl Fischer titration apparatus. Para-Anisidine value (pAV) was determined according to AOCS Official Method Cd 18-90.

Studies were conducted on natural triglyceride samples (e.g., canola oil or soybean oil) for various substrate treatment methods to create a rating system suitable for comparison of their performance. The performance of the treatment method was described by the outcome of the ethenolysis reaction performed on the treated oil samples. Conversion % and MD9 yield % values were compared, along with selectivity % and 9ODDAME yield %.

In certain tests (designated 'A'), substrate samples were treated and then subjected to ethenolysis using different amounts of molybdenum- or tungsten-based catalysts (i.e., X007, X008, and X022). In comparable testing (designated 'B'), the substrate samples were treated and then subjected to a secondary treatment with different amounts of a trialkyl aluminum (e.g., triethylaluminum, trioctylaluminum), and then subjected to ethenolysis (at 250 ppmwt of X022) to determine how the trialkyl aluminum demand decreased. In these tests, the trialkyl aluminum treatment was performed for four hours and no time dependency was examined. However in later examples it is shown that the success of trialkyl aluminum treatment depends on reaction time. Furthermore, in experiments 'B' additional tests were performed using other treatments prior to or in replacement of a trialkyl aluminum treatment of the substrate. Table 1, shown below, outlines the various tests conducted in Examples 1-15. Unless otherwise indicated, canola oil was used as the substrate.

TABLE 1

Overview of testing conditions for Examples 1-15

| Ex. # | Treatment | 'A'-Ethenolysis Conditions | 'B'-Trialkyl aluminum Treatment (w/ 250 ppmwt X022) |
|---|---|---|---|
| 1 | None | 10, 7, 4, 1, 0.5 mol % of X008<br>10, 7, 4, 1, 0.5 mol % of X022 | 0, 1, 2, 3, 4, 5, 6, 7, 8, 9 mol % $Et_3Al$<br>4, 5, 6 mol % $Oc_3Al$ |
| 2 | Drying by Mol. Sieves | 7, 4, 1 mol % of X008 | 1, 2, 3, 4, 5, 6 mol % $Et_3Al$ |
| 3 | Heating at 200° C. under $N_2$ for 2 h. | 7, 4, 1 mol % of X008 | 2, 3, 4, 5 mol % $Oc_3Al$ |
| 4 | Distillation treatment | 7, 4, 1 mol % of X008 | 2, 3, 4, 5 mol % $Oc_3Al$ |
| 5 | Cu/r.t. | 7, 4, 1 mol % of X008<br>2500, 1000, 250 ppmwt of X022 | 2, 3, 4, 5 mol % $Oc_3Al$ |
| 6 | Cu/200° C. | 7, 4, 1, 0.5 mol % of X008<br>7, 4, 1, 0.5 mol % X022;<br>2000, 1000, 250 ppmwt of X022 | 2, 3, 4, 5 mol % $Oc_3Al$ |
| 7 | Cu/200° C. + mol. sieves | 7, 4, 1 mol % of X008 | 2, 3, 4, 5 mol % $Oc_3Al$ |
| 8 | Mg/r.t. | 7, 4, 1 mol % of X008<br>2000, 1000, 250 ppmwt of X022 | 2, 3, 4, 5 mol % $Oc_3Al$ |
| 9 | Mg/200° C. | 7, 4, 1 mol % of X008 | 2, 3, 4, 5 mol % $Oc_3Al$ |
| 10 | $Ac_2O$ | 2000, 1500, 1000, 500 ppmwt of X008 | 0.2, 0.5, 1, 2, 3, 4 mol % $Oc_3Al$ |
| 11 | $Ac_2O + Al_2O_3$ * | 1000, 750, 500 ppmwt of X008<br>0.2, 0.1, 0.06 mol % X007 | 0.5, 1, 2, 3 mol % $Oc_3Al$ |
| 12 | $Al_2O_3$, Pd/C – 100° C., $Ac_2O$ * | 1000, 750, 500 ppmwt of X008 | 0.5, 1, 2, 3 mol % $Oc_3Al$ |
| 13 | Distillation, $Ac_2O$, $Al_2O_3$ | 500 ppmwt of X008 | —** |
| 14 | Distillation, $Ac_2O$, mol. Sieves, $Al_2O_3$ | 1000, 750, 500 ppmwt of X008 | 0.5, 1, 2, 3 mol % $Oc_3Al$ |
| 15 | Distillation, $Ac_2O$, $Al_2O_3$, percolation (mol. sieves + $Al_2O_3$) | 1000, 750, 500 ppmwt of X008 | 0, 0.1, 0.2, 0.5, 1, 2, 3, 4 mol % $Oc_3Al$ |

* Soybean oil used as the substrate
** not performed due to lack of substrate

Examples 1(a) and 1(b)

Example 1(a)

Canola oil (CO-1) samples were placed in glass vials into a 850 ml stainless steel autoclave and were subjected to ethenolysis under 10 atm of ethylene gas at 50° C. for 18 hours using the given amounts of catalyst X008 or X022. After ethenolysis, the reaction mixtures were subjected to Zemplen's transesterification (NaOMe/MeOH; rt, 3 h) and were analyzed by GCMS using pentadecane as internal standard. The tests are outlined in Table 2, shown below.

TABLE 2

| Ex. | Reaction | Lot | Catalyst | mol % | Scale |
|---|---|---|---|---|---|
| 1(a) | CO-1 to FAME mix ethenolysis | E01JVA715 | X008 | 10 | 0.1 ml (0.1 mmol) |
| | | E01JVA716 | | 7 | |
| | | E01JVA717 | | 4 | |
| | | E01JVA722 | | 1 | |
| | | E01JVA723 | | 0.5 | |
| | | E01JVA718 | X022 | 10 | |
| | | E01JVA719 | | 7 | |
| | | E01JVA720 | | 4 | |
| | | E01JVA724 | | 1 | |
| | | E01JVA725 | | 0.5 | |

Example 1(b)

Canola oil (CO-1) samples were stirred in glass vials with the given amounts of trialkyl aluminum under dry nitrogen atmosphere at room temperature for 4 hours. The vials with the reaction mixtures were placed into a 850 ml stainless steel autoclave and the mixtures were subjected to ethenolysis under 10 atm of ethylene gas at 50° C. for 18 hours using 250 ppmwt of catalyst X022. After ethenolysis, the reaction mixtures were subjected to Zemplen's transesterification (NaOMe/MeOH; rt, 3 h) and were analyzed by GCMS using pentadecane as internal standard. The tests are outlined in Table 3, shown below.

TABLE 3

| Ex. | Reaction | Lot | Et3Al, Oc3Al mol % | Catalyst | Scale |
|---|---|---|---|---|---|
| 1(b) | CO-1 to FAME mix Et$_3$Al or Oc$_3$Al treatment, ethenolysis | E01JVA609 | 0% Et$_3$Al | 250 ppmwt X022 | 0.1 ml (0.1 mmol) |
| | | E01JVA610 | 1% Et$_3$Al | | |
| | | E01JVA611 | 2% Et$_3$Al | | |
| | | E01JVA612 | 3% Et$_3$Al | | |
| | | E01JVA613 | 4% Et$_3$Al | | |
| | | E01JVA614 | 5% Et$_3$Al | | |
| | | E01JVA615 | 6% Et$_3$Al | | |
| | | E01JVA616 | 7% Et$_3$Al | | |
| | | E01JVA617 | 8% Et$_3$Al | | |
| | | E01JVA618 | 9% Et$_3$Al | | |
| | | E01JVA683 | 4% Oc$_3$Al | | 0.8 ml (0.8 mmol) |
| | | E01JVA684a | 5% Oc$_3$Al | | |
| | | E01JVA685 | 6% Oc$_3$Al | | |

Examples 2(a) and 2(b)

Example 2(a)

In a nitrogen filled glove box, commercial grade rapeseed oil (Canola oil CO-1, 200 ml, 180.24 g, water content: 9 ppm) was stirred with molecular sieves (beads, 3 Å, activated, 25.4 g) at room temperature for 6 days. The substrate was filtered on activated celite pad giving batch E01JVA640. Water content: 3 ppm. Samples from the treated substrate were then placed in glass vials into a 850 ml stainless steel autoclave and were subjected to ethenolysis under 10 atm of ethylene gas at 50° C. for 18 hours using the given amounts of catalyst X008. After Zemplen's transesterification (NaOMe/MeOH; rt, 3 h) GCMS analysis was performed. The tests are outlined in Table 4, shown below.

TABLE 4

| Ex. | Reaction | Lot | Catalyst | mol % | Scale |
|---|---|---|---|---|---|
| 2(a) | E01JVA640 to FAME mix ethenolysis | E01JVA740 | X008 | 7 | 0.1 ml (0.1 mmol) |
| | | E01JVA741 | | 4 | |
| | | E01JVA742 | | 1 | |

Example 2(b)

In a nitrogen filled glove box, commercial grade rapeseed oil (Canola oil CO-1, 200 ml, 180.24 g, water content: 9 ppm) was stirred with molecular sieves (beads, 3 Å, activated, 25.4 g) at room temperature for 6 days. The substrate was filtered on activated celite pad giving batch E01JVA640. Water content: 3 ppm. Samples from E01JVA640 were placed in glass vials and stirred with the given amounts of triethylaluminum under dry nitrogen atmosphere at room temperature for 4 hours. The vials with the reaction mixtures were placed into a 850 ml stainless steel autoclave and the mixtures were subjected to ethenolysis under 10 atm of ethylene gas at 50° C. for 18 hours using 250 ppmwt of catalyst X022. After ethenolysis, the reaction mixtures were subjected to Zemplen's transesterification (NaOMe/MeOH; rt, 3 h) and were analyzed by GCMS using pentadecane as internal standard. The tests are outlined in Table 5, shown below.

TABLE 5

| Ex. | Reaction | Lot | Et3Al, Oc3Al mol % | Catalyst | Scale |
|---|---|---|---|---|---|
| 2(b) | E01JVA640 to FAME mix Et$_3$Al treatment, ethenolysis | E01JVA641a | 1% Et$_3$Al | 250 ppmwt X022 | 1.8 ml (1.9 mmol) |
| | | E01JVA642a | 2% Et$_3$Al | | |
| | | E01JVA643a | 3% Et$_3$Al | | |
| | | E01JVA644a | 4% Et$_3$Al | | |
| | | E01JVA645a | 5% Et$_3$Al | | |
| | | E01JVA646a | 6% Et$_3$Al | | |

Examples 3(a) and 3(b)

Example 3(a)

In a nitrogen gas filled glove box, commercial grade Canola oil (CO-1, 1.3 ml) was stirred at 200° C. for 2 hours. Cooling to room temperature gave E01JVA752. Sample from E01JVA752 were then placed in glass vials into a 850 ml stainless steel autoclave and were subjected to ethenolysis under 10 atm of ethylene gas at 50° C. for 18 hours using the given amounts of catalyst X008. After Zemplen's transesterification (NaOMe/MeOH; rt, 3 h) GCMS analysis was performed. The tests are outlined in Table 6, shown below.

TABLE 6

| Ex. | Reaction | Lot | Catalyst | mol % | Scale |
|---|---|---|---|---|---|
| 3(a) | E01JVA752 to FAME mix ethenolysis | E01JVA743 | X008 | 7 | 0.1 ml (0.1 mmol) |
| | | E01JVA744 | | 4 | |
| | | E01JVA745 | | 1 | |

Example 3(b)

In a nitrogen gas filled glove box, commercial grade Canola oil (CO-1, 1.3 ml) was stirred at 200° C. for 2 hours. Cooling to room temperature gave E01JVA752. Then, in a nitrogen gas filled glove box, samples from E01JVA752 were stirred in glass vials with the given amount of $Oc_3Al$ (25 wt % in hexane) at room temperature for 4 hours. The vials were then placed into a 850 ml stainless steel autoclave and the reaction mixtures were subjected to ethenolysis under 10 atm of ethylene gas at 50° C. for 18 hours using 250 ppmwt of catalyst X022. After Zemplen's transesterification (NaOMe/MeOH; rt, 3 h) GCMS analysis was performed. The tests are outlined in Table 7, shown below.

TABLE 7

| Ex. | Reaction | Lot | $Oc_3Al$ mol % | Catalyst | Scale |
|---|---|---|---|---|---|
| 3b | E01JVA752 to FAME mix $Oc_3Al$ treatment & ethenolysis | E01JVA765 E01JVA766 E01JVA767 E01JVA768 | 2 3 4 5 | 250 ppmwt X022 | 0.8 ml (0.83 mmol) |

Examples 4(a) and 4(b)

Example 4(a)

Commercial grade Canola oil (CO-1) was subjected to vacuum distillation in a short way distillation apparatus in a 280° C. oil bath under 0.5 mbar for 5 hours, while a continuous slow nitrogen flow was let through the oil to purge out the volatile components. The residue of the distillation treatment (E01JVA721) was transferred into a nitrogen gas filled glove box. Samples from E01JVA721 in glass vials were placed into a 850 ml stainless steel autoclave and were subjected to ethenolysis under 10 atm of ethylene gas at 50° C. for 18 hours using the given amounts of catalyst X008. After Zemplen's transesterification (NaOMe/MeOH; rt, 3 h) GCMS analysis was performed. The tests are outlined in Table 8, shown below.

TABLE 8

| Ex. | Reaction | Lot | Catalyst | mol % | Scale |
|---|---|---|---|---|---|
| 4(a) | E01JVA721 to FAME mix ethenolysis | E01JVA734 E01JVA735 E01JVA736 | X008 | 7 4 1 | 0.1 ml (0.1 mmol) |

Example 4(b)

Commercial grade Canola oil (CO-1) was subjected to vacuum distillation in a short way distillation apparatus in a 280° C. oil bath under 0.5 mbar vacuum for 5 hours, while a continuous slow nitrogen flow was let through the oil to purge out the volatile components. The residue of the distillation treatment was transferred into a nitrogen gas filled glove box (E01JVA721). Samples from E01JVA721 were stirred in glass vials with the given amount of $Oc_3Al$ (25 wt % in hexane) at room temperature for 4 hours. The vials were then placed into a 850 ml stainless steel autoclave and the reaction mixtures were subjected to ethenolysis under 10 atm of ethylene gas at 50° C. for 18 hours using 250 ppmwt of catalyst X022. After Zemplen's transesterification (NaOMe/MeOH; rt, 3 h) GCMS analysis was performed. The tests are outlined in Table 9, shown below.

TABLE 9

| Ex. | Reaction | Lot | $Oc_3Al$ mol % | Catalyst | Scale |
|---|---|---|---|---|---|
| 4(b) | E01JVA721 to FAME mix $Oc_3Al$ treatment & ethenolysis | E01JVA753 E01JVA754 E01JVA755 E01JVA756 | 2 3 4 5 | 250 ppmwt X022 | 0.8 ml (0.83 mmol) |

Examples 5(a) and 5(b)

Example 5(a)

In a nitrogen gas filled glove box, commercial grade Canola oil (CO-1, 21 ml) was stirred with activated copper powder (3.35 g) at room temperature for 114 hours. Filtration on Whatman AutoCup (0.45 μm PTFE) by suction gave E01JVA630. Samples from E01JVA630 were placed in glass vials into a 850 ml stainless steel autoclave and were subjected to ethenolysis under 10 atm of ethylene gas at 50° C. for 18 hours using the given amounts of catalyst X008 or X022. After Zemplen's transesterification (NaOMe/MeOH; rt, 3 h) GCMS analysis was performed. The tests are outlined in Table 10, shown below.

TABLE 10

| Ex. | Reaction | Lot | Catalyst | Cat. amt. | Scale |
|---|---|---|---|---|---|
| 5(a) | E01JVA630 to FAME mix ethenolysis | E01JVA737 E01JVA738 E01JVA739 | X008 in mol % | 7 4 1 | 0.1 ml (0.1 mmol) |
| 4(a) | E01JVA721 to FAME mix ethenolysis | E01JVA643 E01JVA644 E01JVA645 | X022 in pptwt % | 2500 1000 250 | 1.7 g (1.9 mmol) |

Example 5(b)

In a nitrogen gas filled glove box, commercial grade Canola oil (CO-1, 21 ml) was stirred with activated copper powder (3.35 g) at room temperature for 114 hours. Filtration on Whatman AutoCup (0.45 μm PTFE) by suction gave E01JVA630. Samples from E01JVA630 were placed in glass vials and were stirred with the given amount of $Oc_3Al$ (25 wt % in hexane) at room temperature for 4 hours. The vials were then placed into a 850 ml stainless steel autoclave and the reaction mixtures were subjected to ethenolysis under 10 atm of ethylene gas at 50° C. for 18 hours using 250 ppmwt of catalyst X022. After Zemplen's transesterification (NaOMe/MeOH; rt, 3 h) GCMS analysis was performed. The tests are outlined in Table 11, shown below.

TABLE 11

| Ex. | Reaction | Lot | $Oc_3Al$ mol % | Catalyst | Scale |
|---|---|---|---|---|---|
| 5b | E01JVA630 to FAME mix $Oc_3Al$ treatment & ethenolysis | E01JVA757 E01JVA758 E01JVA759 E01JVA760 | 2 3 4 5 | 250 ppmwt X022 | 0.8 ml (0.83 mmol) |

Examples 6(a) and 6(b)

Example 6(a)

In a nitrogen filled glove box commercial grade Canola oil (CO-1, 21 g, 24 mmol) was stirred with activated copper powder (3.3 g, 52 mmol) at 200° C. for 2 hours. After cooling back to room temperature, filtration on Whatman AutoCup (0.45 μm PTFE) by suction gave E01JVA701B. Samples from E01JVA701B were placed in glass vials into a 850 ml stainless steel autoclave and were subjected to ethenolysis under 10 atm of ethylene gas at 50° C. for 18 hours using the given amounts of catalyst X008 or X022. After Zemplen's transesterification (NaOMe/MeOH; rt, 3 h) GCMS analysis was performed. The tests are outlined in Table 12, shown below.

TABLE 12

| Ex. | Reaction | Lot | Catalyst | Cat. amt. | Scale |
|---|---|---|---|---|---|
| 6(a) | E01JVA701B to FAME mix ethenolysis | E01JVA726 | X008 in mol % | 7 | 0.1 ml (0.1 mmol) |
| | | E01JVA727 | | 4 | |
| | | E01JVA728 | | 1 | |
| | | E01JVA732 | | 0.5 | |
| | | E01JVA729 | X022 in mol % | 7 | |
| | | E01JVA730 | | 4 | |
| | | E01JVA731 | | 1 | |
| | | E01JVA733 | | 0.5 | |
| | | E01JVA703 | X022 in ppmwt | 2500 | 0.67 g (0.77 mmol) |
| | | E01JVA704 | | 1000 | |
| | | E01JVA705 | | 250 | |

Example 6(b)

In a nitrogen filled glove box commercial grade Canola oil (CO-1, 21 g, 24 mmol) was stirred with activated copper powder (3.3 g, 52 mmol) at 200° C. for 2 hours. After cooling back to room temperature, filtration on Whatman AutoCup (0.45 μm PTFE) by suction gave E01JVA701B. Samples from E01JVA701B were placed in glass vials and stirred with the given amount of $Oc_3Al$ (25 wt % in hexane) at room temperature for 4 hours. The vials were then placed into a 850 ml stainless steel autoclave and the reaction mixtures were subjected to ethenolysis under 10 atm of ethylene gas at 50° C. for 18 hours using 250 ppmwt of catalyst X022. After Zemplen's transesterification (NaOMe/MeOH; rt, 3 h) GCMS analysis was performed. The tests are outlined in Table 13, shown below.

TABLE 13

| Ex. | Reaction | Lot | $Oc_3Al$ mol % | Catalyst | Scale |
|---|---|---|---|---|---|
| 6(b) | E01JVA701B to FAME mix $Oc_3Al$ treatment & ethenolysis | E01JVA761 | 2 | 250 ppmwt X022 | 0.8 ml (0.83 mmol) |
| | | E01JVA762 | 3 | | |
| | | E01JVA763 | 4 | | |
| | | E01JVA764 | 5 | | |

Examples 7(a) and 7(b)

Example 7(a)

In a nitrogen gas filled glove box, Cu/200° C. treated CO-1 sample (E01JVA701B from Examples 6(a) and (b), 9.909 g) was stirred with activated molecular sieves beads (3 Å, 5.927 g) at room temperature for 18 hours. Filtration on Whatman AutoCup (0.45 μm PTFE) by suction gave E01JVA701C. Samples from E01JVA701C were placed in glass vials into a 850 ml stainless steel autoclave and were subjected to ethenolysis under 10 atm of ethylene gas at 50° C. for 18 hours using the given amounts of catalyst X008. After Zemplen's transesterification (NaOMe/MeOH; rt, 3 h) GCMS analysis was performed. The tests are outlined in Table 14, shown below.

TABLE 14

| Ex. | Reaction | Lot | Catalyst | mol % | Scale |
|---|---|---|---|---|---|
| 7(a) | E01JVA701C to FAME mix ethenolysis | E01JVA746 | X008 | 7 | 0.1 ml (0.1 mmol) |
| | | E01JVA747 | | 4 | |
| | | E01JVA748 | | 1 | |

Example 7(b)

In a nitrogen gas filled glove box, Cu/200° C. treated CO-1 sample (E01JVA701B from Examples 6(a) and (b), 9.909 g) was stirred with activated molecular sieves beads (3 Å, 5.927 g) at room temperature for 18 hours. Filtration on Whatman AutoCup (0.45 μm PTFE) by suction gave E01JVA701C. Samples from E01JVA701C were placed in glass vials and stirred with the given amount of $Oc_3Al$ (25 wt % in hexane) at room temperature for 4 hours. The vials were then placed into a 850 ml stainless steel autoclave and the reaction mixtures were subjected to ethenolysis under 10 atm of ethylene gas at 50° C. for 18 hours using 250 ppmwt of catalyst X022. After Zemplen's transesterification (NaOMe/MeOH; rt, 3 h) GCMS analysis was performed. The tests are outlined in Table 15, shown below.

TABLE 15

| Ex. | Reaction | Lot | $Oc_3Al$ mol % | Catalyst | Scale |
|---|---|---|---|---|---|
| 7b | E01JVA701C to FAME mix Oc3Al treatment & ethenolysis | E01JVA769 | 2 | 250 ppmwt X022 | 0.8 ml (0.83 mmol) |
| | | E01JVA770 | 3 | | |
| | | E01JVA771 | 4 | | |
| | | E01JVA772 | 5 | | |

Examples 8(a) and 8(b)

Example 8(a)

In a nitrogen gas filled glove box, commercial grade Canola oil (CO-1, 21 ml) was stirred with activated magnesium turnings (4.49 g) at room temperature for 14 days. Filtration on Whatman AutoCup (0.45 μm PTFE) by suction gave E01JVA632. Samples from E01JVA632 were placed in glass vials into a 850 ml stainless steel autoclave and were subjected to ethenolysis under 10 atm of ethylene gas at 50° C. for 18 hours using the given amounts of catalyst X008 or X022. After Zemplen's transesterification (NaOMe/MeOH; rt, 3 h) GCMS analysis was performed. The tests are outlined in Table 16, shown below.

TABLE 16

| Ex. | Reaction | Lot | Catalyst | Cat. amt. | Scale |
|---|---|---|---|---|---|
| 8(a) | E01JVA632 to FAME mix ethenolysis | E01JVA749 | X008 in mol % | 7 | 0.1 ml (0.1 mmol) |
| | | E01JVA750 | | 4 | |
| | | E01JVA751 | | 1 | |
| 4(a) | E01JVA721 to FAME mix ethenolysis | E01JVA671 | X022 in pptwt % | 2500 | 0.77 g (0.9 mmol) |
| | | E01JVA672 | | 1000 | |
| | | E01JVA673 | | 250 | |

Example 8(b)

In a nitrogen gas filled glove box, commercial grade Canola oil (CO-1, 21 ml) was stirred with activated magnesium turnings (4.49 g) at room temperature for 14 days. Filtration on Whatman AutoCup (0.45 μm PTFE) by suction gave E01JVA632. Samples from E01JVA632 were placed in glass vials and stirred with the given amount of $Oc_3Al$ (25 wt % in hexane) at room temperature for 4 hours. The vials were then placed into a 850 ml stainless steel autoclave and were subjected to ethenolysis under 10 atm of ethylene gas at 50° C. for 18 hours using 250 ppmwt of catalyst X022. After Zemplen's transesterification (NaOMe/MeOH; rt, 3 h) GCMS analysis was performed. The tests are outlined in Table 17, shown below.

TABLE 17

| Ex. | Reaction | Lot | $Oc_3Al$ mol % | Catalyst | Scale |
|---|---|---|---|---|---|
| 8(b) | E01JVA632 to FAME mix $Oc_3Al$ treatment & ethenolysis | E01JVA773 E01JVA774 E01JVA775 E01JVA776 | 2 3 4 5 | 250 ppmwt X022 | 0.8 ml (0.83 mmol) |

Examples 9(a) and 9(b)

Example 9(a)

In a nitrogen gas filled glove box, commercial grade Canola oil (CO-1, 21 ml) was stirred with activated magnesium turnings (4.49 g) at room temperature for 14 days. Filtration on Whatman AutoCup (0.45 μm PTFE) by suction gave E01JVA777. Samples from E01JVA777 were placed in glass vials into a 850 ml stainless steel autoclave and were subjected to ethenolysis under 10 atm of ethylene gas at 50° C. for 18 hours using the given amounts of catalyst X008. After Zemplen's transesterification (NaOMe/MeOH; rt, 3 h) GCMS analysis was performed. The tests are outlined in Table 18, shown below.

TABLE 18

| Ex. | Reaction | Lot | Catalyst | mol % | Scale |
|---|---|---|---|---|---|
| 9(a) | E01JVA777 to FAME mix ethenolysis | E01JVA781 E01JVA782 E01JVA783 | X008 | 7 4 1 | 0.1 ml (0.1 mmol) |

Example 9(b)

In a nitrogen gas filled glove box, commercial grade Canola oil (CO-1, 21 ml) was stirred with activated magnesium turnings (4.49 g) at room temperature for 14 days. Filtration on Whatman AutoCup (0.45 μm PTFE) by suction gave E01JVA777. Samples from E01JVA777 were placed in glass vials and stirred with the given amount of $Oc_3Al$ (25 wt % in hexane) at room temperature for 4 hours. The vials were then placed into a 850 ml stainless steel autoclave and the reaction mixtures were subjected to ethenolysis under 10 atm of ethylene gas at 50° C. for 18 hours using 250 ppmwt of catalyst X022. After Zemplen's transesterification (NaOMe/MeOH; rt, 3 h) GCMS analysis was performed. The tests are outlined in Table 19, shown below.

TABLE 19

| Ex. | Reaction | Lot | $Oc_3Al$ mol % | Catalyst | Scale |
|---|---|---|---|---|---|
| 9(b) | E01JVA777 to FAME mix $Oc_3Al$ treatment & ethenolysis | E01JVA784 E01JVA785 E01JVA786 E01JVA787 | 2 3 4 5 | 250 ppmwt X022 | 0.8 ml (0.83 mmol) |

Examples 10(a) and 10(b)

Example 10(a)

In a nitrogen gas filled glove box canola oil (CO-1, 500 ml) was stirred with acetic anhydride (15 ml, 30 mol %) at 110° C. internal temperature for 18 hours. The $Ac_2O$ excess and volatile products were distilled out at the same internal temperature with the aim of a membrane pump (17 mbar) while a constant slow nitrogen flow was bubbled through the oil for 5 hours. PV was below the detection limit. E01JVA808 was isolated by sucking the distillation residue out from the distilling flask via a stainless steel needle taking care to avoid the mixing of the oil with the small drops on the internal wall of the distilling flask. Samples from E01JVA808 were placed in glass vials into a 850 ml stainless steel autoclave and were subjected to ethenolysis under 10 atm of ethylene gas at 50° C. for 18 hours using the given amounts of catalyst X008. After Zemplen's transesterification (NaOMe/MeOH; rt, 3 h) GCMS analysis was performed. The tests are outlined in Table 20, shown below.

TABLE 20

| Ex. | Reaction | Lot | Catalyst | mol % | Scale |
|---|---|---|---|---|---|
| 10(a) | E01JVA808 to FAME mix ethenolysis | E01JVA809 E01JVA810 E01JVA811 E01JVA812 | X008 | 2000 1500 1000 500 | 0.8 ml (0.8 mmol) |

Example 10(b)

In a nitrogen gas filled glove box canola oil (CO-1, 500 ml) was stirred with acetic anhydride (15 ml, 30 mol %) at 110° C. internal temperature for 18 hours. The $Ac_2O$ excess and volatile products were distilled out at the same internal temperature with the aim of a membrane pump (17 mbar) while a constant slow nitrogen flow was bubbled through the oil for 5 hours. PV was below the detection limit. E01JVA808 was isolated by sucking the distillation residue out from the distilling flask via a stainless steel needle taking care to avoid the mixing of the oil with the small drops on the internal wall of the distilling flask. Samples from E01JVA808 were placed in glass vials and stirred with the given amount of $Oc_3Al$ (25 wt % in hexane) at room temperature for 4 hours. The vials were then placed into a 850 ml stainless steel autoclave and the reaction mixtures were subjected to ethenolysis under 10 atm of ethylene gas at 50° C. for 18 hours using 250 ppmwt of catalyst X022. After Zemplen's transesterification (NaOMe/MeOH; rt, 3 h) GCMS analysis was performed. The tests are outlined in Table 21, shown below.

TABLE 21

| Ex. | Reaction | Lot | Oc$_3$Al mol % | Catalyst | Scale |
|---|---|---|---|---|---|
| 10(b) | E01JVA808 to FAME mix Oc$_3$Al treatment & ethenolysis | E01JVA815 E01JVA816 E01JVA817 E01JVA818 E01JVA819 E01JVA820 | 0.2 0.5 1 2 3 4 | 250 ppmwt X022 | 0.8 ml (0.83 mmol) |

Examples 11(a) and 11(b)

Example 11(a)

In a nitrogen gas filled glove box soybean oil (SBO-1, 150 ml) was mixed with 30 mol % acetic anhydride ('Ac$_2$O', 5 ml) and the mixture was stirred at 110° C. internal temperature under nitrogen atmosphere for 18 hours. The initial PV=0.73 went down below detection limit. The Ac$_2$O excess and volatile byproducts were distilled out at reduced pressure (17 mbar) while a constant slow nitrogen flow was bubbled through the oil to help remove the volatile components for 5 hours. E01JVA168A was isolated by sucking the distillation residue out from the distilling flask via a stainless steel needle taking care to avoid the mixing of the oil with the small drops on the internal wall of the distilling flask. E01JVA168A (140 ml) was mixed with activated gamma-aluminum oxide (Brockman I., 5 g/100 ml) and the mixture was stirred under nitrogen atmosphere at room temperature for 96 hours. Filtration on celite pad gave E01JVA168B. Samples from E01JVA168B were placed in glass vials into a 850 ml stainless steel autoclave and were subjected to ethenolysis under 10 atm of ethylene gas at 50° C. for 18 hours using the given amounts of catalyst X008 or X007. After Zemplen's transesterification (NaOMe/MeOH; rt, 3 h) GCMS analysis was performed. The tests are outlined in Table 22, shown below.

TABLE 22

| Ex. | Reaction | Lot | Catalyst | Cat. amt. | Scale |
|---|---|---|---|---|---|
| 11(a) | E01JVA168B to FAME mix ethenolysis | E01JVA778 E01JVA779 E01JVA780 E01JVA181 E01JVA182 E01JVA183 | X008 in ppmwt X007 in mol % | 1000 750 500 0.2 0.1 0.06 | 0.1 ml (0.1 mmol) 0.77 g (0.9 mmol) |

Example 11(b)

In a nitrogen gas filled glove box soybean oil (SBO-1, 150 ml) was mixed with 30 mol % acetic anhydride ('Ac$_2$O', 5 ml) and the mixture was stirred at 110° C. internal temperature under nitrogen atmosphere for 18 hours. The initial PV=0.73 went down below detection limit. The Ac$_2$O excess and volatile byproducts were distilled out at reduced pressure (17 mbar) while a constant slow nitrogen flow was bubbled through the oil to help remove the volatile components for 5 hours. E01JVA168A was isolated by sucking the distillation residue out from the distilling flask via a stainless steel needle taking care to avoid the mixing of the oil with the small drops on the internal wall of the distilling flask. E01JVA168A (140 ml) was mixed with activated gamma-aluminum oxide (Brockman I., 5 g/100 ml) and the mixture was stirred under nitrogen atmosphere at room temperature for 96 hours. Filtration on celite pad gave E01JVA168B. Samples from E01JVA168B were placed in glass vials and stirred with the given amount of Oc$_3$Al (25 wt % in hexane) at room temperature for 4 hours. The vials were then placed into a 850 ml stainless steel autoclave and the reaction mixtures were subjected to ethenolysis under 10 atm of ethylene gas at 50° C. for 18 hours using 250 ppmwt of catalyst X022. After Zemplen's transesterification (NaOMe/MeOH; rt, 3 h) GCMS analysis was performed. The tests are outlined in Table 23, shown below.

TABLE 23

| Ex. | Reaction | Lot | Oc$_3$Al mol % | Catalyst | Scale |
|---|---|---|---|---|---|
| 11(b) | E01JVA168B to FAME mix Oc$_3$Al treatment & ethenolysis | E01JVA796 E01JVA797 E01JVA798 E01JVA799 | 0.5 1 2 3 | 250 ppmwt X022 | 0.8 ml (0.83 mmol) |

Examples 12(a) and 12(b)

Example 12(a)

In a nitrogen gas filled glove box, SBO-1 (500 ml) was mixed with activated gamma-aluminum oxide (Brockman I., 5 g/100 ml) and the mixture was stirred at room temperature for 21 hours. Filtration gave E01JVA161A. (The initial PV=0.73 went down to PV=0.09.) E01JVA161A was mixed with Selcat-Q-6 10% Pd/C (0.25 g/100 ml) and charcoal (1 g/100 ml) and was stirred at 110° C. (internal temperature) while the glove-box's nitrogen atmosphere was bubbled through it. After 2 h the PV was under the detection limit. After 13 h, filtration on Whatman AutoCup (0.45 μm PTFE) by suction gave E01JVA161C. E01JVA161C was mixed with Ac$_2$O (30 mol %) under nitrogen atmosphere at room temperature. The mixture was stirred at 110° C. (internal) for 18 hours, then the excess of the reagent and byproducts were distilled off under reduced pressure (17 mbar) while a constant nitrogen stream was bubbled through the oil slowly to help remove the volatile compounds. After 5 hours of distillation E01JVA161H was isolated by sucking out the distillation residue via a stainless steel needle taking care to avoid the mixing of the oil with the small drops on the internal wall of the distilling flask. Samples from E01JVA161H were placed in glass vials into a 850 ml stainless steel autoclave and were subjected to ethenolysis under 10 atm of ethylene gas at 50° C. for 18 hours using the given amounts of catalyst X008. After Zemplen's transesterification (NaOMe/MeOH; rt, 3 h) GCMS analysis was performed. The tests are outlined in Table 24, shown below.

TABLE 24

| Ex. | Reaction | Lot | Catalyst | ppmwt | Scale |
|---|---|---|---|---|---|
| 12(a) | E01JVA161H to FAME mix ethenolysis | E01JVA343 E01JVA344 E01JVA345 | X008 | 1000 750 500 | 0.9 ml (1 mmol) |

Example 12(b)

In a nitrogen gas filled glove box, SBO-1 (500 ml) was mixed with activated gamma-aluminum oxide (Brockman I., 5 g/100 ml) and the mixture was stirred at room temperature for 21 hours. Filtration gave E01JVA161A. (The initial PV=0.73 went down to PV=0.09.) E01JVA161A was mixed with Selcat-Q-6 10% Pd/C (0.25 g/100 ml) and charcoal (1 g/100 ml) and was stirred at 110° C. (internal temperature) while the glove-box's nitrogen atmosphere was bubbled through it. After 2 h the PV was under the detection limit. After 13 h, filtration on Whatman AutoCup (0.45 μm PTFE) by suction gave E01JVA161C. E01JVA161C was mixed with $Ac_2O$ (30 mol %) under nitrogen atmosphere at room temperature. The mixture was stirred at 110° C. (internal) for 18 hours, then the excess of the reagent and byproducts were distilled off under reduced pressure (17 mbar) while a constant nitrogen stream was bubbled through the oil slowly to help remove the volatile compounds. After 5 hours of distillation E01JVA161H was isolated by sucking out the distillation residue via a stainless steel needle taking care to avoid the mixing of the oil with the small drops on the internal wall of the distilling flask. Samples from E01JVA161H were placed in glass vials and stirred with the given amount of $Oc_3Al$ (25 wt % in hexane) at room temperature for 4 hours. The vials were then placed into a 850 ml stainless steel autoclave and the reaction mixtures were subjected to ethenolysis under 10 atm of ethylene gas at 50° C. for 18 hours using 250 ppmwt of catalyst X022. After Zemplen's transesterification (NaOMe/MeOH; rt, 3 h) GCMS analysis was performed. The tests are outlined in Table 25, shown below.

TABLE 25

| Ex. | Reaction | Lot | $Oc_3Al$ mol % | Catalyst | Scale |
|---|---|---|---|---|---|
| 12(b) | E01JVA161H to FAME mix $Oc_3Al$ treatment & ethenolysis | E01JVA800 E01JVA801 E01JVA802 E01JVA803 | 0.5 1 2 3 | 250 ppmwt X022 | 0.8 ml (0.83 mmol) |

Example 13

Canola oil (CO-1, 500 ml) was subjected to short way distillation 250° C., 0.25 mbar for 1 hour. The residue (E01JVA327heated) was chambered into a nitrogen gas filled glove box (PV: under the detection limit) and was stirred at room temperature with $Ac_2O$ (15 ml, 10 mol %) for 67 hours then at 105° C. for two hours. The excess of the reagent and the byproducts were distilled off under reduced pressure (pressure was decreased gradually from 650 mbar to 4 mbar during 30 min then the distillation was continued at 4 mbar) at 110° C. internal temperature while a constant slow nitrogen flow was bubbled through the oil via a stainless steel needle for 5 hours. After cooling down to room temperature E01JVA327$Ac_2O$ was isolated by sucking the oil from the flask via a stainless steel needle taking care to avoid the mixing of the oil with the small drops on the internal wall of the distilling flask. E01JVA327$Ac_2O$ was stirred at r.t. with activated γ-aluminum oxide (Brockman I., 5 g/100 ml) for 18 hours. Filtration on a pad of activated celite (d=5 cm, l=3 mm) and activated γ-aluminum oxide (Brockman I., 1.5 cm) gave E01JVA327A. A sample from E01JVA327A was placed into a 250 ml stainless steel autoclave and was subjected to ethenolysis under 10 atm of ethylene gas at 50° C. for 18 hours using the given amounts of catalyst X008. After Zemplen's transesterification (NaOMe/MeOH; rt, 3 h) GCMS analysis was performed. The test is outlined in Table 26, shown below.

TABLE 26

| Ex. | Reaction | Lot | Catalyst | ppmwt | Scale |
|---|---|---|---|---|---|
| 13 | E01JVA327A to FAME mix ethenolysis | E01JVA329 | X008 | 500 | 40 ml (43 mmol) |

Examples 14(a) and 14(b)

Example 14(a)

Canola oil (CO-1, 500 ml) was subjected to short way distillation first at r.t. until the vacuum decreased to 0.044 mbar than the temperature was increased to 250° C. and the distillation was continued until the initially increasing pressure fell back to 0.044 mbar (about 60-70 min). The residue (E01JVA335res) was chambered into a nitrogen as filled glove box and $Ac_2O$ was added (3 ml, 30 mol % to 100 ml of oil) and the mixture was stirred at 105° C. internal temperature for 24 hours. The volatiles were distilled off at reduced pressure (pressure was gradually decreased from 700 mbar to 7 mbar) increasing the internal temperature to 110° C. and a slow nitrogen stream was bubbled through the oil via a stainless steel needle for 4 hours then the oil was allowed to cool to room temperature, transferred into an Erlenmeyer flask by a hypodermic syringe taking care to avoid the mixing of the oil with the small drops on the internal wall of the distilling flask (giving E01JVA335A). E01JVA335A was stirred with activated molecular sieves (3 Å, beads, 25 g) at room temperature for 96 hours. Then the substrate was filtered on a pad of activated molecular sieves (3 Å, dust) to give E01JVA335B. E01JVA335B was stirred with activated alumina (Brockman I., 5 g/100 ml) at room temperature for 24 hours then the oil was filtered on an activated celite pad giving E01JVA335C. Samples from E01JVA335C were placed in glass vials into a 850 ml stainless steel autoclave and were subjected to ethenolysis under 10 atm of ethylene gas at 50° C. for 18 hours using the given amounts of catalyst X008. After Zemplen's transesterification (NaOMe/MeOH; rt, 3 h) GCMS analysis was performed. The tests are outlined in Table 27, shown below.

TABLE 27

| Ex. | Reaction | Lot | Catalyst | ppmwt | Scale |
|---|---|---|---|---|---|
| 14(a) | E01JVA335C to FAME mix ethenolysis | E01JVA340 E01JVA341 E01JVA342 | X008 | 1000 750 500 | 0.9 ml (1 mmol) |

Example 14(b)

Canola oil (CO-1, 500 ml) was subjected to short way distillation first at r.t. until the vacuum decreased to 0.044 mbar than the temperature was increased to 250° C. and the distillation was continued until the initially increasing pressure fell back to 0.044 mbar (about 60-70 min). The residue (E01JVA335res) was chambered into a nitrogen as filled glove box and $Ac_2O$ was added (3 ml, 30 mol % to 100 ml of oil) and the mixture was stirred at 105° C. internal temperature for 24 hours. The volatiles were distilled off at reduced pressure (pressure was gradually decreased from 700 mbar to 7 mbar) increasing the internal temperature to 110° C. and a slow nitrogen stream was bubbled through the oil via a stainless steel needle for 4 hours then the oil was allowed to cool to room temperature, transferred into an Erlenmeyer flask by a hypodermic syringe taking care to avoid the mixing of the oil with the small drops on the internal wall of the distilling flask (giving E01JVA335A). E01JVA335A was stirred with activated molecular sieves (3 Å, beads, 25 g) at room temperature for 96 hours. Then the substrate was filtered on a pad of activated molecular sieves (3 Å, dust) to give E01JVA335B. E01JVA335B was stirred with activated alumina (Brockman I., 5 g/100 ml) at room temperature for 24 hours then the oil was filtered on an activated celite pad giving E01JVA335C. Samples from E01JVA335C were placed in glass vials and were stirred with the given amounts of $Oc_3Al$ (25 wt % in hexane) at room temperature for 4 hours. The vials were then placed into a 850 ml stainless steel autoclave and the reaction mixtures were subjected to ethenolysis under 10 atm of ethylene gas at 50° C. for 18 hours using 250 ppmwt of catalyst X022. After Zemplen's transesterification (NaOMe/MeOH; rt, 3 h) GCMS analysis was performed. The tests are outlined in Table 28, shown below.

TABLE 28

| Ex. | Reaction | Lot | $Oc_3Al$ mol % | Catalyst | Scale |
|---|---|---|---|---|---|
| 14(b) | E01JVA335C to FAME mix $Oc_3Al$ treatment & ethenolysis | E01JVA804 E01JVA805 E01JVA806 E01JVA807 | 0.5 1 2 3 | 250 ppmwt X022 | 0.8 ml (0.83 mmol) |

Examples 15(a) and 15(b)

Example 15(a)

E01JVA327A (see Example 13; 400 ml) was percolated through a column (diameter=55 mm) packed with activated celite (height: 5 mm), activated molecular sieves (dust form, 0.3 nm, height: 22 mm) activated molecular sieves (beads, 3 Å, height: 70 mm) and activated alumina on the top of them (height: 20 mm) by suction (membrane pump) giving E01JVA327C (pAV was below the detection limit). Samples from E01JVA327C were placed in glass vials into a 850 ml stainless steel autoclave and were subjected to ethenolysis under 10 atm of ethylene gas at 50° C. for 18 hours using the given amounts of catalyst X008. After Zemplen's transesterification (NaOMe/MeOH; rt, 3 h) GCMS analysis was performed. The tests are outlined in Table 29, shown below.

TABLE 29

| Ex. | Reaction | Lot | Catalyst | ppmwt | Scale |
|---|---|---|---|---|---|
| 15(a) | E01JVA327C to FAME mix ethenolysis | E01JVA372 E01JVA373 E01JVA374 | X008 | 500 250 100 | 0.8 ml (0.9 mmol) |

Example 15(b)

E01JVA327A (see Example 13; 400 ml) was percolated through a column (diameter=55 mm) packed with activated celite (height: 5 mm), activated molecular sieves (dust form, 0.3 nm, height: 22 mm) activated molecular sieves (beads, 3 Å, height: 70 mm) and activated alumina on the top of them (height: 20 mm) by suction (membrane pump) giving E01JVA327C (pAV was below the detection limit). Samples from E01JVA327C were placed in glass vials and were stirred with the given amount of $Oc_3Al$ (25 wt % in hexane) at room temperature for 4 hours. The vials were then placed into a 850 ml stainless steel autoclave and the reaction mixtures were subjected to ethenolysis under 10 atm of ethylene gas at 50° C. for 18 hours using 250 ppmwt of catalyst X022. After Zemplen's transesterification (NaOMe/MeOH; rt, 3 h) GCMS analysis was performed. The tests are outlined in Table 30, shown below.

TABLE 30

| Ex. | Reaction | Lot | $Oc_3Al$ mol % | Catalyst | Scale |
|---|---|---|---|---|---|
| 15(b) | E01JVA327C to FAME mix $Oc_3Al$ treatment & ethenolysis | E01JVA788 E01JVA789 E01JVA790 E01JVA791 E01JVA792 E01JVA793 E01JVA794 E01JVA795 | 0 0.1 0.2 0.5 1 2 3 4 | 250 ppmwt X022 | 0.8 ml (0.83 mmol) |

Summary of Results from Examples 1-15

The sample analyses (calculated on pentadecane) for Examples 1-15 are provided in Table 31, shown below, wherein:

C[%] refers to conversion: Conversion=100−100×[(final moles of decenoate precursors)/(initial moles of decenoate precursors in the triglyceride)]; Decenoate precursors: oleate, linoleate, linolenate and palmitoleate chains.

S[%] refers to selectivity: Selectivity=100×(moles of M9D)/(total moles of all ester compounds in the product mixture except the decenoate precursor esters and the saturated esters); In the calculation α,ω-dicarboxylic acid dimethyl ester mols are multiplied by two as these compounds are made from two starting carboxylic acid chains by the catalyst.

M9D Y[%] refers to methyl 9-decenoate yield: Methyl 9-decenoate (M9D) Yield=(moles of M9D)×100/(initial moles of decenoate precursor chains);

TON refers to turnover number; TON=M9D Y[%]*substrate mols/catalyst mols

P[%] refers to ester purity: Ester purity=100×(moles of M9D)/(total moles of all ester compounds in the product mixture);

9-ODDAME Y[%] refers to dimethyl octadec-9-en-dicarboxylate yield: Dimethyl octadec-9-en-dicarboxylate (9-ODDAME)Yield=100×(moles of 9-ODDAME)/ [(initial moles of decenoate precursors in the triglyceride)/2].

TABLE 31

| # | Ex. | Lot (catalyst; cat amount in ppmwt; mol %; substrate/catalyst) | Sample analysis | | | | | |
|---|---|---|---|---|---|---|---|---|
| | | | C [%] | S [%] | M9DY [%] | TON | P [%] | 9-ODDAMEY [%] |
| 1 | 1(a) | E01JVA715 (X008; 109200 ppm; 10; 10) | 90.4 | 33.3 | 29.2 | 3 | 31.3 | 25.3 |
| 2 | | E01JVA716 (X008; 76440 ppm; 7; 14) | 90.4 | 38.6 | 34.1 | 5 | 36.2 | 23.7 |

TABLE 31-continued

| # | Ex. | Lot (catalyst; cat amount in ppmwt; mol %; substrate/catalyst) | Sample analysis |||||| 
|---|---|---|---|---|---|---|---|---|
| | | | C [%] | S [%] | M9DY [%] | TON | P [%] | 9-ODDAMEY [%] |
| 3 | | E01JVA717 (X008; 43680 ppm; 4; 25) | 49.1 | 15.4 | 7.3 | 2 | 7.0 | 4.5 |
| 4 | | E01JVA722 (X008; 10920 ppm; 1; 100) | 33.2 | 1.4 | 0.5 | 0 | 0.4 | 3.7 |
| 5 | | E01JVA723 (X008; 5460 ppm; 0.5; 200) | 31.9 | 0.4 | 0.1 | 0 | 0.1 | 3.6 |
| 6 | | E01JVA718 (X022; 121770 ppm; 10; 10) | 93.4 | 20.5 | 18.8 | 2 | 21.4 | 35.5 |
| 7 | | E01JVA719 (X022; 85240 ppm; 7; 14) | 94.7 | 12.6 | 11.8 | 2 | 13.9 | 40.5 |
| 8 | | E01JVA720 (X022; 48710 ppm; 4; 25) | 94.6 | 13.1 | 12.2 | 3 | 14.2 | 38.3 |
| 9 | | E01JVA724 (X022; 12180 ppm; 1; 100) | 33.5 | 0.6 | 0.2 | 0 | 0.2 | 3.8 |
| 10 | | E01JVA725 (X022; 6090 ppm; 0.5; 200) | 32.0 | −0.2 | −0.1 | 0 | −0.1 | 3.7 |
| 11 | 1(b) | E01JVA609 (X022; 250 ppm; 0.021; 4871) (0% Et$_3$Al) | 1.0 | 0.0 | 0.0 | 0 | 0.0 | 0.0 |
| 12 | | E01JVA610 (X022; 250 ppm; 0.021; 4871) (1% Et$_3$Al) | 1.1 | 0.0 | 0.0 | 0 | 0.0 | 0.0 |
| 13 | | E01JVA611 (X022; 250 ppm; 0.021; 4871) (2% Et$_3$Al) | 2.8 | 21.8 | 1.1 | 52 | 1.0 | 0.0 |
| 14 | | E01JVA612 (X022; 250 ppm; 0.021; 4871) (3% Et3Al) | 19.7 | 51.5 | 11.1 | 540 | 10.1 | 0.6 |
| 15 | | E01JVA613 (X022; 250 ppm; 0.021; 4871) (4% Et$_3$Al) | 83.2 | 80.9 | 68.6 | 3339 | 63.8 | 4.1 |
| 16 | | E01JVA614 (X022; 250 ppm; 0.021; 4871) (5% Et$_3$Al) | 93.4 | 83.0 | 79.2 | 3854 | 74.0 | 5.3 |
| 17 | | E01JVA615 (X022; 250 ppm; 0.021; 4871) (6% Et$_3$Al) | 87.8 | 83.1 | 74.5 | 3625 | 69.0 | 3.6 |
| 18 | | E01JVA616 (X022; 250 ppm; 0.021; 4871) (7% Et$_3$Al) | 90.9 | 83.3 | 77.2 | 3760 | 71.9 | 4.4 |
| 19 | | E01JVA617 (X022; 250 ppm; 0.021; 4871) (8% Et$_3$Al) | 86.5 | 82.6 | 73.0 | 3554 | 67.6 | 3.3 |
| 20 | | E01JVA618 (X022; 250 ppm; 0.021; 4871) (9% Et$_3$Al) | 90.0 | 83.3 | 76.4 | 3719 | 71.0 | 4.1 |
| 21 | | E01JVA683 (X022; 250 ppm; 0.021; 4871) (4% Oc$_3$Al) | 93.3 | 77.8 | 73.3 | 3566 | 70.4 | 10.1 |
| 22 | | E01JVA684a (X022; 250 ppm; 0.021; 4871) (5% Oc$_3$Al) | 93.2 | 79.2 | 74.4 | 3620 | 71.1 | 9.5 |
| 23 | | E01JVA685 (X022; 250 ppm; 0.021; 4871) (6% Oc$_3$Al) | 93.1 | 74.0 | 69.4 | 3380 | 67.5 | 12.3 |
| 24 | 2(a) | E01JVA740 (X008; 76440 ppm; 7; 14) | 96.0 | 35.7 | 33.7 | 5 | 35.3 | 20.8 |
| 25 | | E01JVA741 (X008; 43680 ppm; 4; 25) | 90.1 | 37.9 | 33.4 | 8 | 33.3 | 11.4 |
| 26 | | E01JVA742 (X008; 10920 ppm; 1; 100) | 37.3 | 2.3 | 0.8 | 1 | 0.8 | 4.0 |
| 27 | 2(b) | E01JVA641A (X022; 250 ppm; 0.021; 4871) (1% Et$_3$Al) | 4.1 | 0.5 | 0.0 | 1 | 0.0 | 0.2 |
| 28 | | E01JVA642A (X022; 250 ppm; 0.021; 4871) (2% Et$_3$Al) | 14.6 | 41.5 | 6.0 | 292 | 5.5 | 0.3 |
| 29 | | E01JVA643A (X022; 250 ppm; 0.021; 4871) (3% Et$_3$Al) | 58.0 | 71.8 | 40.7 | 1983 | 37.3 | 0.9 |
| 30 | | E01JVA644A (X022; 250 ppm; 0.021; 4871) (4% Et$_3$Al) | 88.9 | 79.4 | 70.8 | 3445 | 66.1 | 4.6 |
| 31 | | E01JVA645A (X022; 250 ppm; 0.021; 4871) (5% Et$_3$Al) | 89.5 | 82.1 | 71.6 | 3485 | 66.8 | 4.7 |
| 32 | | E01JVA646A (X022; 250 ppm; 0.021; 4871) (6% Et$_3$Al) | 87.8 | 79.5 | 69.1 | 3362 | 64.6 | 4.6 |
| 33 | 3(a) | E01JVA743 (X008; 76440 ppm; 7; 14) | 95.7 | 33.8 | 31.0 | 4 | 32.3 | 18.9 |
| 34 | | E01JVA744 (X008; 43680 ppm; 4; 25) | 76.7 | 36.6 | 27.1 | 7 | 26.4 | 6.3 |
| 35 | | E01JVA745 (X008; 10920 ppm; 1; 100) | 39.0 | 1.0 | 0.4 | 0 | 0.4 | 4.3 |
| 36 | 3(b) | E01JVA765 (X022; 250 ppm; 0.021; 4871) (2% Oc$_3$Al) | 5.0 | 0.7 | 0.0 | 2 | 0.0 | 0.5 |
| 37 | | E01JVA766 (X022; 250 ppm; 0.021; 4871) (3% Oc$_3$Al) | 9.8 | 25.3 | 2.8 | 134 | 2.5 | 0.5 |
| 38 | | E01JVA767 (X022; 250 ppm; 0.021; 4871) (4% Oc$_3$Al) | 32.7 | 53.7 | 17.9 | 871 | 16.5 | 0.7 |
| 39 | | E01JVA768 (X022; 250 ppm; 0.021; 4871) (5% Oc$_3$Al) | 59.1 | 67.5 | 39.9 | 1946 | 37.1 | 1.5 |
| 40 | 4(a) | E01JVA734 (X008; 76440 ppm; 7; 14) | 53.3 | 18.1 | 9.3 | 1 | 8.9 | 4.4 |
| 41 | | E01JVA735 (X008; 43680 ppm; 4; 25) | 42.9 | 3.0 | 1.2 | 0 | 1.2 | 4.4 |
| 42 | | E01JVA736 (X008; 10920 ppm; 1; 100) | 40.6 | −0.4 | −0.2 | 0 | −0.1 | 4.3 |
| 43 | 4(b) | E01JVA753 (X022; 250 ppm; 0.021; 4871) (2% Oc$_3$Al) | 5.8 | 0.0 | 0.0 | 0 | 0.0 | 0.1 |
| 44 | | E01JVA754 (X022; 250 ppm; 0.021; 4871) (3% Oc$_3$Al) | 6.3 | 0.1 | 0.0 | 0 | 0.0 | 0.1 |
| 45 | | E01JVA755 (X022; 250 ppm; 0.021; 4871) (4% Oc$_3$Al) | 6.0 | 0.2 | 0.0 | 1 | 0.0 | 0.1 |
| 46 | | E01JVA756 (X022; 250 ppm; 0.021; 4871) (5% Oc$_3$Al) | 5.9 | 0.3 | 0.0 | 1 | 0.0 | 0.1 |
| 47 | 5(a) | E01JVA737 (X008; 76440 ppm; 7; 14) | 96.1 | 33.8 | 31.9 | 5 | 33.8 | 22.5 |
| 48 | | E01JVA738 (X008; 43680 ppm; 4; 25) | 59.3 | 27.0 | 15.6 | 4 | 15.0 | 4.4 |
| 49 | | E01JVA739 (X008; 10920 ppm; 1; 100) | 33.5 | 1.7 | 0.6 | 1 | 0.5 | 3.7 |
| 50 | | E01JVA643 (X022; 2500 ppm; 0.21; 487) | 0 | 0 | 0 | 0 | 0 | 0 |

TABLE 31-continued

| # | Ex. | Lot (catalyst; cat amount in ppmwt; mol %; substrate/catalyst) | Sample analysis | | | | | |
|---|---|---|---|---|---|---|---|---|
| | | | C [%] | S [%] | M9DY [%] | TON | P [%] | 9-ODDAMEY [%] |
| 51 | | E01JVA644 (X022; 1000 ppm; 0.084; 1218) | 0 | 0 | 0 | 0 | 0 | 0 |
| 52 | | E01JVA645 (X022; 250 ppm; 0.021; 4871) | 0 | 0 | 0 | 0 | 0 | 0 |
| 53 | 5(b) | E01JVA757 (X022; 250 ppm; 0.021; 4871) (2% Oc₃Al) | 1.1 | 0.2 | 0.0 | 0 | 0.0 | 0.1 |
| 54 | | E01JVA758 (X022; 250 ppm; 0.021; 4871) (3% Oc₃Al) | 2.7 | 19.3 | 0.8 | 39 | 0.7 | 0.1 |
| 55 | | E01JVA759 (X022; 250 ppm; 0.021; 4871) (4% Oc₃A;) | 16.6 | 41.4 | 9.4 | 460 | 8.7 | 0.1 |
| 56 | | E01JVA760 (X022; 250 ppm; 0.021; 4871) (5% Oc₃Al) | 57.2 | 67.4 | 38.7 | 1887 | 35.9 | 1.3 |
| 57 | 6(a) | E01JVA726 (X008; 76440 ppm; 7; 14) | 95.6 | 36.5 | 34.0 | 5 | 34.9 | 17.0 |
| 58 | | E01JVA727 (X008; 43680 ppm; 4; 25) | 76.2 | 44.0 | 32.8 | 8 | 31.4 | 4.3 |
| 59 | | E01JVA728 (X008; 10920 ppm; 1; 100) | 33.3 | 0.9 | 0.3 | 0 | 0.3 | 3.7 |
| 60 | | E01JVA732 (X008; 5460 ppm; 0.5; 200) | 34.2 | −0.1 | 0.0 | 0 | 0.0 | 3.9 |
| 61 | | E01JVA729 (X022; 85240 ppm; 7; 14) | 94.6 | 13.7 | 12.6 | 2 | 14.6 | 37.7 |
| 62 | | E01JVA730 (X022; 48710 ppm; 4; 25) | 93.3 | 20.3 | 18.7 | 5 | 21.3 | 34.9 |
| 63 | | E01JVA731 (X022; 12180 ppm; 1; 100) | 34.4 | 1.6 | 0.5 | 1 | 0.5 | 3.8 |
| 64 | | E01JVA731 (X022; 6090 ppm; 0.5; 200) | 33.2 | −0.3 | −0.1 | 0 | −0.1 | 3.8 |
| 65 | | E01JVA703 (X022; 2500 ppm; 0.21; 487) | 0 | 0 | 0 | 0 | 0 | 0 |
| 66 | | E01JVA704 (X022; 1000 ppm; 0.084; 1218) | 0 | 0 | 0 | 0 | 0 | 0 |
| 67 | | E01JVA705 (X022; 250 ppm; 0.021; 4871) | 0 | 0 | 0 | 0 | 0 | 0 |
| 68 | 6(b) | E01JVA761 (X022; 250 ppm; 0.021; 4871) (2% Oc₃Al) | 5.4 | 2.7 | 0.2 | 9 | 0.2 | 0.6 |
| 69 | | E01JVA762 (X022; 250 ppm; 0.021; 4871) (3% Oc₃Al) | 13.6 | 23.0 | 3.4 | 166 | 3.1 | 0.7 |
| 70 | | E01JVA763 (X022; 250 ppm; 0.021; 4871) (4% Oc₃Al) | 68.5 | 70.4 | 48.2 | 2345 | 45.0 | 2.5 |
| 71 | | E01JVA764 (X022; 250 ppm; 0.021; 4871) (5% Oc₃Al) | 94.7 | 73.7 | 69.2 | 3372 | 67.2 | 10.3 |
| 72 | 7(a) | E01JVA746 (X008; 76440 ppm; 7; 14) | 95.7 | 32.9 | 30.8 | 4 | 32.3 | 20.6 |
| 73 | | E01JVA747 (X008; 43680 ppm; 4; 25) | 95.3 | 36.4 | 33.8 | 8 | 34.7 | 16.4 |
| 74 | | E01JVA748 (X008; 10920 ppm; 1; 100) | 36.1 | 2.0 | 0.7 | 1 | 0.7 | 3.9 |
| 75 | 7(b) | E01JVA769 (X022; 250 ppm; 0.021; 4871) (2% Oc₃Al) | 24.7 | 1.0 | 0.3 | 12 | 0.2 | 2.7 |
| 76 | | E01JVA770 (X022; 250 ppm; 0.021; 4871) (3% Oc₃Al) | 50.0 | 47.1 | 23.5 | 1144 | 22.0 | 2.4 |
| 77 | | E01JVA771 (X022; 250 ppm; 0.021; 4871) (4% Oc₃Al) | 90.4 | 60.6 | 54.2 | 2640 | 52.2 | 6.0 |
| 78 | | E01JVA772 (X022; 250 ppm; 0.021; 4871) (5% Oc₃Al) | 88.7 | 81.1 | 72.0 | 3508 | 67.6 | 3.8 |
| 79 | 8(a) | E01JVA749 (X008; 76440 ppm; 7; 14) | 95.7 | 33.4 | 31.2 | 4 | 32.7 | 20.8 |
| 80 | | E01JVA750 (X008; 43680 ppm; 4; 25) | 84.7 | 46.0 | 37.7 | 9 | 36.6 | 6.4 |
| 81 | | E01JVA751 (X008; 10920 ppm; 1; 100) | 34.9 | 1.6 | 0.6 | 1 | 0.5 | 3.8 |
| 82 | | E01JVA671 (X022; 2500 ppm; 0.21; 487) | 0 | 0 | 0 | 0 | 0 | 0 |
| 83 | | E01JVA672 (X022; 1000 ppm; 0.084; 1218) | 0 | 0 | 0 | 0 | 0 | 0 |
| 84 | | E01JVA673 (X022; 250 ppm; 0.021; 4871) | 0 | 0 | 0 | 0 | 0 | 0 |
| 85 | 8(b) | E01JVA773 (X022; 250 ppm; 0.021; 4871) (2% Oc₃Al) | 25.7 | 0.1 | 0.0 | 1 | 0.0 | 2.9 |
| 86 | | E01JVA774 (X022; 250 ppm; 0.021; 4871) (3% Oc₃Al) | 39.3 | 22.5 | 8.8 | 428 | 8.3 | 2.9 |
| 87 | | E01JVA775 (X022; 250 ppm; 0.021; 4871) (4% Oc₃Al) | 88.3 | 59.5 | 51.9 | 2528 | 49.8 | 5.4 |
| 88 | | E01JVA776 (X022; 250 ppm; 0.021; 4871) (5% Oc₃Al) | 90.8 | 62.0 | 56.4 | 2747 | 55.4 | 11.2 |
| 89 | 9(a) | E01JVA781 (X008; 76440 ppm; 7; 14) | 96.3 | 31.9 | 26.0 | 4 | 26.1 | 10.5 |
| 90 | | E01JVA782 (X008; 43680 ppm; 4; 25) | 78.2 | 24.9 | 17.6 | 4 | 17.4 | 7.6 |
| 91 | | E01JVA783 (X008; 10920 ppm; 1; 100) | 36.5 | 0.8 | 0.3 | 0 | 0.3 | 4.0 |
| 92 | 9(b) | E01JVA784 (X022; 250 ppm; 0.021; 4871) (2% Oc₃Al) | 6.0 | 4.3 | 0.3 | 13 | 0.2 | 0.5 |
| 93 | | E01JVA785 (X022; 250 ppm; 0.021; 4871) (3% Oc₃Al) | 13.2 | 27.3 | 3.7 | 182 | 3.4 | 0.6 |
| 94 | | E01JVA786 (X022; 250 ppm; 0.021; 4871) (4% Oc₃Al) | 54.5 | 67.0 | 36.5 | 1775 | 33.9 | 1.6 |
| 95 | | E01JVA787 (X022; 250 ppm; 0.021; 4871) (5% Oc₃Al) | 84.6 | 75.9 | 63.7 | 3103 | 60.9 | 6.6 |
| 96 | 10(a) | E01JVA809 (X008; 2000 ppm; 0.183; 546) | 58.4 | 70.9 | 42.0 | 229 | 39.0 | 1.2 |
| 97 | | E01JVA810 (X008; 1500 ppm; 0.137; 728) | 30.6 | 58.7 | 18.7 | 136 | 17.2 | 0.6 |
| 98 | | E01JVA811 (X008; 1000 ppm; 0.092; 1092) | 12.2 | 36.6 | 4.9 | 53 | 4.5 | 0.6 |
| 99 | | E01JVA812 (X008; 500 ppm; 0.046; 2184) | 5.1 | 3.6 | 0.2 | 5 | 0.2 | 0.6 |
| 100 | 10(b) | E01JVA815 (X022; 250 ppm; 0.021; 4871) 0.2 mol % Oc3Al | 6.3 | 14.6 | 1.1 | 55 | 1.0 | 0.5 |
| 101 | | E01JVA816 (X022; 250 ppm; 0.021; 4871) 0.5 mol % Oc3Al | 52.8 | 67.9 | 36.6 | 1783 | 33.9 | 1.2 |

TABLE 31-continued

| # | Ex. | Lot (catalyst; cat amount in ppmwt; mol %; substrate/catalyst) | Sample analysis | | | | | |
|---|---|---|---|---|---|---|---|---|
| | | | C [%] | S [%] | M9DY [%] | TON | P [%] | 9-ODDAMEY [%] |
| 102 | | E01JVA817 (X022; 250 ppm; 0.021; 4871) 1 mol % Oc3Al | 92.5 | 81.8 | 76.8 | 3739 | 72.8 | 6.0 |
| 103 | | E01JVA818 (X022; 250 ppm; 0.021; 4871) 2 mol % Oc3Al | 96.0 | 81.6 | 79.1 | 3852 | 75.5 | 7.8 |
| 104 | | E01JVA819 (X022; 250 ppm; 0.021; 4871) 3 mol % Oc3Al | 95.1 | 81.9 | 78.7 | 3835 | 75.0 | 7.2 |
| 105 | | E01JVA820 (X022; 250 ppm; 0.021; 4871) 4 mol % Oc3Al | 71.6 | 70.5 | 51.1 | 2490 | 48.0 | 3.8 |
| 106 | 11(a) | E01JVA778 (X008; 1000 ppm; 0.091; 1100) | 48.5 | 45.9 | 20.7 | 227 | 17.8 | 1.4 |
| 107 | | E01JVA779 (X008; 750 ppm; 0.068; 1467) | 23.5 | 26.9 | 5.8 | 86 | 5.0 | 1.7 |
| 108 | | E01JVA780 (X008; 500 ppm; 0.045; 2200) | 7.0 | 11.7 | 0.8 | 18 | 0.7 | 0.5 |
| 109 | | E01JVA181 (X007; 2410 ppm; 0.2, 500) | 99.1 | 91.3 | 83.9 | 420 | 74.7 | 0 |
| 110 | | E01JVA182 (X007; 1205 ppm; 0.1, 1000) | 90.2 | 0 | 58.5 | 585 | 52.0 | 0 |
| 111 | | E01JVA183 (X007; 720 ppm; 0.06, 1667) | 33.1 | 53.9 | 19.3 | 321 | 16.1 | 0 |
| 112 | 11(b) | E01JVA796 (X022; 250 ppm; 0.02; 4907) (0.5% Oc$_3$Al) | 9.8 | 4.9 | 0.4 | 19 | 0.3 | 0.6 |
| 113 | | E01JVA797 (X022; 250 ppm; 0.02; 4907) (1% Oc$_3$Al) | 21.4 | 42.6 | 10.4 | 510 | 8.9 | 0.6 |
| 114 | | E01JVA798 (X022; 250 ppm; 0.02; 4907) (2% Oc$_3$Al) | 98.2 | 83.1 | 85.1 | 4178 | 74.5 | 5.9 |
| 115 | | E01JVA799 (X022; 250 ppm; 0.02; 4907) (3% Oc$_3$Al) | 98.4 | 83.8 | 86.0 | 4221 | 75.3 | 6.1 |
| 116 | 12(a) | E01JVA343 (X008; 1000 ppm; 0.091, 1102) | 92.1 | 71.8 | 68.9 | 759 | 57.3 | 0.0 |
| 117 | | E01JVA344 (X008; 750 ppm; 0.066, 1515) | 86.4 | 62.9 | 61.6 | 905 | 51.3 | 0.0 |
| 118 | | E01JVA345 (X008; 500 ppm; 0.045, 2204) | 66.6 | 41.1 | 41.2 | 907 | 34.3 | 0.0 |
| 119 | 12(b) | E01JVA800 (X022; 250 ppm; 0.02; 4907) (0.5% Oc$_3$Al) | 11.3 | 11.0 | 1.0 | 48 | 0.8 | 0.6 |
| 120 | | E01JVA801 (X022; 250 ppm; 0.02; 4907) (1% Oc$_3$Al) | 98.4 | 83.2 | 85.4 | 4189 | 74.7 | 6.0 |
| 121 | | E01JVA802 (X022; 250 ppm; 0.02; 4907) (2% Oc$_3$Al) | 98.2 | 84.8 | 86.8 | 4262 | 75.8 | 5.4 |
| 122 | | E01JVA803 (X022; 250 ppm; 0.02; 4907) (3% Oc$_3$Al) | 97.9 | 82.9 | 83.3 | 4088 | 72.9 | 6.1 |
| 123 | 13(a) | E01JVA329 (X008; 500 ppm; 0.046, 2216) | 58.4 | 44.8 | 45.3 | 1006 | 41.5 | 0.3 |
| 124 | 14(a) | E01JVA340 (X008; 1000 ppm; 0.092, 1092) | 83.9 | 71.4 | 71.6 | 782 | 65.7 | 0 |
| 125 | | E01JVA341 (X008; 750 ppm; 0.069, 1456) | 70.4 | 57.4 | 57.5 | 837 | 52.7 | 0 |
| 126 | | E01JVA342 (X008; 500 ppm; 0.046, 2148) | 31.8 | 22.2 | 22.5 | 492 | 20.6 | 0 |
| 127 | 14(b) | E01JVA804 (X022; 250 ppm; 0.021; 4871) (0.5% Oc$_3$Al) | 9.2 | 18.7 | 1.6 | 78 | 1.5 | 0.6 |
| 128 | | E01JVA805 (X022; 250 ppm; 0.021; 4871) (1% Oc$_3$Al) | 56.4 | 70.3 | 41.5 | 2023 | 38.4 | 0.6 |
| 129 | | E01JVA806 (X022; 250 ppm; 0.021; 4871) (2% Oc$_3$Al) | 98.1 | 82.6 | 83.6 | 4071 | 79.3 | 5.9 |
| 130 | | E01JVA807 (X022; 250 ppm; 0.021; 4871) (3% Oc$_3$Al) | 97.9 | 83.1 | 84.1 | 4095 | 79.5 | 5.2 |
| 131 | 15(a) | E01JVA372 (X008; 500 ppm; 0.046, 2184) | 38.9 | 27.8 | 28.1 | 615 | 25.8 | 0.1 |
| 132 | | E01JVA373 (X008; 250 ppm; 0.023, 4368) | 1.1 | 0.5 | 0.5 | 20 | 0.4 | 0 |
| 133 | | E01JVA374 (X008; 100 ppm; 0.009, 10920) | 0.6 | 0.0 | 0.0 | 0 | 0.0 | 0 |
| 134 | 15(b) | E01JVA788 (X022; 250 ppm; 0.021; 4871) (0% Oc$_3$Al) | 12.2 | 25.2 | 3.4 | 165 | 3.1 | 0.6 |
| 135 | | E01JVA789 (X022; 250 ppm; 0.021; 4871) (0.1% Oc$_3$Al) | 16.5 | 28.5 | 5.0 | 241 | 4.6 | 0.8 |
| 136 | | E01JVA790 (X022; 250 ppm; 0.021; 4871) (0.2% Oc$_3$Al) | 24.3 | 50.7 | 12.4 | 603 | 11.4 | 0.5 |
| 137 | | E01JVA791 (X022; 250 ppm; 0.021; 4871) (0.5% Oc$_3$Al) | 94.7 | 64.9 | 60.5 | 2946 | 61.9 | 18.5 |
| 138 | | E01JVA792 (X022; 250 ppm; 0.021; 4871) (1% Oc$_3$Al) | 78.1 | 74.6 | 57.8 | 2816 | 54.9 | 5.0 |
| 139 | | E01JVA793 (X022; 250 ppm; 0.021; 4871) (2% Oc$_3$Al) | 94.9 | 68.2 | 63.3 | 3085 | 63.4 | 16.9 |
| 140 | | E01JVA794 (X022; 250 ppm; 0.021; 4871) (3% Oc$_3$Al) | 94.5 | 74.5 | 69.8 | 3398 | 68.5 | 11.7 |
| 142 | | E01JVA795 (X022; 250 ppm; 0.021; 4871) (4% Oc$_3$Al) | 94.7 | 74.7 | 70.0 | 3407 | 68.4 | 12.4 |

Comparison of Treatments in Examples 1-15:

Table 32, shown below, provides an overview of the various treatments conducted in Examples 1-15, as well as their MD9 yield % and selectivity %.

decreased considerably by increasing the applied $Alk_3Al$ amount above the optimal value. In general, the maximum M9D yield and selectivity values were usually not reached (C12:1, C13:2 & C16:3 Me esters in the product mixture).

TABLE 32

| Ex. | Treatment | A. Ethenolysis by X008 (X022, X007) Conversion % (M9D yield %, Selectivity %) | B. Trialkylaluminum demand Conversion % (M9D yield %, Selectivity %) |
|---|---|---|---|
| 1 | None | 4 mol % X008 (43680 ppm): 49.1 (7.3; 15.4) | 5 mol % $Et_3Al$: 93.4 (79.2; 83.0)<br>5 mol % $Oc_3Al$: 93.2 (74.4; 79.2) |
| 2 | Drying by mol. Sieves | 4 mol % X008 (43680 ppm): 90.1 (33.4; 37.9)<br>1 mol % X008 (10920 ppm): 37.3 (0.8; 2.3) | 4 mol % $Et_3Al$: 88.9 (70.8; 79.4) |
| 3 | Heating at 200° C. under $N_2$ for 2 h. | 4 mol % X008 (43680 ppm): 76.7 (27.1; 36.6)<br>1 mol % X008 (10920 ppm): 39.0 (0.4; 1.0) | 5 mol % $Oc_3Al$: 59.1 (39.9; 67.5) |
| 4 | Distillation treatment | 4 mol % X008 (43680 ppm): 42.9 (1.2; 3.0) | 5 mol % $Oc_3Al$: 5.9 (0.0; 0.3) |
| 5 | Cu/r.t. | 4 mol % X008 (43680 ppm): 59.3 (15.6; 27.0) | 5 mol % $Oc_3Al$: 57.2 (38.7; 67.4) |
| 6 | Cu/200° C. | 4 mol % X008 (43680 ppm): 76.2 (32.8; 44.0)<br>4 mol % X022 (48710 ppm): 93.3 (18.7; 20.3) | 5 mol % $Oc_3Al$: 94.7 (69.2; 73.7)<br>4 mol % $Oc_3Al$: 68.5 (48.2; 70.4) |
| 7 | Cu/200° C. + mol. sieves | 4 mol % X008 (43680 ppm): 95.3 (33.8; 36.4)<br>1 mol % X008 (10920 ppm): 36.1 (0.7; 2.0) | 4 mol % $Oc_3Al$: 90.4 (54.2; 60.6)<br>3 mol % $Oc_3Al$: 50.0 (23.5; 47.1) |
| 8 | Mg/r.t. | 4 mol % X008 (43680 ppm): 84.7 (37.7; 46.0) | 5 mol % $Oc_3Al$: 90.8 (56.4; 62.0)<br>4 mol % $Oc_3Al$: 88.3 (51.9; 59.5) |
| 9 | Mg/200° C. | 4 mol % X008 (43680 ppm): 78.2 (17.6; 24.9) | 5 mol % $Oc_3Al$: 84.6 (63.7; 75.9)<br>4 mol % $Oc_3Al$: 54.5 (36.5; 67.0) |
| 10 | $Ac_2O$ | 0.183 mol % X008 (2000 ppm): 58.4 (42.9; 70.9) | 1 mol % $Oc_3Al$: 92.5 (76.8; 81.8) |
| 11 | $Ac_2O + Al_2O_3$ * | 0.091 mol % X008 (1000 ppm): 48.5 (20.7; 45.9)<br>0.1 mol % X007 (1275 ppm): 90.2 (58.5; 68.8) | 2 mol % $Oc_3Al$: 98.2 (85.1; 83.1) |
| 12 | $Al_2O_3$, Pd/C – 100° C., $Ac_2O$ * | 0.091 mol % X008 (1000 ppm): 92.1 (68.9; 71.8)<br>0.045 mol % X008 (500 ppm): 66.6 (41.2; 41.1) | 1 mol % $Oc_3Al$: 98.4 (85.4; 83.2) |
| 13 | Distillation, $Ac_2O$, $Al_2O_3$ | 0.046 mol % X008 (500 ppm): 58.4 (45.3; 44.8) (large scale ethenolysis) | —** |
| 14 | Distillation, $Ac_2O$, mol. Sieves, $Al_2O_3$ | 0.092 mol % X008 (1000 ppm): 83.9 (71.6; 71.4)<br>0.046 mol % X008 (500 ppm): 31.8 (22.5; 22.2) | 2 mol % $Oc_3Al$: 98.1 (83.6; 82.6) |
| 15 | Distillation, $Ac_2O$, $Al_2O_3$, percolation (mol. sieves + $Al_2O_3$) | 0.046 mol % X008 (500 ppm): 38.9 (28.1; 27.8) | 0.5 mol % $Oc_3Al$: 94.7 (60.5; 64.9)<br>2 mol % $Oc_3Al$: 94.9 (63.3; 68.2) |

* Soybean oil used as the substrate
** not performed due to lack of substrate

Based on the results from Examples 1-15, it was observed that nearly complete conversion could be achieved in ethenolysis of commercial grade edible rapeseed oil (Canola oil) without any pretreatment by 7 mol % X008. However, the M9D yield and the selectivity were low. Slightly worse results were seen by catalyst X022, however after the application of $Alk_3Al$, the use of X022 was improved.

Among the pretreatment methods, it was observed that the catalyst loading could be decreased the most effectively by drying.

Worse results were seen with Mg treatment at high temperature than at room temperature, suggesting some kind of decomposition side reaction was taking place.

It was also observed that the most effective initial pretreatment method was the $Ac_2O$ treatment. $Alk_3Al$ demand could also be considerably decreased by $Ac_2O$ treatment. The success of $Ac_2O$ and vacuum distillation treatment highly depends on the quality of the separation of the volatile components. In case of most treatments and treatment combinations the conversion was not decreased considerably by the application of slight excess of $Al_3Al$ than the optimal amount. The only exception observed is when $Ac_2O$ treatment was applied alone. In this case the observed conversion is It was also observed that the best pretreatment combination method prior to ethenolysis of natural triglycerides was the $Ac_2O$ treatment followed by $Alk_3Al$ treatment. Percolation on activated alumina or molecular sieves can be applied before or instead of the $Alk_3Al$ treatment.

As for catalyst, X008 was observed to be the best choice if $Alk_3Al$ treatment was not used. X022 was observed to be the best catalyst choice when the $Alk_3Al$ treatment was applied.

Example 16

Study of Catalyst Addition in Ethenolysis of Pretreated Natural Triglycerides

In an experiment using $Et_3Al$ treated canola oil as substrate the catalyst was added in small portions to the reaction mixture during the course of the ethenolysis reaction. Samples were taken from the reaction mixture that were analyzed to follow the progress of the ethenolysis reaction.

In a nitrogen filled glove box Canola oil (CO-1, 1000 ml) was mixed with triethylaluminum (25 wt % in toluene, 35.5 ml; 6.5 mol %) and the mixture was stirred at room temperature for 5 days giving E01JVA399.

In a nitrogen filled glove box $Et_3Al$ treated Canola rapeseed oil (E01JVA399, 511.19 g; 579.45 mmol; average MW:

882.19) was placed into a stainless steel autoclave and stirred at 50° C. The gas space was filled with ethylene then the stock solution (0.01 M in benzene) of catalyst X022 (X01JVA036) was injected into the autoclave from time to time and the stirring under 10 bar of ethylene gas at 50° C. was continued. At times of the catalyst injections the ethylene overpressure in the autoclave was reduced by letting out the ethylene excess without opening the autoclave and samples were taken for GCMS analysis at the same time. The catalyst addition and sample taking were done by a hypodermic syringe via a stainless steel needle which was driven through a precision rubber septum put on the opening of a ball valve attached to the top of the autoclave. The valve was opened only during the injection—sample taking operations. The samples were analyzed by GCMS-FiD after Zemplen's transesterification.

Addition Sequence:
50×1 ppm of catalyst X022; ethenolysis under 10 bar of ethylene at 50° C. for different time periods.
1×50 ppm of catalyst X022; ethenolysis under 10 bar of ethylene at 50° C. for 22 hours.
Et$_3$Al (equal molar amount with 100 ppm of X022); 50° C. for 2 hours.
2×1 ppm of catalyst X022; ethenolysis under 10 bar of ethylene at 50° C. for 2×1 hours.
Finally 5 ppm of catalyst X022; ethenolysis under 10 bar of ethylene at 50° C. for 18 hours.

The sample analyses (calculated on pentadecane) for Example 16 are provided in Table 33, shown below, wherein:
C[%] refers to conversion: Conversion=100−100×[(final moles of decenoate precursors)/(initial moles of decenoate precursors in the triglyceride)]; Decenoate precursors: oleate, linoleate, linolenate and palmitoleate chains.
S[%] refers to selectivity: Selectivity=100×(moles of M9D)/(total moles of all ester compounds in the product mixture except the decenoate precursor esters and the saturated esters); In the calculation α,ω-dicarboxylic acid dimethyl ester mols are multiplied by two as these compounds are made from two starting carboxylic acid chains by the catalyst.
M9D Y[%] refers to methyl 9-decenoate yield: Methyl 9-decenoate (M9D) Yield=(moles of M9D)×100/(initial moles of decenoate precursor chains);
TON refers to turnover number; TON=M9D Y[%]*substrate mols/catalyst mols
P[%] refers to ester purity: Ester purity=100×(moles of M9D)/(total moles of all ester compounds in the product mixture);
9-ODDAME Y[%] refers to dimethyl octadec-9-en-dicarboxylate yield: Dimethyl octadec-9-en-dicarboxylate (9-ODDAME)Yield=100×(moles of 9-ODDAME)/ [(initial moles of decenoate precursors in the triglyceride)/2].

TABLE 33

| Entry | Reaction | Lot (cat amount; mol %, substrate/catalyst) | Reaction time [h] | C [%] | S [%] | M9DY [%] | TON | P [%] | M9ODDY [%] |
|---|---|---|---|---|---|---|---|---|---|
| 1 | E01JVA399 to FAME mix | E01JVA624RM1 (1 ppm; 0.00008; 1216909) | 2 | 9.7 | 27.4 | 3.2 | 38877 | 2.9 | 0.6 |
| 2 | | E01JVA624RM2 (2 ppm; 0.00016; 608455) | 2 | 21.1 | 34.8 | 7.8 | 47518 | 7.2 | 2.0 |
| 3 | | E01JVA624RM3 (3 ppm; 0.00025; 405636) | 2 | 16.5 | 43.0 | 7.8 | 31698 | 7.1 | 0.6 |
| 4 | | E01JVA624RM4 (4 ppm; 0.00033; 304227) | 2 | 20.6 | 48.4 | 10.8 | 32986 | 9.9 | 0.5 |
| 5 | | E01JVA624RM5 (5 ppm; 0.0004; 243382) | 15 | 27.9 | 52.9 | 15.6 | 38037 | 14.3 | 0.7 |
| 6 | | E01JVA624RM6 (6 ppm; 0.0005; 202818) | 2 | 29.4 | 56.3 | 17.5 | 35498 | 16.0 | 0.6 |
| 7 | | E01JVA624RM7 (7 ppm; 0.0006; 173844) | 3 | 32.9 | 56.4 | 19.5 | 33867 | 17.8 | 0.7 |
| 8 | | E01JVA624RM8 (8 ppm; 0.0007; 152114) | 3 | 36.1 | 58.6 | 22.0 | 33514 | 20.2 | 0.8 |
| 9 | | E01JVA624RM9 (9 ppm; 0.0007; 135212) | 16 | 41.7 | 61.3 | 26.6 | 35928 | 24.4 | 0.9 |
| 10 | | E01JVA624RM10 (10 ppm; 0.0008; 121691) | 3 | 42.8 | 62.0 | 27.4 | 33320 | 25.1 | 0.9 |
| 11 | | E01JVA624RM11 (11 ppm; 0.0009; 110628) | 3 | 44.3 | 62.0 | 28.6 | 31620 | 26.2 | 0.9 |
| 12 | | E01JVA624RM12 (12 ppm; 0.0010; 101409) | 3 | 47.4 | 63.3 | 30.9 | 31334 | 28.4 | 1.1 |
| 13 | | E01JVA624RM13 (13 ppm; 0.0011; 93608) | 111 | 53.4 | 66.2 | 36.4 | 34117 | 33.4 | 1.0 |
| 14 | | E01JVA624RM14 (14 ppm; 0.0012; 86922) | 2 | 54.1 | 66.9 | 37.2 | 32340 | 34.1 | 1.1 |
| 15 | | E01JVA624RM15 (15 ppm; 0.0012; 81127) | 2 | 55.7 | 67.4 | 38.6 | 31283 | 35.4 | 1.1 |
| 16 | | E01JVA624RM16 (16 ppm; 0.0013; 76057) | 2 | 57.9 | 67.5 | 40.1 | 30510 | 36.9 | 1.3 |
| 17 | | E01JVA624RM17 (17 ppm; 0.0014; 71583) | 18 | 61.2 | 69.7 | 43.7 | 31271 | 40.2 | 1.5 |
| 18 | | E01JVA624RM18 (18 ppm; 0.0015; 67606) | 2 | 62.0 | 69.6 | 44.2 | 29849 | 40.6 | 1.8 |
| 19 | | E01JVA624RM19 (19 ppm; 0.0016; 64048) | 3 | 63.0 | 69.6 | 44.8 | 28718 | 41.3 | 2.0 |
| 20 | | E01JVA624RM20 (20 ppm; 0.0016; 60845) | 3 | 64.4 | 69.2 | 45.5 | 27670 | 42.0 | 2.2 |

TABLE 33-continued

| Entry | Reaction | Lot (cat amount; mol %, substrate/catalyst) | Reaction time [h] | C [%] | S [%] | M9DY [%] | TON | P [%] | M9ODDY [%] |
|---|---|---|---|---|---|---|---|---|---|
| 21 | | E01JVA624RM21 (21 ppm; 0.0017; 57948) | 2 | 65.4 | 69.2 | 46.1 | 26733 | 42.7 | 2.5 |
| 22 | | E01JVA624RM22 (22 ppm; 0.0018; 55314) | 18 | 67.7 | 70.9 | 48.9 | 27029 | 45.2 | 2.7 |
| 23 | | E01JVA624RM23 (23 ppm; 0.0019; 52909) | 3 | 67.8 | 71.2 | 49.2 | 26021 | 45.6 | 3.1 |
| 24 | | E01JVA624RM24 (24 ppm; 0.002; 50705) | 3 | 69.0 | 71.2 | 50.1 | 25378 | 46.4 | 3.2 |
| 25 | | E01JVA624RM25 (25 ppm; 0.002; 48676) | 403 | 71.1 | 70.4 | 50.9 | 24776 | 47.2 | 1.5 |
| 26 | | E01JVA624RM26 (26 ppm; 0.002; 46804) | 4 | 71.7 | 70.5 | 51.2 | 23981 | 47.5 | 1.5 |
| 27 | | E01JVA624RM27 (27 ppm; 0.002; 45071) | 2 | 72.0 | 69.1 | 50.4 | 22712 | 47.0 | 2 |
| 28 | | E01JVA624RM28 (28 ppm; 0.002; 43461) | 17 | 73.6 | 72.3 | 53.9 | 23445 | 50.1 | 1.6 |
| 29 | | E01JVA624RM29 (29 ppm; 0.002; 41962) | 2 | 74.0 | 72.8 | 54.7 | 22939 | 50.8 | 1.6 |
| 30 | | E01JVA624RM30 (30 ppm; 0.003; 40564) | 3 | 75.2 | 71.8 | 55.0 | 22310 | 51.1 | 1.6 |
| 31 | | E01JVA624RM31 (31 ppm; 0.003; 39255) | 2 | 75.1 | 72.8 | 55.5 | 21784 | 51.6 | 1.8 |
| 32 | | E01JVA624RM32 (32 ppm; 0.003; 38028) | 17 | 76.3 | 72.4 | 56.0 | 21298 | 52.3 | 2.1 |
| 33 | | E01JVA624RM33 (33 ppm; 0.003; 36876) | 3 | 75.8 | 70.6 | 54.0 | 19902 | 50.6 | 2.6 |
| 34 | | E01JVA624RM34 (34 ppm; 0.003; 35791) | 2 | 77.2 | 71.4 | 55.8 | 19966 | 52.2 | 2.3 |
| 35 | | E01JVA624RM35 (35 ppm; 0.003; 34769) | 2 | 77.3 | 71.1 | 55.5 | 19283 | 51.9 | 2.3 |
| 36 | | E01JVA624RM36 (36 ppm; 0.003; 33803) | 2 | 78.0 | 71.9 | 56.7 | 19155 | 53.1 | 2.4 |
| 37 | | E01JVA624RM37 (37 ppm; 0.003; 32889) | 15 | 79.1 | 72.0 | 57.5 | 18923 | 54.0 | 2.7 |
| 38 | | E01JVA624RM38 (38 ppm; 0.003; 32024) | 2 | 79.9 | 72.1 | 58.3 | 18678 | 54.7 | 2.4 |
| 39 | | E01JVA624RM39 (39 ppm; 0.003; 31203) | 5 | 80.4 | 73.3 | 59.5 | 18575 | 55.8 | 2.4 |
| 40 | | E01JVA624RM40 (40 ppm; 0.003; 30423) | 89 | 81.1 | 73.6 | 60.4 | 18367 | 56.7 | 2.8 |
| 41 | | E01JVA624RM41 (41 ppm; 0.003; 29681) | 1 | 81.2 | 74.2 | 60.9 | 18081 | 57.2 | 2.6 |
| 42 | | E01JVA624RM42 (42 ppm; 0.004; 28974) | 1 | 81.2 | 74.8 | 61.4 | 17792 | 57.6 | 2.6 |
| 43 | | E01JVA624RM43 (43 ppm; 0.004; 28300) | 1 | 80.9 | 72.3 | 59.1 | 16711 | 55.7 | 3.2 |
| 44 | | E01JVA624RM44 (44 ppm; 0.004; 27657) | 1 | 81.1 | 72.7 | 59.6 | 16475 | 56.2 | 3.1 |
| 45 | | E01JVA624RM45 (45 ppm; 0.004; 27042) | 1 | 81.2 | 71.5 | 58.5 | 15819 | 55.3 | 6.9 |
| 46 | | E01JVA624RM46 (46 ppm; 0.004; 26455) | 1 | 81.3 | 71.1 | 58.2 | 15383 | 55.1 | 7.4 |
| 47 | | E01JVA624RM47 (47 ppm; 0.004; 25892) | 1 | 82.2 | 73.2 | 60.9 | 15756 | 57.6 | 7.4 |
| 48 | | E01JVA624RM48 (48 ppm; 0.004; 25352) | 1 | 82.7 | 73.4 | 61.4 | 15571 | 58.0 | 7 |
| 49 | | E01JVA624RM49 (49 ppm; 0.004; 24835) | 16 | 84.8 | 75.1 | 64.5 | 16018 | 61.0 | 6.8 |
| 50 | | E01JVA624RM50 (50 ppm; 0.004; 24338) | 2 | 84.0 | 70.9 | 59.9 | 14587 | 56.9 | 7.8 |
| 51 | | E01JVA624RM51 (100 ppm; 0.008; 12169) | 22 | 93.1 | 78.5 | 73.7 | 8972 | 69.8 | 7.6 |
| 52 | | Et₃Al addition: E01JVA624RM52pre (100 ppm; 0.008; 12169) | 2 | 92.2 | 76.4 | 71.1 | 8649 | 67.6 | 7.9 |
| 52 pre | | E01JVA624RM52 (101 ppm; 0.008; 12049) | 14 | 92.2 | 76.9 | 71.4 | 8605 | 67.9 | 8.1 |
| 53 | | E01JVA624RM53 (102 ppm; 0.008; 11930) | 2 | 92.2 | 76.8 | 71.0 | 8474 | 67.5 | 8 |
| 54 | | E01JVA624RM54 (107 ppm; 0.009; 11373) | 5 | 92.7 | 77.7 | 72.3 | 8222 | 68.5 | 7.4 |
| 55 | | E01JVA624crude (157 ppm; 0.013; 7751) | 18 | 93.6 | 79.1 | 74.2 | 5754 | 70.5 | 8.5 |

Based on the results from Example 16, It was observed that the catalyst loading could be further decreased in case of Alk$_3$Al treated triglyceride ethenolysis by catalyst X022 by the slow addition of the catalyst to the reaction mixture during the course of the reaction.

Examples 17-34

Materials and Methods

Methyl 9,12-tridecadienoate and 1-decene (91.4%) were obtained from Materia. 9-DAME samples were derived from natural oil feedstocks under conditions similar to those described in U.S. Patent Application Publication No. 2011/0113679, herein incorporated by reference in its entirety, and, depending on the source and handling, contained different types and amounts of impurities. Unless otherwise noted, the 9-DAME used in the examples below was the material sourced from Materia, Inc. (Pasadena, Calif., USA).

1-octene was obtained from Alfa-Aesar. Molecular sieves (4 Å, bead, 8-12 mesh) and alumina (activated, neutral, Brockmann I, ~150 mesh, 58 Å pore size) were obtained from Sigma-Aldrich. Molecular sieves were activated by heating in one of two ways: (a) 250° C. at 0.05 torr or (b) 150° C. in air. Activated alumina was dried either at 250° C. in vacuo (<0.1 torr) or at 375° C. under a flow of nitrogen (0.5-2 L/min). Substrates (e.g., decenoate ester) can be stored over activated molecular sieves prior to use and monitored via Karl Fischer titration until the moisture value is <10 ppm. In some embodiments, agitation and moving to a fresh bed of sieves can be helpful in expediting the time required to reach the desired moisture value. Additionally, in some embodiments, flocculation of the sieve dust and/or filtration can affect the times. Columns were prepared and run using vacuum or pressure to percolate substrate through the adsorbent. Peroxide value [milliequivalents peroxide/kg of sample (meq/kg)] was determined by through titration utilizing an autotitrator (Metrohm 888 Titrando). Moisture content was determined by coulometric Karl Fischer titration using a Metrohm 756 KF Coulometer. Unless otherwise noted, all metathesis reactions were conducted on a 1-gram scale inside of a glove box at ambient temperature.

Example 17

Large-Scale Self-Metathesis of 9-DAME to 9-ODDAME

Purification of 9-DAME: 9-DAME was stored over 10% wt. of unactivated 4 Å molecular sieves for 24 hours. This procedure reduced the residual moisture content from 212 ppm to 31 ppm. The material was then transferred to a solvent bulb style flask and degassed by 3 pump-purge cycles and the brought into a glove box. The material was percolated three times through a column of activated alumina (20% wt.). This procedure reduced the moisture content to 5 ppm and the peroxide value was found to be at or below that of a blank sample. The material was left over 10% wt. of activated 4 Å molecular sieves inside the glove box. The molecular sieves were dried at 250° C. in vacuo (<0.1 torr). Activated alumina was dried at 250° C. in vacuo (<0.1 torr).

Synthesis of 9-ODDAME: In a N$_2$-filled glove box, a 1-L round-bottomed flask equipped with a magnetic stir bar was charged with 250 g 9-DAME that had been dried via passage through a column of activated alumina and then stored over activated 4 Å molecular sieves. A solution of X004 was prepared by combining 40.1 mg Mo(NAr)(CHCMe$_2$Ph) (Me$_2$pyr)$_2$ and 16.7 mg 2,6-diphenylphenol in 1 mL of toluene followed by stirring the solution at ambient temperature for 30 minutes. The catalyst solution was added to the ester and the mixture was stirred open to the glove box atmosphere for 6 hours, after which time the mixture was placed under dynamic vacuum for 2 hours during which time gas evolution was observed. After standing overnight, the flask was removed from the glove box after an inlet adapter with a needle valve was fitted. The mixture was melted in a 50° C. silicone oil bath and placed under dynamic vacuum for 1 hour during which time more gas evolution was observed. The observed GC conversion was 92% (18,400 TON). Neutral activated alumina (12.5 g) was added and the mixture stirred for 30 minutes and then the alumina was removed by filtration. The light components of the mixture were removed by vacuum distillation (120° C. at 0.3 mm Hg) and then the bottoms were again treated with 12.5 g of neutral activated alumina to remove a green colored impurity. The isolated yield was 186.91 g (80.9% yield).

Example 18

It had been found previously that 0.04 mol % of the molybdenum catalyst X027 [Mo(N-2,6-$^i$Pr$_2$-C$_6$H$_3$)(CHCMe$_2$Ph)(pyrrolide)(O-2,6-$^t$Bu$_2$C$_6$H$_3$)] would only convert 9-DAME, purified by a thermal method (thermally treated at 200° C., followed by stirring over alumina dried at 250° C. in vacuo; PV reduced from 0.56 to <0.06 (blank)), to 9-ODDAME 0.2% (5 TON). Additionally, it was found that 0.04 mol % of X007 [Mo(N-2,6-$^i$Pr$_2$-C$_6$H$_3$)(CHCMe$_2$Ph)(2,5-dimethylpyrrolide)[(R)-3,3'-dibromo-2'-(tert-butyldimethylsilyloxy)-5,5',6,6',7,7',8,8'-octahydro-1,1'-binaphth-2-oate)]] would similarly give low conversion (3.5%; 88 TON) with the same substrate. It was found that addition of 10 wt % 4 Å molecular sieve that had been activated in vacuo at 275° C. reduced that moisture content from 76 ppm to 12 ppm. After drying, 0.04 mol % X027 would give 91.9% conversion (2298 TON) and 0.04 mol % X007 would give 88.0% conversion (2200 TON).

Example 19

The elimination of the thermal pretreatment step in the purification of 9-DAME was investigated. Stirring of 9-DAME over 20 wt % dry alumina (250° C., vacuum) followed by the addition of 20 wt % activated 4 Å molecular sieves reduced the peroxide value from 0.64 to 0.16 milliequivalents peroxide/kg of sample (meq/kg) and the moisture content from 194 ppm to 3 ppm.

Example 20

Reaction of the 9-DAME prepared without thermal pretreatment with 0.02 mol % of X027 resulted in 87.4% conversion (4368 TON). With feed that was thermally pretreated (vide supra Example 18) 77.6% conversion was observed (3880 TON). At a catalyst loading of 0.01 mol %, 47.3% conversion (4726 TON) could be achieved with the feed not thermally pretreated, whereas only 22.8% conversion (2277 TON) with the feed that had been thermally pretreated.

Example 21

Methyl 9,12-tridecadienoate was purified by percolation through an alumina column and storage over molecular sieves. This procedure reduced the peroxide value from 12.75 to 0.06 and the moisture content from 166 ppm to 5 ppm.

Example 22

Repeated percolation of 9-DAME through a 20 wt % column of dry alumina was found to reduce the peroxide value from 0.56 to <0.06 (blank). Addition of 20 wt % 4 Å molecular sieves reduced the moisture content from 194 ppm to 7 ppm.

Example 23

0.004 mol % of X004 [Mo(N-2,6-$^i$Pr$_2$-C$_6$H$_3$)(CHCMe$_2$Ph)(2,5-dimethylpyrrolide)(O-2,6-Ph$_2$C$_6$H$_3$)] was found to give 25.4% conversion (6350 TON) of 9-DAME percolated through alumina and dried over molecular sieves.

Example 24

Decanting the 9-DAME purified from the molecular sieve bed and placing it over a fresh 10 wt % bed of molecular sieve allowed for 0.004 mol % X004 to achieve 46.8% conversion (11693 TON).

Example 25

1-decene (91.4%) which had a peroxide value of 35.89 meq/kg and a moisture content of 259 ppm was purified by passage through a column of dry alumina (150° C. in air) and storage over activated 4 Å molecular sieves in the glove box. This procedure reduced the peroxide value to 0.16 meq/kg and the moisture to 5 ppm.

Example 26

It was found that 0.001 mol % X004 would react with purified 1-decene (vide supra) converting 63.1% to 9-octadecene.

Example 27

Addition of 5 wt % 4 Å molecular sieves dried at 150° C. in air to 1-octene reduced the moisture content from 42 ppm to 3 ppm. It was found on a 10-kg scale that 0.00225 mol % of X004 (150 ppm by weight) would convert this dried 1-octene to 7-tetradecene in 86.9% conversion.

Example 28

9-DAME was dried with 2.5 wt % of 4 Å molecular sieves. This reduced the moisture content from 68 ppm to 15 ppm. Attempted self-metathesis of this material with 0.01 mol % X004 resulted in <0.1% conversion to 9-ODDAME.

Example 29

9-DAME pre-dried with molecular sieves was percolated through an alumina-packed stainless steel (activated at 375° C. with a nitrogen purge) column by nitrogen pressure. The material was then collected and stored over a bed of activated (275° C., vacuum) 4 Å molecular sieves. The moisture content was then found to be 5 ppm. Metathesis with 0.01 mol % X004 converted 20.1% of 9-DAME to 9-ODDAME, up from trace conversion before alumina treatment. This 9-DAME was later used for an 8-kg scale reaction where it was found 0.0149 mol % (600 ppm by weight) of X004 would give 91.2% conversion of 9-DAME to 9-ODDAME.

Example 30

A 8 kg Mo-catalyzed self-metathesis of Elevance-derived 9-DAME to 9-ODDAME was completed via the procedure described in Example 17. The reaction proceeded to 91.2% conversion with an initial catalyst charge of 600 ppmwt X004. An additional charge of 100 ppmwt X004 resulted in a final conversion of 95.4%. Previous work had indicated that a catalyst loading of 200 ppmwt was sufficient to achieve >90% conversion of a different sample of 9-DAME to 9-ODDAME with the same catalyst with an approximate moisture content of the feed was <5 ppm. It was determined that there were no protic or phosphorus containing impurities in the material.

Example 31

Experiments were performed to explore whether the application of TEAL to dry Elevance-derived 9-DAME would allow for the use of lower catalyst loadings. Initial results, as shown in FIG. 1, indicated that TEAL did have a beneficial effect, although a large excess of TEAL negatively affected conversion. The removal of excess TEAL by adsorption onto Al$_2$O$_3$ was then explored.

Figure 2:
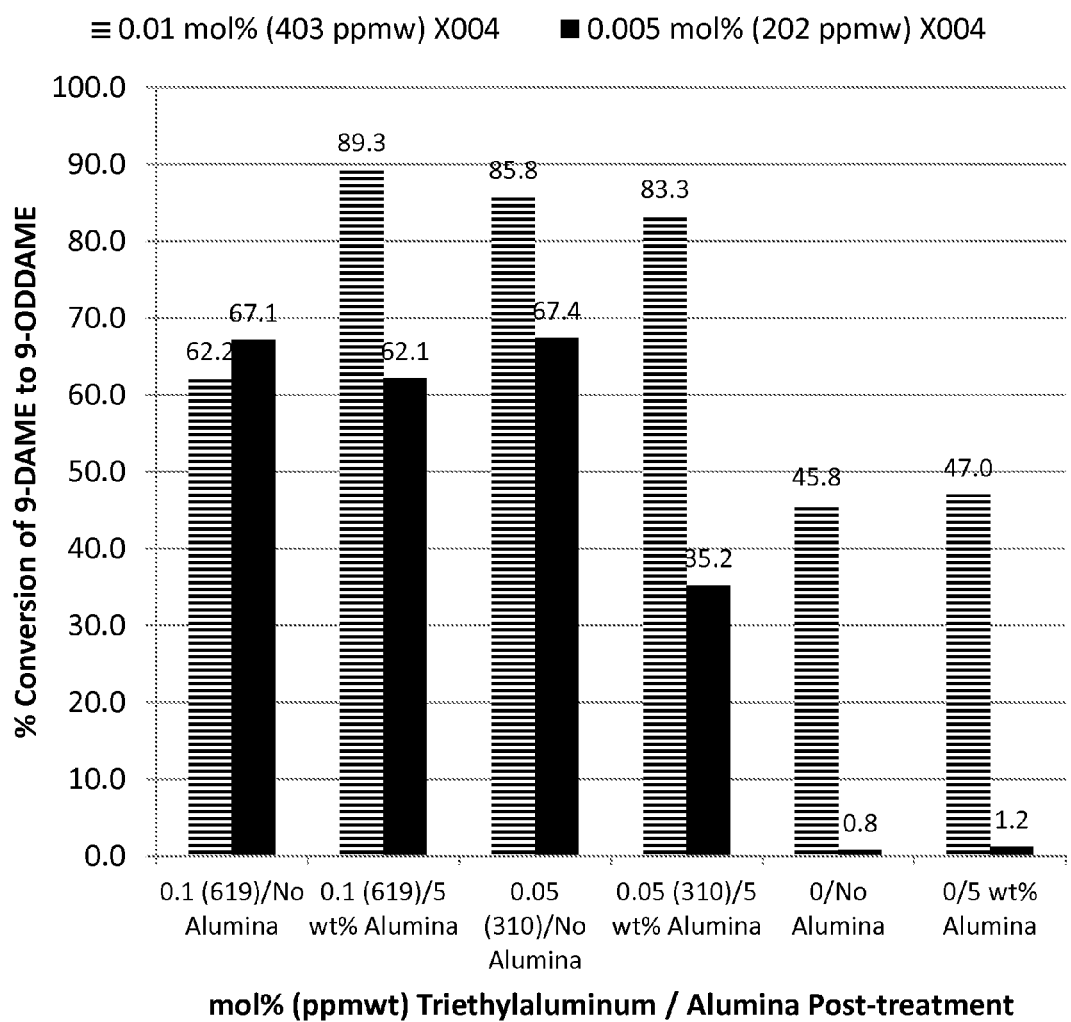
FIG. 2 is a chart showing the effect of an alumina post-treatment following a TEAL initial treatment in the purification of 9-DAME.

FIG. 2 displays screening data for TEAL treatment of dry Elevance-derived 9-DAME with and without alumina post-treatment. The procedure for these experiments was to treat 9-DAME with the specified amount of TEAL (as a 1.0 M solution in hexanes) for 30 minutes and then add 5 wt % of dry, activated neutral alumina and stir for an additional 30 minutes. The alumina was removed by filtration through a glass fiber filter. Two different TEAL loadings were tested- 620 and 310 ppmwt—as was a control to which no TEAL was added. The control reactions indicated that there was not a beneficial effect associated with treatment of the material with only alumina (the material had already been treated on a heat-treated alumina column).

Example 32

Figure 3:
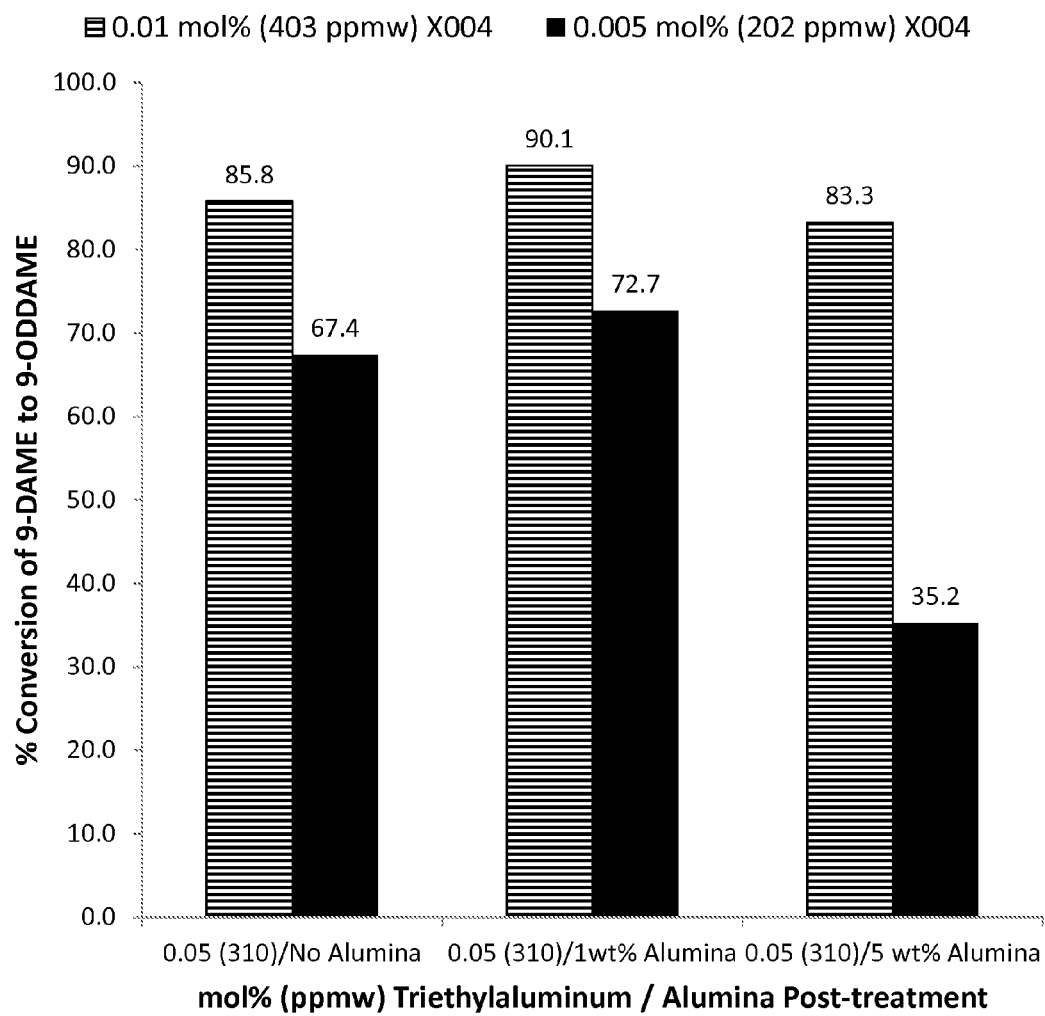
FIG. 3 is a chart showing the effect of varying the amount of alumina used for post-treatment after an initial TEAL treatment in the purification of 9-DAME.

FIG. 3 displays the effect of varying the amount of alumina used for the post-treatment of TEAL treated 9-DAME. The procedure for these experiments was to treat 9-DAME with the specified amount of TEAL (as a 1.0 M solution in hexanes) for 30 minutes and then add either 0 wt %, 1 wt %, or 5 wt % of dry, activated neutral alumina and stir for an additional 30 minutes. The alumina was removed by filtration through a glass fiber filter. The samples were then metathesized with either 403 or 202 ppmw of X004. It was found that an alumina treatment to remove unreacted TEAL (and/or possibly reaction products of TEAL with impurities) can be beneficial to catalyst efficiency.

Example 33

TEAL Treatment of 9-DAME on a 0.5 kg Scale

A 0.5-kg scale TEAL purification of 9-DAME was performed. After the material had been treated as outlined below, a 0.25 kg self-metathesis employing 200 ppm X004 was conducted as described in Example 18. After 4 hours, the conversion had reached 91.6%.

Treatment of dry (<10 ppm H$_2$O) 9-DAME with 310 ppm TEAL results in a threefold reduction in the necessary molybdenum catalyst (X004) required to achieve >90% conversion to 9-ODDAME (from 600 ppm to 200 ppm). It was found that an excess of TEAL (>10 molar equivalents) reduces catalyst efficiency and, consequently, passivation by adsorption on alumina is necessary. The pre-treatment has been scaled to 0.5 kg as described below.

In the glove box, 500 g 9-DAME (2.713 mol), which had previously been treated with heat-treated (375° C.) alumina and 4 Å molecular sieves (PV≈0; H₂O=4.9 ppm), was weighed into a 1-L round-bottomed flask equipped with a magnetic stir bar. To the stirring ester was added 1.36 mL of a 1.0 M solution of TEAL in hexanes (1.36 mmol; 0.05 mol %; 310 ppmwt). Stirring was continued for 1 hour and then 5 g (1 wt %) of neutral, activated alumina that had been dried at 250° C. in vacuo was added causing a small amount of gas to evolve. The mixture was stirred for another hour. The alumina was removed by filtration through a medium porosity sintered glass frit and then the purified ester was stored in a glass bottle.

Example 34

Self-metathesis of TEAL/Al₂O₃ treated 9-DAME by 200 ppmwt X004 on a 0.25 kg scale: In a N₂-filled glove box, 0.25 kg 9-DAME (vide supra) was weighed and transferred to a 1-L Schlenk flask equipped with a magnetic stir bar and an inlet adapter with a Teflon valve. A solution of 50.0 mg X004 in 1.5 mL toluene was prepared and transferred into a gas tight syringe. The flask was removed from the glove box and then connected to the Schlenk line and brought to 50° C. by immersion in a silicone oil bath. The X004 catalyst solution was then added to the ester under a flush of nitrogen. The mixture was then stirred at 50° C. opened to the Schlenk line silicone oil bubbler. Evolution of ethylene was observed immediately and continued for ~15 minutes. After gas evolution slowed, the inlet adapter connected to the Schlenk line nitrogen rail was closed and the headspace pressure was regulated to 200 torr by means of a digital vacuum regulator attached to the Schlenk line. The digital vacuum regulator was equipped with a ⅓ PSI relief valve that was vented to a silicone oil bubbler. After 2 hours gas evolution slowed again and the headspace pressure was regulated to 100 torr. After another hour (3 hours of reaction time), the flask was then opened to full vacuum and the pressure slowly dropped from 5 to 0.5 torr over the course of an hour. After a total of 4 hours, the flask was opened to air to quench the catalyst. Analysis of the mixture by GC-FID showed it to be 91.6% 9-ODDAME.

Example 35

According to analytical measurements, 9-DAME derived from a natural oil (hereto "crude" 9-DAME) was found to contain 268.9 ppmwt water which corresponds to 0.275 mole %, having peroxide value (PV, see above) as high as 3.0 meq/kg and para-anisidine value (pAV, see above) 9.6 meq/kg.

In order to lower the original water content of "crude" 9-DAME, it was treated with activated molecular sieves (10 wt %) for 24 h, wherein the water content decreased to 40 ppmwt. The drying process was repeated with another 10 wt % fresh activated molecular sieves. This procedure resulted in a 9-DAME (hereto "predried" 9-DAME) having water content 28 ppmwt and having PV lowered than the limit of detection (<0.001 mole %).

Compounds X051, X052, X123, and X154 refer to molybdenum and tungsten catalyst having the structures described in the detailed description part above.

Trioctyl aluminum (25% in n-hexane; Cat. #386553) (Oc₃Al), acetic anhydride (ACS reagent, Cat. #242845), Cu powder (Cat. #12806) and Mg turnings (Cat. #403148) were purchased from Sigma-Aldrich.

Molecular sieves (3 Å, beads, ~2 mm; Cat. #1.05704.1000), molecular sieves (3 Å, powder; Cat. #1.05706.0250), and aluminum oxide (basic, 0.063-0.200 mm; Cat. #1.01076.2000) were purchased from Merck. For activation, molecular sieves and alumina were heated at 300° C. under 1 mbar for 24 hours and let cool and stored under dry nitrogen atmosphere.

Figure 4:
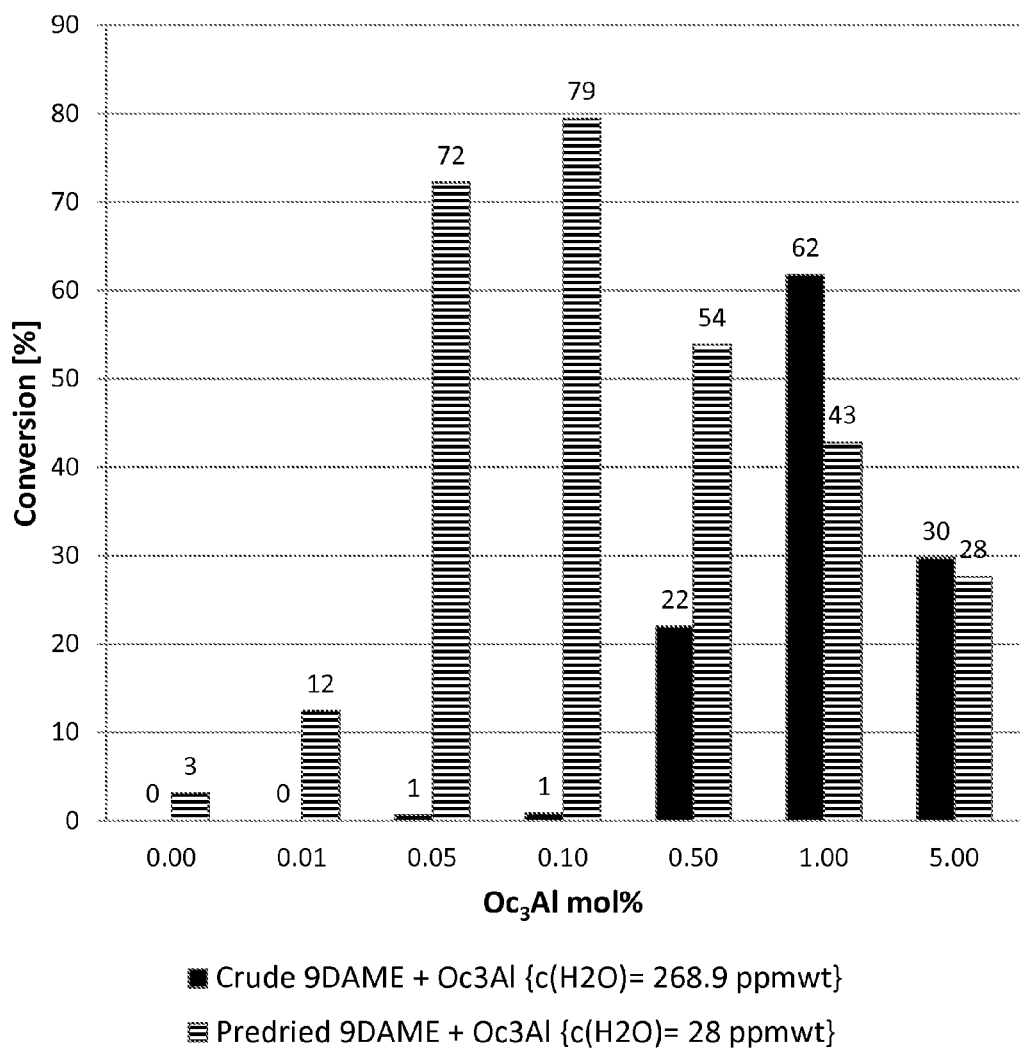
FIG. 4 is a chart showing the effect of various amounts of $Oc_3Al$ on the performance of Mo-catalyst X052 for "crude" and "predried" 9-DAME. Determination of the optimal amount of $Oc_3Al$ for both substrates.
Figure 5:
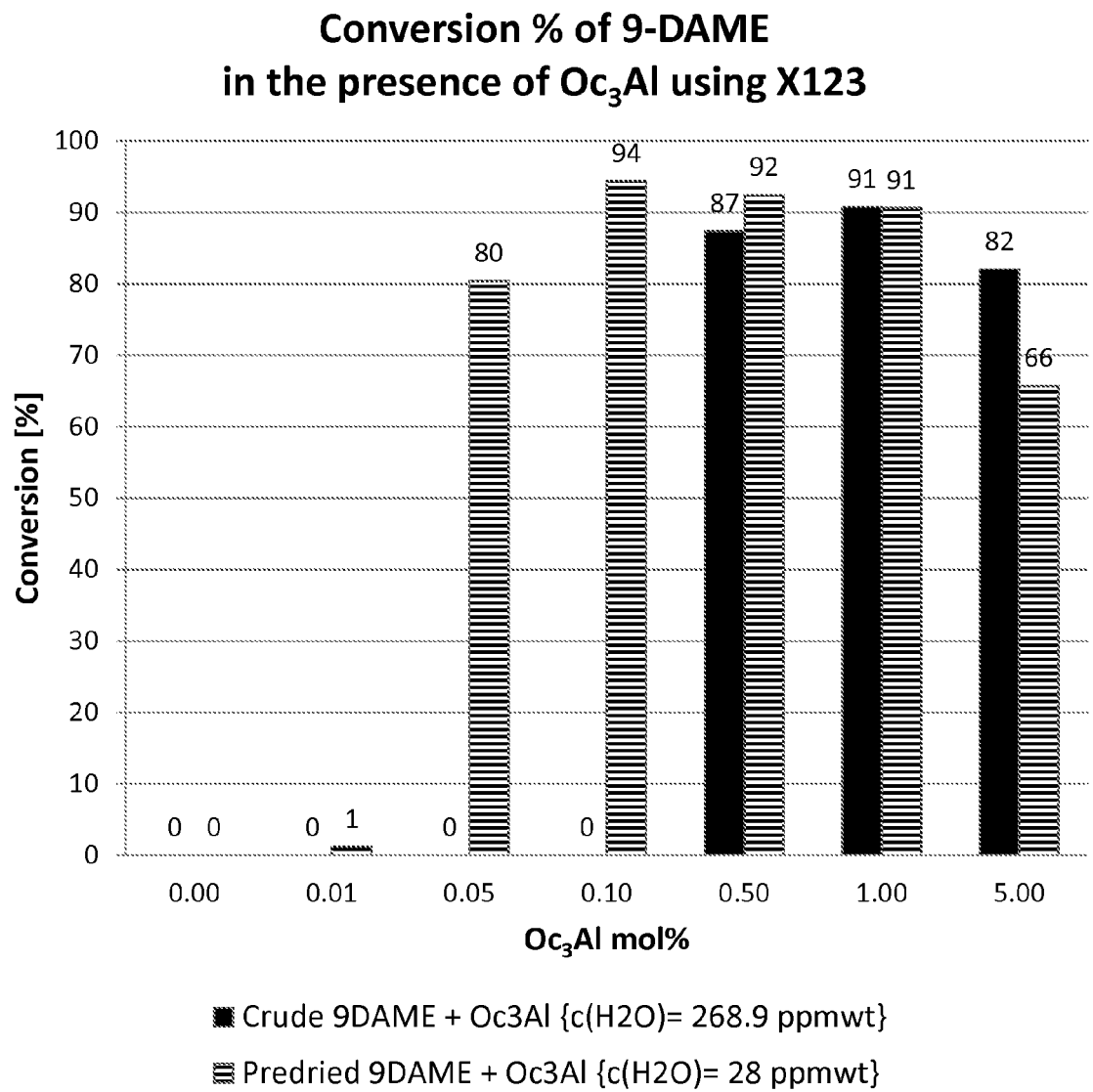
FIG. 5 is a chart showing the effect of various amounts of $Oc_3Al$ on the performance of W-catalyst X123 for "crude" and "predried" 9-DAME. Determination of the optimal amount of $Oc_3Al$ for both substrates.

Studies were conducted respectively on "crude" and "predried" 9-DAME samples in order to determine the optimally necessary amount of trioctyl aluminum used for compensation of the adverse effect of various impurities such as water, organic hydroperoxides, etc., at which the highest conversion can be reached in the metathesis reaction of these substrates. Results are shown in Table 34 and FIG. 4 for Mo-based catalyst X052 and in Table 35 and FIG. 5 for W-based complex X123. For "crude" 9-DAME, the use of 1.0 mol % Oc3Al gave the highest attainable conversion no matter whether Mo- or W-catalyst was applied, while for the "predried" substrate required only 0.1 mol % trioctyl aluminum for the optimal conversion, again in the case for each catalyst complex. Two more observations merit attention: (1) the "predried" substrates gave better conversion, and (2) the W-based catalyst X123 gave higher conversion than the Mo-based X052 catalyst.

0.0-5.0 mol % Oc₃Al:

All manipulation was performed under the inert atmosphere of a glove-box filled with nitrogen. In a 10 mL vented vial to "crude" 9-DAME (ERS 345-103) or "predried" 9-DAME (E01GBE387_2), the necessary amount of Oc₃Al was added at 25° C. and the reaction mixture was stirred for 20 h before 10 μL (0.1M) stock solution of the catalyst (X052, X01ABI331) was added and the reaction mixture was stirred at 25° C. and 1 atm for further 4 h. Then, the mixture was chambered out and quenched with wet EtOAc. Internal standards 1.0 mL pentadecane in EtOAc (c=60.40 mg/mL) and 1.0 mL mesitylene in EtOAc (c=60.20 mg/mL) were added and the reaction mixture was completed to 10 mL with ethyl acetate. From the obtained stock solution of the reaction, 1.0 mL was poured onto the top of a silica column (1.0 mL) and eluted with ethyl acetate (10 mL). From the collected elute, 100 μL was diluted to 1.0 mL form which 1.0 μL is injected and analyzed by GCMS-GCFID. Results are shown in Table 34 and FIG. 4.

TABLE 34

| Entry | Lot No. | Substrate | Cat. No. | Substr./Cat. | Oc3Al [mol %] | Conv. [%] | $Y_{9ODDAME}$ [%] | TON | E/Z |
|---|---|---|---|---|---|---|---|---|---|
| 1 | E01GBE491 | ERS: 345-103 | X052 | 10000 | 0.00 | 0 | 0 | 0 | — |
| 2 | E01GBE492 | ERS: 345-103 | X052 | 10000 | 0.01 | 0 | 0 | 0 | — |
| 3 | E01GBE493 | ERS: 345-103 | X052 | 10000 | 0.05 | 1 | 1 | 33 | 31/69 |
| 4 | E01GBE494 | ERS: 345-103 | X052 | 10000 | 0.10 | 1 | 1 | 42 | 27/73 |
| 5 | E01GBE495 | ERS: 345-103 | X052 | 10000 | 0.50 | 22 | 22 | 1099 | 18/82 |
| 6 | E01GBE496 | ERS: 345-103 | X052 | 10000 | 1.00 | 62 | 62 | 3088 | 18/82 |
| 7 | E01GBE497 | ERS: 345-103 | X052 | 10000 | 5.00 | 30 | 30 | 1486 | 19/81 |
| 8 | E01GBE498 | E01GBE387_2 | X052 | 10000 | 0.00 | 3 | 3 | 156 | 23/77 |
| 9 | E01GBE499 | E01GBE387_2 | X052 | 10000 | 0.01 | 12 | 12 | 623 | 20/80 |

TABLE 34-continued

| Entry | Lot No. | Substrate | Cat. No. | Substr./Cat. | Oc3Al [mol %] | Conv. [%] | $Y_{9ODDAME}$ [%] | TON | E/Z |
|---|---|---|---|---|---|---|---|---|---|
| 10 | E01GBE500 | E01GBE387_2 | X052 | 10000 | 0.05 | 72 | 72 | 3612 | 17/83 |
| 11 | E01GBE501 | E01GBE387_2 | X052 | 10000 | 0.10 | 79 | 79 | 3974 | 17/83 |
| 12 | E01GBE502 | E01GBE387_2 | X052 | 10000 | 0.50 | 54 | 54 | 2692 | 18/82 |
| 13 | E01GBE503 | E01GBE387_2 | X052 | 10000 | 1.00 | 43 | 43 | 2141 | 20/80 |
| 14 | E01GBE504 | E01GBE387_2 | X052 | 10000 | 5.00 | 28 | 28 | 1381 | 19/81 |

0.0-5.0 mol % $Oc_3Al$:

All manipulation was performed under the inert atmosphere of a glove-box filled with nitrogen. In a 10 mL vented vial to "crude" 9-DAME (ERS 345-103) or "predried" 9-DAME (E01GBE387_2), the necessary amount of $Oc_3Al$ was added at 25° C. and the reaction mixture was stirred for 20 h before 10 μL (0.1M) stock solution of the catalyst (X123, X01FTH333) was added and the reaction mixture was stirred at 25° C. and 1 atm for further 4 h. Then, the mixture was chambered out and quenched with wet EtOAc. Internal standards 1.0 mL pentadecane in EtOAc (c=60.44 mg/mL) and 1.0 mL mesitylene in EtOAc (c=60.48 mg/mL) were added and the reaction mixture was completed to 10 mL with ethyl acetate. From the obtained stock solution of the reaction, 1.0 mL was poured onto the top of a silica column (1.0 mL) and eluted with ethyl acetate (10 mL). From the collected elute, 100 μL was diluted to 1.0 mL form which 1.0 μL is injected and analyzed by GCMS-GCFID. Results are shown in Table 35 and FIG. 5.

TABLE 35

| Entry | Lot No. | Substrate | Cat. No. | Substr./Cat. | Oc3Al [mol %] | Conv. [%] | $Y_{9ODDAME}$ [%] | TON | E/Z |
|---|---|---|---|---|---|---|---|---|---|
| 1 | E01GBE477 | ERS: 345-103 | X123 | 10000 | 0.00 | 0 | 0 | 0 | — |
| 2 | E01GBE478 | ERS: 345-103 | X123 | 10000 | 0.01 | 0 | 0 | 0 | — |
| 3 | E01GBE479 | ERS: 345-103 | X123 | 10000 | 0.05 | 0 | 0 | 0 | — |
| 4 | E01GBE480 | ERS: 345-103 | X123 | 10000 | 0.10 | 0 | 0 | 0 | — |
| 5 | E01GBE481 | ERS: 345-103 | X123 | 10000 | 0.50 | 87 | 87 | 4373 | 22/78 |
| 6 | E01GBE482 | ERS: 345-103 | X123 | 10000 | 1.00 | 91 | 91 | 4538 | 20/80 |
| 7 | E01GBE483 | ERS: 345-103 | X123 | 10000 | 5.00 | 82 | 82 | 4104 | 24/76 |
| 8 | E01GBE484 | E01GBE387_2 | X123 | 10000 | 0.00 | 0 | 0 | 0 | — |
| 9 | E01GBE485 | E01GBE387_2 | X123 | 10000 | 0.01 | 1 | 1 | 59 | 39/61 |
| 10 | E01GBE486 | E01GBE387_2 | X123 | 10000 | 0.05 | 80 | 80 | 4021 | 24/76 |
| 11 | E01GBE487 | E01GBE387_2 | X123 | 10000 | 0.10 | 94 | 94 | 4719 | 20/80 |
| 12 | E01GBE488 | E01GBE387_2 | X123 | 10000 | 0.50 | 92 | 92 | 4624 | 21/79 |
| 13 | E01GBE489 | E01GBE387_2 | X123 | 10000 | 1.00 | 91 | 91 | 4531 | 22/78 |
| 14 | E01GBE490 | E01GBE387_2 | X123 | 10000 | 5.00 | 66 | 66 | 3287 | 26/74 |

Example 36

Experiments were performed to discover whether the application of 3.0 wt % activated alumina ($Al_2O_3$) after initial 1.0 mol % $Oc_3Al$ treatment of "crude" 9-DAME would be beneficial and result in higher conversion using Mo-based X051 or W-based X154 catalyst in the metathesis reaction of the substrate. The results obtained were compared with a similar experiment in which 1.0 mol % $Oc_3Al$ was used alone as pretreatment agent. The results are shown in Table 36 and FIG. 6 for catalyst X051 and in Table 37 and FIG. 7 for catalyst X154.

Figure 6:
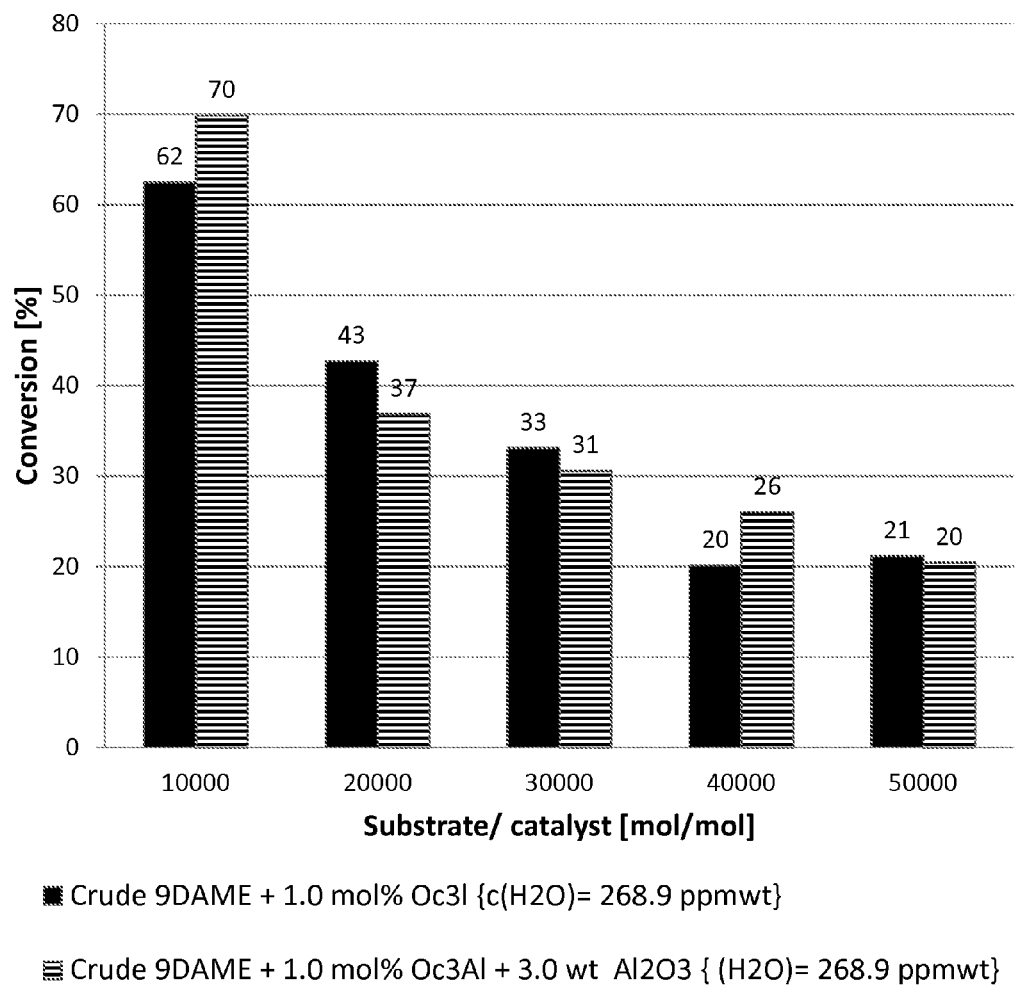
FIG. 6 is a chart showing the effect of 3 wt % alumina post-treatment following an $Oc_3Al$ initial treatment in the purification of "crude" 9-DAME at various X051 Mo-catalyst loading.
Figure 7:
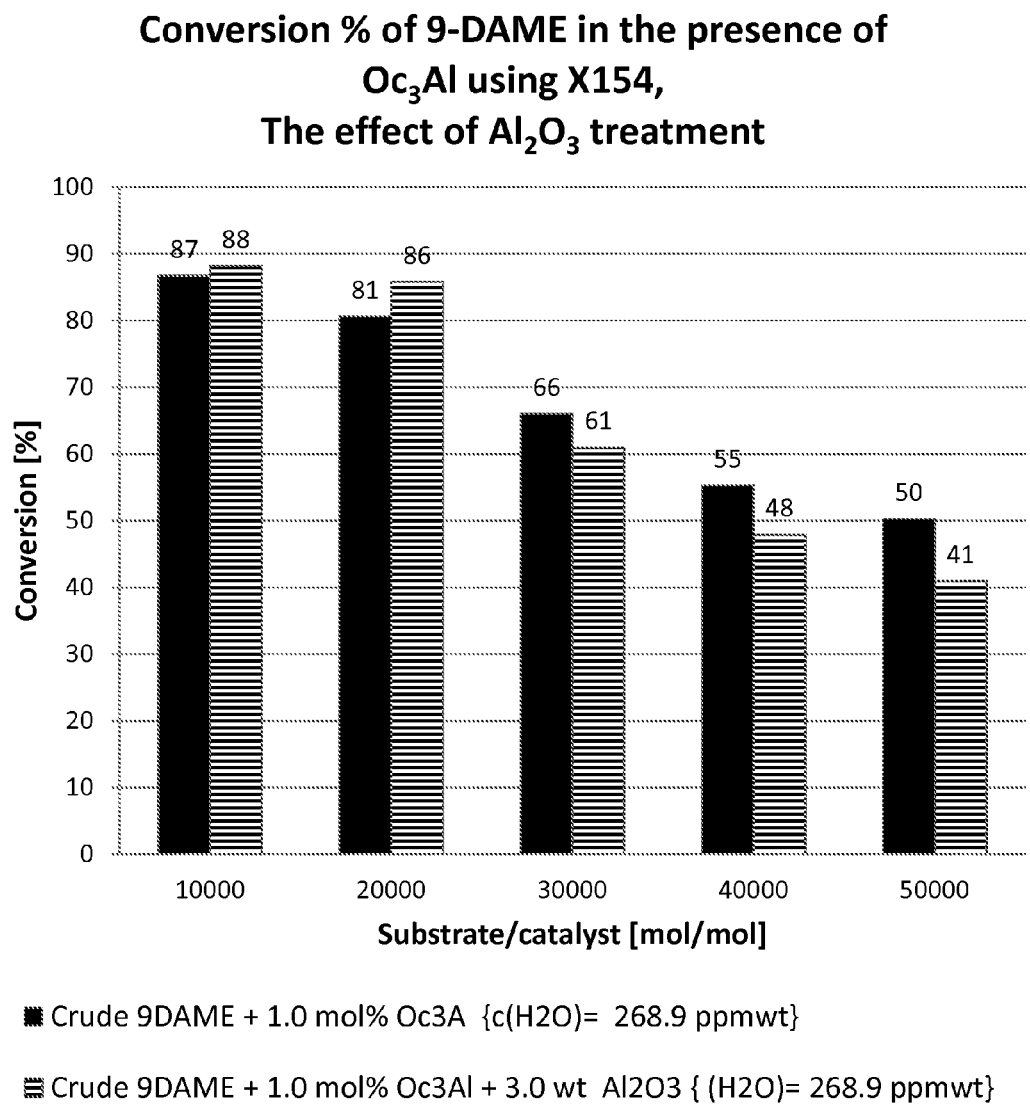
FIG. 7 is a chart showing the effect of 3 wt % alumina post-treatment following an $Oc_3Al$ initial treatment in the purification of "crude" 9-DAME at various X154 W-catalyst loading.

1.0 mol % $Oc_3Al$:

All manipulation was performed under the inert atmosphere of a glove-box filled with nitrogen. In a 10 mL vented vial to "crude" 9-DAME (ERS:345-103) at 25° C., 1.0 mol % $Oc_3Al$ was added and the reaction mixture was stirred at ambient temperature for 20 h before 10 μL (0.1M) stock solution of the catalyst (X051 or X154) was added and the reaction mixture was stirred at 25° C. and 1 atm for further 4 h. Then, the mixture was chambered out and quenched with wet EtOAc. Internal standards 1.0 mL pentadecane in EtOAc (c=60.08 mg/mL) and 1.0 mL mesitylene in EtOAc (c=61.84 mg/mL) were added and the reaction mixture was completed to 10 mL with ethyl acetate from which 1.0 mL was poured onto the top of a silica column (1.0 mL) and eluted with ethyl acetate (10 mL). From the collected elute, 100 μL was diluted to 1.0 mL form which 1.0 μL was injected and analyzed by GCMS-GCFID. Results are shown in Tables 36 and 37 (FIGS. 6 and 7).

1.0 mol % $Oc_3Al$ + 3 wt % $Al_2O_3$:

All manipulation was performed under the inert atmosphere of the Glove-Box filled with nitrogen. To "crude" 9-DAME (ERS:345-103) at 25° C. 1.0 mol %, $Oc_3Al$ was added and the reaction mixture was stirred at ambient temperature for 20 h. Then 3.0 wt % activated alumina was added and the reaction mixture was stirred for 2 h before the alumina was filtered off. In a 10 mL vented vial to the aliquot amount of the filtrate 10 μL (0.1M) stock solution of the catalyst (X051, X01ERE220) was added and the reaction mixture was stirred at 25° C. and 1 atm for further 4 h. Then, the mixture was chambered out and quenched with wet EtOAc. Internal standards 1.0 mL pentadecane in EtOAc (c=60.08 mg/mL) and 1.0 mL mesitylene in EtOAc (c=61.84 mg/mL) were added and the reaction mixture was completed to 10 mL with ethyl acetate from which 1.0 mL was poured onto the top of a silica column (1.0 mL) and eluted with ethyl acetate (10 mL). From the collected elute 100 μL was diluted to 1.0 mL form which 1.0 μL was injected and analyzed by GCMS-GCFID. Results are shown in Table 36 and 37 (FIGS. 6 and 7).

TABLE 36

| Entry | Lot No. | Substrate | Cat. No. | Substr./Cat. | act. Al2O3 [wt %] | Conv. [%] | $Y_{9ODDAME}$ [%] | TON | E/Z |
|---|---|---|---|---|---|---|---|---|---|
| 1 | E01GBE512 | ERS: 345-103 | X051 | 10000 | 0 | 62 | 62 | 3124 | 12/88 |
| 2 | E01GBE513 | ERS: 345-103 | X051 | 20000 | 0 | 43 | 43 | 4269 | 11/89 |
| 3 | E01GBE514 | ERS: 345-103 | X051 | 30000 | 0 | 33 | 33 | 4962 | 11/89 |
| 4 | E01GBE515 | ERS: 345-103 | X051 | 40000 | 0 | 20 | 20 | 4025 | 12/88 |
| 5 | E01GBE516 | ERS: 345-103 | X051 | 50000 | 0 | 21 | 21 | 5288 | 12/88 |
| 6 | E01GBE517 | ERS: 345-103 | X051 | 10000 | 3.00 | 70 | 70 | 3494 | 12/88 |
| 7 | E01GBE518 | ERS: 345-103 | X051 | 20000 | 3.00 | 37 | 37 | 3684 | 12/88 |
| 8 | E01GBE519 | ERS: 345-103 | X051 | 30000 | 3.00 | 31 | 31 | 4587 | 13/87 |
| 9 | E01GBE520 | ERS: 345-103 | X051 | 40000 | 3.00 | 26 | 26 | 5201 | 13/87 |
| 10 | E01GBE521 | ERS: 345-103 | X051 | 50000 | 3.00 | 20 | 20 | 5107 | 14/86 |

TABLE 37

| Entry | Lot No. | Substrate | Cat. No. | Substr./Cat. | act. Al2O3 [wt %] | Conv. [%] | $Y_{9ODDAME}$ [%] | TON | E/Z |
|---|---|---|---|---|---|---|---|---|---|
| 1 | E01GBE522 | ERS: 345-103 | X154 | 10000 | 0.00 | 87 | 87 | 4336 | 17/83 |
| 2 | E01GBE523 | ERS: 345-103 | X154 | 20000 | 0.00 | 81 | 81 | 8065 | 20/80 |
| 3 | E01GBE524 | ERS: 345-103 | X154 | 30000 | 0.00 | 66 | 66 | 9909 | 21/79 |
| 4 | E01GBE525 | ERS: 345-103 | X154 | 40000 | 0.00 | 55 | 55 | 11066 | 21/79 |
| 5 | E01GBE526 | ERS: 345-103 | X154 | 50000 | 0.00 | 50 | 50 | 12568 | 21/79 |
| 6 | E01GBE527 | ERS: 345-103 | X154 | 10000 | 3.00 | 88 | 88 | 4411 | 17/83 |
| 7 | E01GBE528 | ERS: 345-103 | X154 | 20000 | 3.00 | 86 | 86 | 8577 | 19/81 |
| 8 | E01GBE529 | ERS: 345-103 | X154 | 30000 | 3.00 | 61 | 61 | 9151 | 20/80 |
| 9 | E01GBE530 | ERS: 345-103 | X154 | 40000 | 3.00 | 48 | 48 | 9586 | 21/79 |
| 10 | E01GBE531 | ERS: 345-103 | X154 | 50000 | 3.00 | 41 | 41 | 10238 | 21/79 |

Example 37

Figure 8:
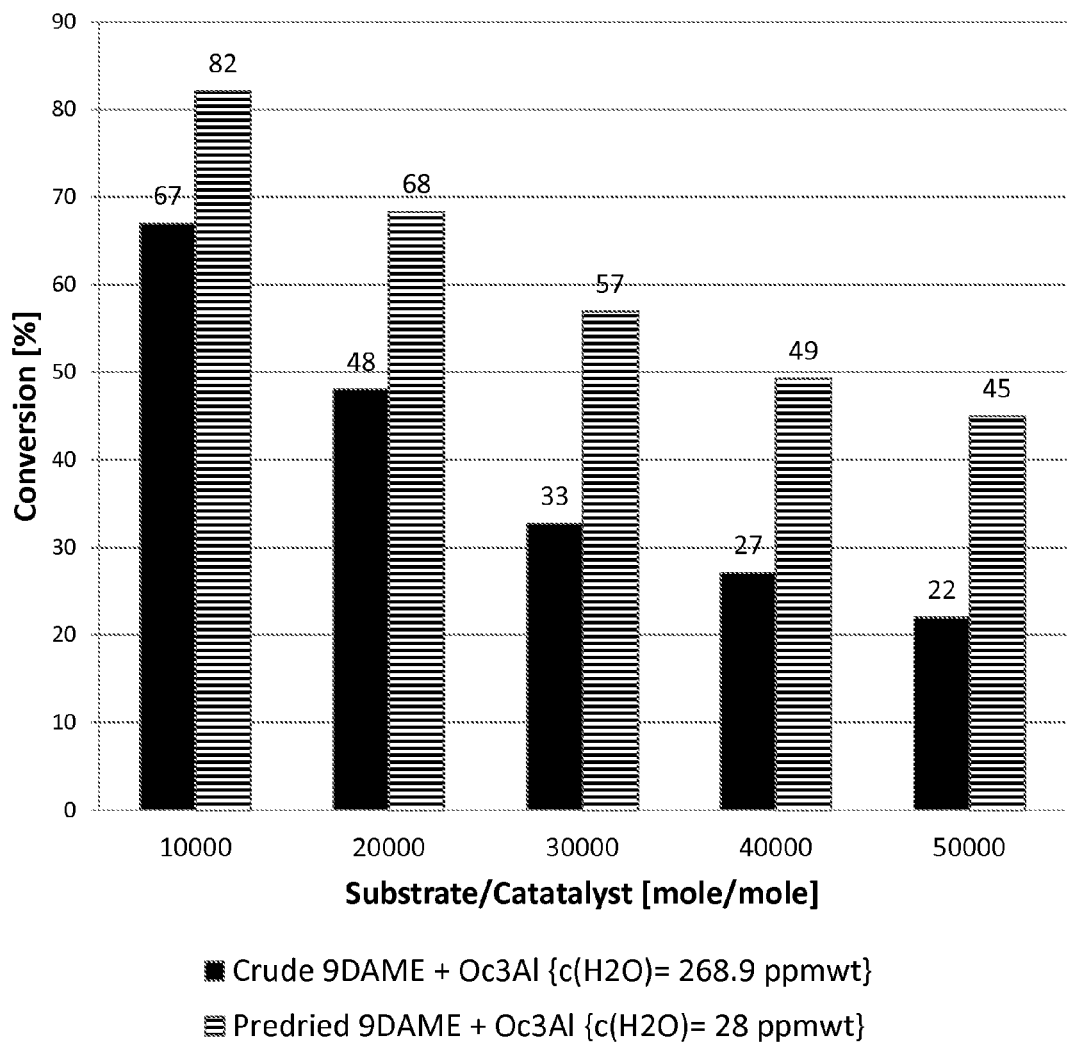
FIG. 8 is a chart showing conversion % as a function of substrate to catalyst ratio using Mo-catalyst X052 in case of "crude" and "predried" 9-DAME.
Figure 9:
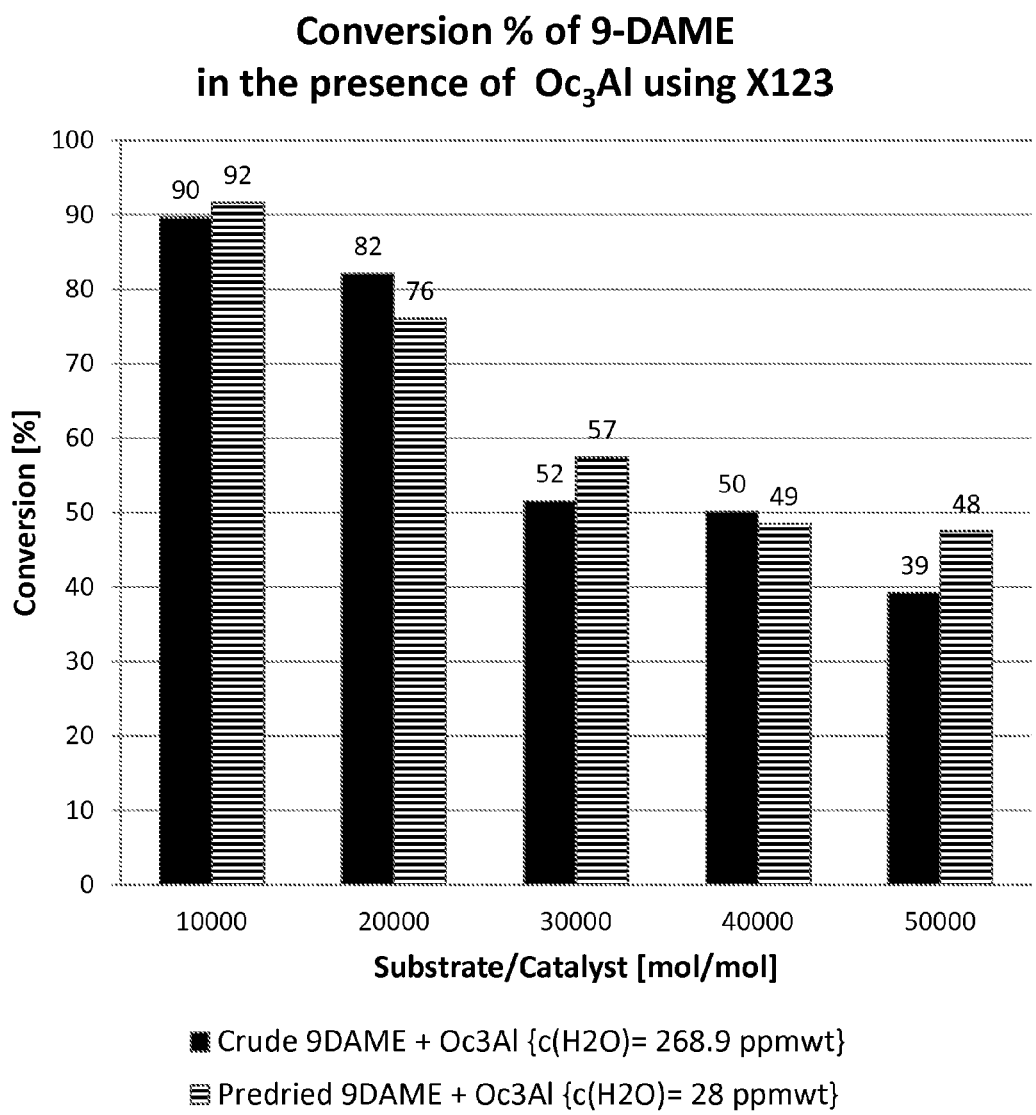
FIG. 9 is a chart showing conversion % as a function of substrate to catalyst ratio using W-catalyst X123 in case of "crude" and "predried" 9-DAME.

In this example, the effect of the amount of a catalyst loading was studied for Mo-based X052 and W-based X123 metathesis catalysts. As described in detail below, the metathesis reactions were conducted at 25° C. for 4 hours at atmospheric pressure. The results are shown in FIG. 8 in case of catalyst X052 and in FIG. 9 in case of X123 catalyst. The results show that the catalyst loading could have been lowered to as low as 20 ppmwt while still having considerable conversion detected. The results show that the use of "predried" 9-DAME was more favorable compared to the "crude" 9-DAME, and the X123 W-based catalyst provided higher conversion than its X052 Mo-centered analog in all cases.

1.0 mol % v. 0.1 mol Oc₃Al with X052:

All manipulation was performed under the inert atmosphere of a glove-box filled with nitrogen. In a 10 mL vented vial to "crude" 9-DAME (ERS:345-103 or E01GBE387_2) at 25° C., 1.0 mol % or 0.1 mol % Oc₃Al was added and the reaction mixture was stirred at 25° C. for 20 h before 10 μL (1.0M) stock solution of the catalyst (X052, X01ABI385) was added and the reaction mixture was stirred at 25° C. and 1 atm for further 4 h. Then, the mixture was chambered out and quenched with wet EtOAc. Internal standards 1.0 mL pentadecane in EtOAc (c=60.08 mg/mL) and 1.0 mL mesitylene in EtOAc (c=60.48 mg/mL) were added and the reaction mixture was completed to 10 mL with ethyl acetate from which 1.0 mL was poured onto the top of a silica column (1.0 mL) and eluted with ethyl acetate (10 mL). From the collected elute, 100 μL was diluted to 1.0 mL form which 1.0 μL was injected and analyzed by GCMS-GCFID. Results are collected in Table 38 and FIG. 8.

TABLE 38

| Entry | Lot No. | Substrate | Cat. No. | Substr./Cat. | Oc3Al [mol %] | Conv. [%] | $Y_{9ODDAME}$ [%] | TON | E/Z |
|---|---|---|---|---|---|---|---|---|---|
| 1 | E01GBE532 | ERS: 345-103 | X052 | 10000 | 1.00 | 67 | 67 | 3350 | 17/83 |
| 2 | E01GBE533 | ERS: 345-103 | X052 | 20000 | 1.00 | 48 | 48 | 4802 | 17/83 |
| 3 | E01GBE534 | ERS: 345-103 | X052 | 30000 | 1.00 | 33 | 33 | 4905 | 18/82 |
| 4 | E01GBE535 | ERS: 345-103 | X052 | 40000 | 1.00 | 27 | 27 | 5417 | 18/82 |
| 5 | E01GBE536 | ERS: 345-103 | X052 | 50000 | 1.00 | 22 | 22 | 5504 | 18/82 |
| 6 | E01GBE550 | E01GBE387_2 | X052 | 10000 | 0.10 | 82 | 82 | 4104 | 16/84 |
| 7 | E01GBE551 | E01GBE387_2 | X052 | 20000 | 0.10 | 68 | 68 | 6831 | 17/83 |
| 8 | E01GBE534 | E01GBE387_2 | X052 | 30000 | 0.10 | 57 | 57 | 8541 | 18/82 |
| 9 | E01GBE535 | E01GBE387_2 | X052 | 40000 | 0.10 | 49 | 49 | 9850 | 17/83 |
| 10 | E01GBE536 | E01GBE387_2 | X052 | 50000 | 0.10 | 45 | 45 | 11246 | 17/83 |

1.0 mol % v. 0.1 mol % Oc₃Al with X123:

All manipulation was performed under the inert atmosphere of the Glove-Box filled with nitrogen. In a 10 mL vented vial to "crude" 9-DAME (ERS:345-103 or E01GBE387_2) at 25° C., 1.0 mol % or 0.1 mol % Oc₃Al was added and the reaction mixture was stirred at 25° C. for 20 h before 10 μL (1.0M) stock solution of the catalyst (X123, X01FTH344) was added and the reaction mixture was stirred at 25° C. and 1 atm for further 4 h. Then, the mixture was chambered out and quenched with wet EtOAc. Work-up: Internal standards 1.0 mL pentadecane in EtOAc (c=60.08 mg/mL) and 1.0 mL mesitylene in EtOAc (c=60.48 mg/mL) were added and the reaction mixture was completed to 10 mL with ethyl acetate from which 1.0 mL was poured onto the top of a silica column (1.0 mL) and eluted with ethyl acetate (10 mL). From the collected elute, 100 µL was diluted to 1.0 mL form which 1.0 µL was injected and analyzed by GCMS-GCFID. Results are collected in Table 39 and FIG. 9.

TABLE 39

| Entry | Lot No. | Substrate | Cat. No. | Substr./Cat. | Oc3Al [mol %] | Conv. [%] | $Y_{9ODDAME}$ [%] | TON | E/Z |
|---|---|---|---|---|---|---|---|---|---|
| 1 | E01GBE537 | ERS: 345-103 | X123 | 10000 | 1.00 | 90 | 90 | 4484 | 21/79 |
| 2 | E01GBE538 | ERS: 345-103 | X123 | 20000 | 1.00 | 82 | 82 | 8213 | 23/77 |
| 3 | E01GBE539 | ERS: 345-103 | X123 | 30000 | 1.00 | 52 | 52 | 7733 | 26/74 |
| 4 | E01GBE540 | ERS: 345-103 | X123 | 40000 | 1.00 | 50 | 50 | 10034 | 26/74 |
| 5 | E01GBE541 | ERS: 345-103 | X123 | 50000 | 1.00 | 39 | 39 | 9814 | 27/73 |
| 6 | E01GBE555 | E01GBE387_2 | X123 | 10000 | 0.10 | 92 | 92 | 4583 | 20/80 |
| 7 | E01GBE556 | E01GBE387_2 | X123 | 20000 | 0.10 | 76 | 76 | 7612 | 23/77 |
| 8 | E01GBE557 | E01GBE387_2 | X123 | 30000 | 0.10 | 57 | 57 | 8621 | 25/75 |
| 9 | E01GBE558 | E01GBE387_2 | X123 | 40000 | 0.10 | 49 | 49 | 9702 | 26/74 |
| 10 | E01GBE559 | E01GBE387_2 | X123 | 50000 | 0.10 | 48 | 48 | 11884 | 26/74 |

Example 38

Figure 10:
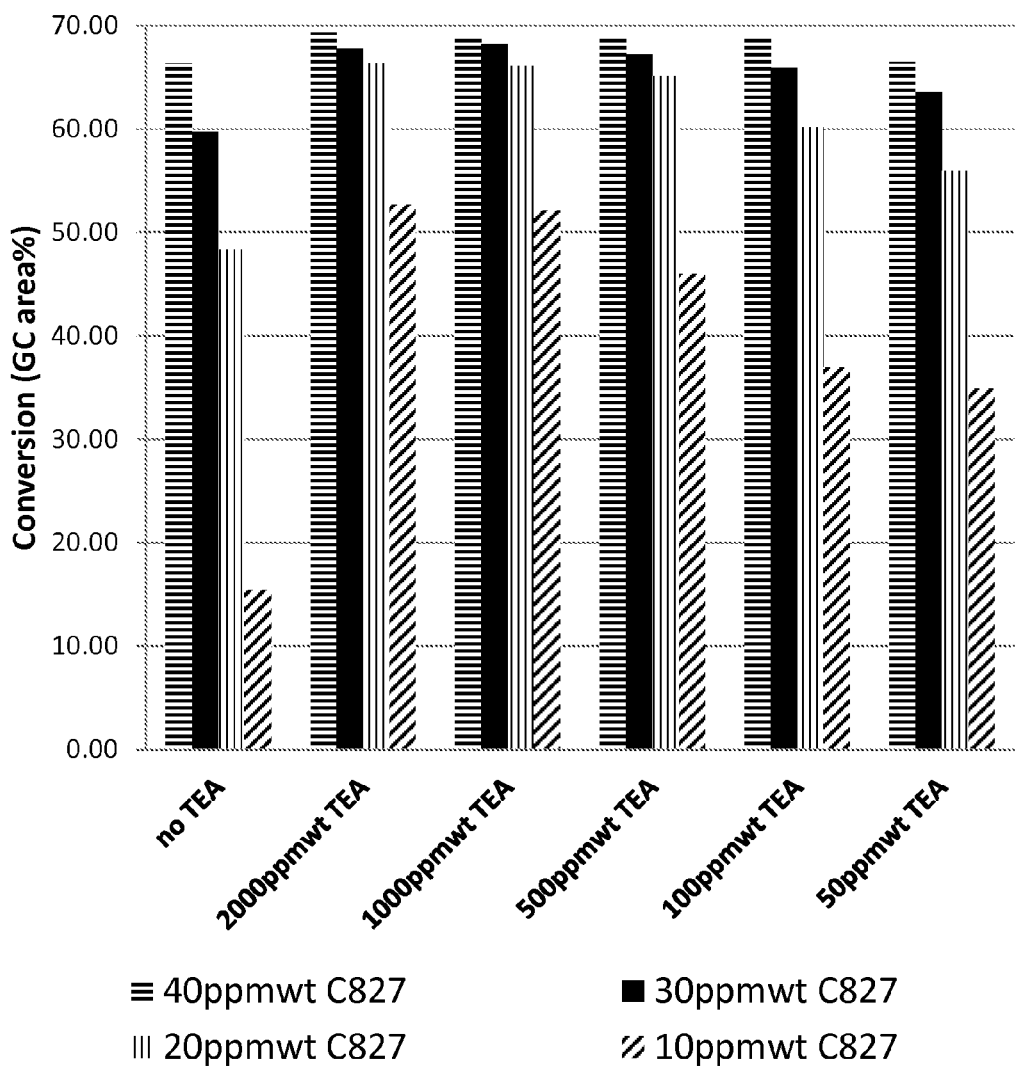
FIG. 10 is a chart showing self-metathesis conversion % for soybean oil as a function of catalyst loading and TEAL treatment.

Self-metathesis experiments of soybean oil (Costco) were carried out using 40, 30, 20, or 10 ppmwt of Ru catalyst [1,3-Bis-(2,4,6-trimethylphenyl)-2-imidazolidinylidene] dichloro ruthenium(3-methyl-2-butenylidene)(tricyclohexylphosphine) (C827, Materia) after treating the oil samples with between 0 and 2000 ppmwt TEAL at 60° C. for ca. 20 minutes. The TEAL treatment occurred after the oil was sparged with nitrogen and heated for 2 hours at 200° C. After the metathesis reactions were allowed to proceed for 3 hours, aliquots of the product mixtures were analyzed by gas chromatographic analysis (following transesterification with 1% w/w NaOMe in methanol at 60° C.) to determine the extent of conversion of oleate+linoleate+linolinate. FIG. 10 shows that improved conversions were achieved at 40, 30, 20, and 10 ppmwt C827 when the oil was treated with between 50 and 2000 ppmwt TEAL versus the conversions achieved with the same levels of C827 catalyst when no TEAL was employed.

The products were characterized by comparing peaks with known standards. Fatty acid methyl ester (FAME) analyses were performed using an Agilent 6850 instrument and the following conditions:
Column: J&W Scientific, DB-Wax, 30 m×0.32 mm (ID)× 0.5 µm film thickness
Injector temperature: 250° C.
Detector temperature: 300° C.
Oven temperature: 70° C. starting temperature, 1 minute hold time, ramp rate 20° C./min to 180° C., ramp rate 3° C./min to 220° C., 10 minute hold time
Carrier gas: Hydrogen
Flow rate: 1.0 mL/min The entire contents of each and every patent and non-patent publication cited herein are hereby incorporated by reference, except that in the event of any inconsistent disclosure or definition from the present specification, the disclosure or definition herein shall be deemed to prevail.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A method of chemically treating a metathesis substrate, comprising:
   providing a composition comprising a metathesis substrate and one or more catalyst poisoning contaminants, wherein the metathesis substrate is a natural oil; and
   treating the composition to reduce the concentration of at least one of the one or more catalyst poisoning contaminants in the composition;
   wherein the treating comprises contacting the composition with a metal alkyl compound.

2. The method of claim 1, wherein the natural oil comprises a vegetable oil, an algae oil, a fish oil, an animal fat, a tall oil, any derivatives of the foregoing, or any combinations thereof.

3. The method of claim 1, wherein the vegetable oil comprises canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, camelina oil, castor oil, or combinations thereof.

4. The method of claim 1, wherein the metathesis substrate comprises a fatty acid monoacylglyceride, a fatty acid diacylglyceride, a fatty acid triacylglyceriode, or a combination thereof.

5. The method of claim 1, wherein the metathesis substrate comprises a fatty acid methyl ester.

6. The method of claim 1, wherein the catalyst poisoning contaminants comprise water, peroxides, peroxide decomposition products, hydroperoxides, protic materials, polar materials, Lewis base catalyst poisons, or combinations thereof.

7. The method of claim 1, wherein the catalyst poisoning contaminants comprise peroxides.

8. The method of claim 1, wherein the catalyst poisoning contaminants comprise oxygenates.

9. The method of claim 1, wherein the catalyst poisoning contaminants comprise compounds selected from the group consisting of alcohols, aldehydes, ethers, and combinations thereof.

10. The method of claim 1, wherein the catalyst poisoning contaminants comprise aldehydes.

11. The method of claim 1, wherein the metal alkyl compound is selected from the group consisting of: Group I metal alkyl compounds, Group II metal alkyl compounds, Group IIIA metal alkyl compounds, and any combinations thereof.

12. The method of claim 1, wherein the metal alkyl compound is a compound of formula:

$$MR_m,$$

wherein:
M is a Group II metal or a Group IIIA metal;
each R is independently an alkyl group having 1 to 20 carbon atoms; and
m is 2 if M is a Group II metal, and is 3 if M is a Group IIIA metal.

13. The method of claim 12, wherein M is magnesium, calcium, aluminum, or gallium.

14. The method of claim 12, wherein M is aluminum.

15. The method of claim 12, wherein each R is independently methyl, ethyl, butyl, hexyl, decyl, tetradecyl, or eicosyl.

16. The method of claim 1, wherein the metal alkyl compound is selected from the group consisting of: $Mg(CH_3)_2$, $Mg(C_2H_3)_2$, $Mg(C_2H_5)(C_4H_9)$, $Mg(C_4H_9)_2$, $Mg(C_6H_{13})_2$, $Mg(C_{12}H_{25})_2$, $Zn(CH_3)_2$, $Zn(C_2H_5)_2$, $Zn(C_4H_9)_2$, $Zn(C_4H_9)(C_8H_{17})$, $Zn(C_6H_{13})_2$, $Zn(C_6H_{13})_2$, $Al(C_2H_5)_3$, $Al(CH_3)_3$, $Al(n-C_4H_9)_3$, $Al(C_8H_{17})_3$, $Al(iso-C_4H_9)_3$, $Al(C_{12}H_{25})_3$, and combinations thereof.

17. The method of claim 16, wherein metal alkyl compound is selected from the group consisting of: $Al(C_2H_5)_3$, $Al(C_8H_{17})_3$, and combinations thereof.

18. The method of claim 1, wherein the metal alkyl compound is a metal alkyl compound comprising one or more halogen or hydride groups.

19. The method of claim 18, wherein the metal alkyl compound is ethylaluminum dichloride, diethylaluminum chloride, diethylaluminum hydride, Grignard reagents, diisobutylaluminum hydride, or combinations thereof.

20. The method of claim 1, wherein the metal alkyl compound is a trialkyl aluminum compound, and wherein the treating comprises contacting the metathesis substrate with one or more of the materials selected from the group consisting of: a molecular sieve, alumina, silica gel, montmorillonite clay, fuller's earth, bleaching clay, diatomaceous earth, a zeolite, kaolin, an activated metal, an acid anhydride, activated carbon, doda ash, a metal anhydride, a metal sulfate, a metal halide, a metal carbonate, a metal silicate, phosphorus pentoxide, a metal aluminum halide, an alkyl aluminum hydride, a metal borohydride, an organometallic reagent, and a palladium on carbon catalyst.

21. The method of claim 1, wherein the treating comprises heating the metathesis substrate to a temperature between 100° C. and 250° C.

22. The method of claim 1, wherein the treating comprises contacting the metathesis substrate with an acid anhydride.

23. The method of claim 1, wherein the treating comprises contacting the metathesis substrate with a desiccant.

24. The method of claim 1, wherein the treating comprises contacting the metathesis substrate with an adsorbent.

25. A method of metathesizing a substrate, comprising:
treating a metathesis substrate according to the method of claim 1; and
metathesizing the treated substrate in the presence of a metathesis catalyst to form a metathesized product.

* * * * *